(12) United States Patent
Berkman et al.

(10) Patent No.: US 9,328,129 B2
(45) Date of Patent: May 3, 2016

(54) PEPTIDOMIMETIC INHIBITORS OF PSMA

(75) Inventors: Clifford E. Berkman, Woodenville, WA (US); Henry F. Vanbrocklin, San Francisco, CA (US)

(73) Assignees: Washington State University, Pullman, WA (US); The Regents of the University of California, Oakland, CA (US)

( * ) Notice: Subject to any disclaimer, the term of this patent is extended or adjusted under 35 U.S.C. 154(b) by 271 days.

(21) Appl. No.: 13/884,394

(22) PCT Filed: Nov. 10, 2011

(86) PCT No.: PCT/US2011/060088
§ 371 (c)(1),
(2), (4) Date: Sep. 17, 2013

(87) PCT Pub. No.: WO2012/064914
PCT Pub. Date: May 18, 2012

(65) Prior Publication Data
US 2014/0010758 A1 Jan. 9, 2014

Related U.S. Application Data

(60) Provisional application No. 61/412,917, filed on Nov. 12, 2010.

(51) Int. Cl.
| | | |
|---|---|---|
| *A61K 51/00* | (2006.01) | |
| *A61M 36/14* | (2006.01) | |
| *C07F 9/24* | (2006.01) | |
| *A61K 31/664* | (2006.01) | |
| *A61K 51/04* | (2006.01) | |
| *C07F 13/00* | (2006.01) | |
| *G01N 33/574* | (2006.01) | |

(52) U.S. Cl.
CPC ............ *C07F 9/24* (2013.01); *A61K 31/664* (2013.01); *A61K 51/0489* (2013.01); *C07F 9/2408* (2013.01); *C07F 9/2458* (2013.01); *C07F 13/005* (2013.01); *G01N 33/57492* (2013.01)

(58) Field of Classification Search
CPC . A61K 31/00; A61K 31/664; A61K 2121/00; A61K 2123/00; A61K 51/00; A61K 51/04; A61K 51/0489; C07F 9/2408; C07F 9/2458; C07F 13/005; C07F 9/24; G01N 33/57492
USPC ........... 424/1.11, 1.37, 1.65, 1.69, 1.77, 1.81, 424/1.85, 1.89, 9.1, 9.6; 514/1, 1.1; 530/300
See application file for complete search history.

(56) References Cited

U.S. PATENT DOCUMENTS

2010/0183517 A1    7/2010  Berkman

OTHER PUBLICATIONS

Lebl and Houghten, American Peptide Society, 2001, pp. 58-60.*
Liu et al., "Psuedoirreversible Inhibition of Prostate-Specific Membrane Antigen by Phosphoramidate Peptidomimetics", Biochemistry, 2007, pp. 12658-12660, vol. 47.
Wu et al., "The Molecular Pruning of a Phosphoramidate Peptomimetic Inhibitor of a Prostate-Specific Membrane Antigen", Bioorg. Med. Chem., 2007, pp. 7434-7443, vol. 15.

* cited by examiner

*Primary Examiner* — D L Jones
(74) *Attorney, Agent, or Firm* — Whitman, Curtis, Christofferson & Cook, P.C.

(57) ABSTRACT

Compounds of the formulae, (I), wherein each variable is as defined herein are provided which are useful in (i) diagnostic methods for detecting and/or identifying cells presenting PSMA; (2) compositions comprising a compound of the invention together with a pharmaceutically acceptable carrier, excipient, and/or diluent; (3) methods for inhibiting or treating prostrate cancer; and (4) methods for blocking or destabilizing neovasculature of a tumor.

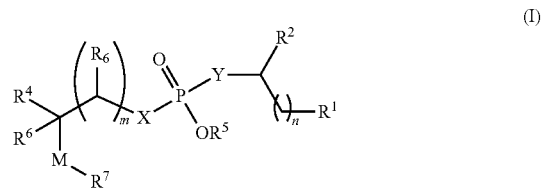

10 Claims, 3 Drawing Sheets

PEPTIDOMIMETIC INHIBITORS OF PSMA

STATEMENT OF GOVERNMENT INTEREST

This application was supported by Grant No. IR2ICA135463-01, IR21CAI22126-01 and IR01CA140617-01A2 awarded by National Institutes of Health and the National Cancer Institute. The U.S. government has certain rights in the invention.

BACKGROUND OF THE INVENTION

1. Field of the Invention

The present invention relates to small molecules having high affinity and specificity to prostrate-specific membrane antigen (PSMA) and methods of using them for diagnostic and therapeutic purposes.

2. Summary of the Related Art

Prostate-specific membrane antigen (PSMA) is uniquely overexpressed on the surface of prostate cancer cells as well as in the neovasculature of a variety of solid tumors. As a result, PSMA has attracted attention as a clinical biomarker for detection and management of prostate cancer. Generally, these approaches utilize an antibody specifically targeted at PSMA to direct imaging or therapeutic agents. For example, ProstaScint (Cytogen, Philadelphia, Pa.), which has been approved by the FDA for the detection and imaging of prostate cancer, utilizes an antibody to deliver a chelated radioisotope (Indium-111). However, it is now recognized that the ProstaScint technology is limited to the detection of dead cells and therefore its clinical relevance is questionable.

The success of cancer diagnosis and therapy using antibodies is limited by challenges such as slow elimination of these biomolecules from the blood and poor vascular permeability. In addition, large antibodies bound to cell-surface targets present a barrier for subsequent binding of additional antibodies at neighboring cell-surface sites resulting in a decreased cell-surface labeling.

In addition to serving as a cell-surface target for antibodies delivering diagnostic or therapeutic agents, a largely overlooked and unique property of PSMA is its enzymatic activity. That is, PSMA is capable of recognizing and processing molecules as small as dipeptides. Despite the existence of this property, it has been largely unexplored in terms of the development of novel diagnostic and therapeutic strategies. There are a few recent examples in the literature that have described results in detecting prostate cancer cells using labeled small-molecule inhibitors of PSMA.

Certain phosphoramidate PSMA inhibitors have been described in U.S. Pat. No. 7,696,185 to Berkman.

SUMMARY OF THE INVENTION

The present invention comprises compounds that bind to the prostate-specific membrane antigen (PSMA) with high affinity and specificity.

In one aspect, the present disclosure comprises compounds of one of the formulae,

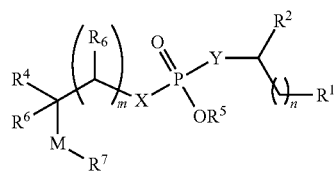

(I)

wherein each variable is as defined herein.

In another aspect, the present invention comprises compositions comprising a compound of the invention together with a pharmaceutically acceptable carrier, excipient, and/or diluent.

In another aspect, the present invention comprises diagnostic methods for detecting and/or identifying cells presenting PSMA comprising contacting (or causing to be contacted) a cell suspected of presenting PSMA with a compound of the invention.

In another aspect, the present invention comprises compositions comprising a compound of the invention together with a pharmaceutically acceptable carrier, excipient, and/or diluent.

In another aspect, the present invention comprises methods for inhibiting or treating prostrate cancer comprising administering to a patient having prostrate cancer a therapeutically effective amount of a compound of the invention linked to a prostrate cancer therapeutic agent (or a composition thereof).

In another aspect, the present invention comprises methods for blocking or destabilizing neovasculature of a tumor, comprising administering to a patient having a tumor; or contacting a tumor cell with a therapeutically effective amount of a compound or composition of the invention.

DETAILED DESCRIPTION OF THE INVENTION

Figure 1:
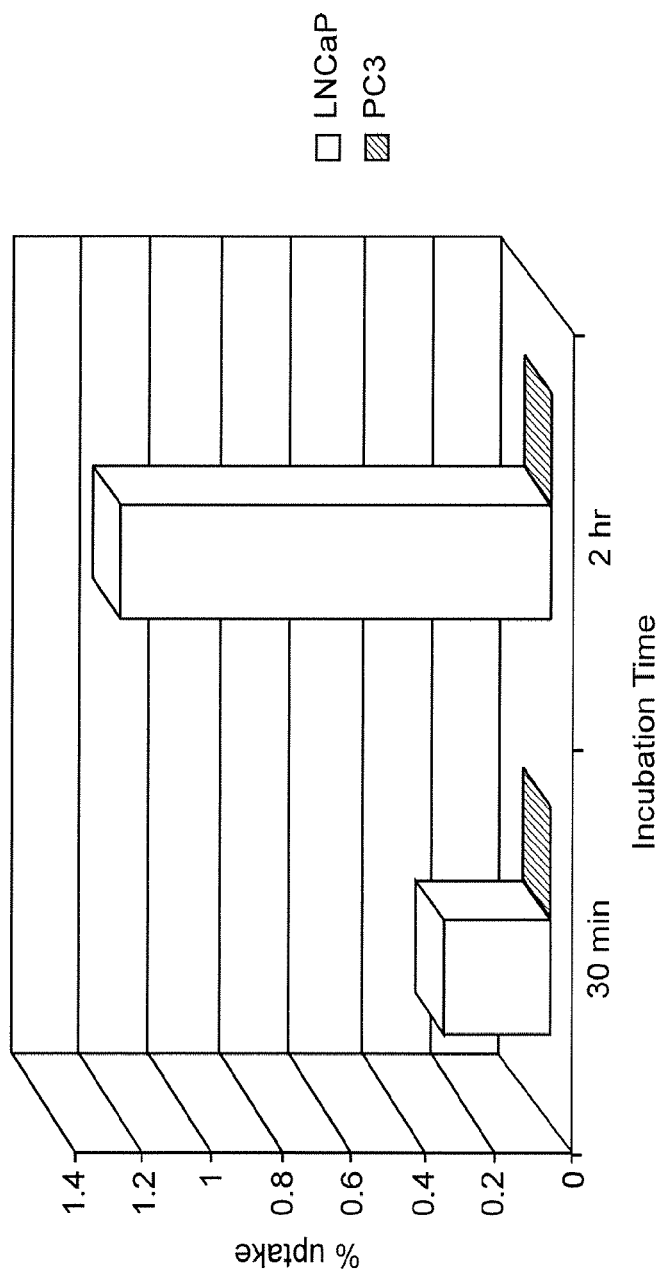
FIG. 1 shows uptake of DTPA-SCN-CTT-54 labeled with pertechnetate ($^{99m}TcO_4^-$) reduced with $SnCl_2$ by LNCaP (PSMA+) and PC3 (PSMA−) cells.

In embodiment (1) of the first aspect, the invention comprises the compound of formula (I),

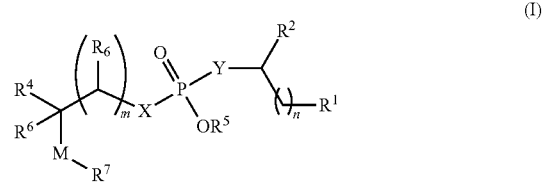

(I)

and pharmaceutically acceptable salts thereof, wherein

X and Y are independently —O— or —N(R)—, wherein each R is independently hydrogen, —$C_1$-$C_7$ alkyl, —$C_1$-$C_7$ alkylaryl, —$C_1$-$C_7$ alkylheteroaryl, or a protecting group;

m is 1, 2, 3, 4, 5, or 6;

n is 1, 2, 3, 4, 5, or 6;

$R^1$ and $R^2$ are each independently —$C(O)OR^3$, —$C(O)N(R^3)_2$, —$P(O)(OR^3)_2$, —$OP(O)(OR^3)_2$, —$S(O)_2R^3$, —$S(O)_2OR^3$, —$S(O)_2N(R^3)_2$, or tetrazolyl;

each $R^3$ is independently hydrogen, —$C_1$-$C_7$ alkyl, —$C_1$-$C_7$ alkylaryl, alkylheteroaryl, or a protecting group;

$R^4$ is hydrogen, —$C(O)OR^3$, —$C(O)N(R^3)_2$, —$P(O)(OR^3)_2$, —$OP(O)(OR^3)_2$, —$S(O)_2R^3$, —$S(O)_2OR^3$, —$S(O)_2N(R^3)_2$, or tetrazolyl;

$R^5$ is hydrogen; —$C_1$-$C_7$ alkyl, —$C_1$-$C_7$ alkylaryl, —$C_1$-$C_7$ alkylheteroaryl, or a protecting group;

each $R^6$ is independently hydrogen, $C_1$-$C_4$ alkyl, or fluoro;

M is —O—, —S—, —N($R^{31}$)—, or —$CH_2$—, wherein $R^{31}$ is hydrogen, —$C_1$-$C_7$ alkyl, —$C_1$-$C_7$ alkylaryl, —$C_1$-$C_7$ alkylheteroaryl, or a protecting group;

$R^7$ is L-$R^{10}$, wherein
L is —C(O)—, -(Pep)-C(O)—, —C(O)N(H)—, —C(O)O—, —C(S)N(H)—, or —C(S)O—, wherein
Pep is a polypeptide of 1-20 amino acids; and
$R^{10}$ is aryl-$R^9$, -heteroaryl-$R^9$, —$C_1$-$C_7$alkyl-aryl-$R^9$, —$C_1$-$C_7$alkyl-heteroaryl-$R^9$, —$C_1$-$C_7$alkyl-$R^8$, -aryl-$C_1$-$C_7$alkyl-$R^8$, or -heteroaryl-$C_1$-$C_7$alkyl-$R^8$, wherein
the aryl, heteroaryl, -alkyl-aryl, -aryl-alkyl, -alkyl-heteroaryl, and -heteroaryl-alkyl groups are optionally and independently substituted with one, two, or three groups which are each independently —C(O)$R^{11}$, —CO(O)$R^{12}$, —C(O)N($R^{12}$)$_2$, wherein
each $R^{11}$ is independently hydrogen, —$C_1$-$C_7$ alkyl, —$C_1$-$C_7$ alkylaryl, or —$C_1$-$C_7$ alkylheteroaryl; and
each $R^{12}$ is independently $R^{10}$ or a protecting group; and $R^8$ is —C(H)(COO$R^3$)N($R^{15}$)-$L^1$-($C_1$-$C_7$)alkyl-$R^9$,
—C(H)(COO$R^3$)N($R^{15}$)-$L^1$-aryl-$R^9$,
—C(H)(COO$R^3$)N($R^{15}$)-$L^1$-heteroaryl-$R^9$,
—C(H)(COO$R^3$)N($R^{15}$)-$L^1$-aryl($C_1$-$C_7$)alkyl-$R^9$,
—C(H)(COO$R^3$)N($R^{15}$)-$L^1$-heteroaryl($C_1$-$C_7$)alkyl-$R^9$,
—C(H)(COO$R^3$)N($R^{15}$)-$L^1$-G-$CH_2CH_2$—$R^9$,
—C(H)(COO$R^3$)N($R^{15}$)-$L^1$-($C_1$-$C_7$)alkyl-O—($C_1$-$C_7$)alkyl-$R^9$,
or $R^9$,
wherein
$R^{15}$ is hydrogen, —$C_1$-$C_7$ alkyl, —$C_1$-$C_7$ alkylaryl, —$C_1$-$C_7$ alkylheteroaryl, or a protecting group;
$L^1$ is —C(O)—, —C(O)N(H)—, —C(O)O—, —C(S)N(H)—, or —C(S)O—; and
the aryl, heteroaryl, arylalkyl, and heteroarylalkyl groups are optionally substituted with one, two, or three groups which are each independently halomethyl dihalomethyl, trihalomethyl, —C(O)$R^{81}$, —C(O)N($R^{82}$)$_2$, wherein
each $R^{81}$ is independently hydrogen, —$C_1$-$C_7$ alkyl, —$C_1$-$C_7$ alkylaryl, or —$C_1$-$C_7$ alkylheteroaryl; and
each $R^{82}$ is independently $R^{81}$ or a protecting group;
G is —($CH_2CH_2O$)$_q$—, wherein q is an integer from 1 to 200 (e.g., q is 100-200, 150-200, 1-100, 1-50, 1-10, or 1, 2, 3, 4, 5, 6, 7, 8, 9, or 10);
$R^9$ is (i) —$N_3$, —C≡CH, —$ONH_2$, —C(O)N(H)$NH_2$, or —N(H)$NH_2$;
(ii) a detectable label, a cytotoxic group, or biotin;
(iii) a pendant group comprising either a detectable label, a cytotoxic group, or biotin; or
(iv) a pendant group bonded to a solid support.

The invention further comprises subgenera of embodiment (1) of the first aspect in which the substituents are selected as any and all combinations of R, $R^1$, $R^2$, $R^4$, $R^5$, $R^6$, $R^7$, $R^8$, $R^{11}$, $R^{12}$, $R^{15}$, $R^{31}$, $R^{81}$, $R^{82}$, L, $L^1$, M, X, Y, m, and n, as defined herein, including without limitation, the following:

$R^1$ in formula (I) is one of the following groups (1a)-(1l):
(1a) —C(O)O$R^3$ or —C(O)N($R^3$)$_2$.
(1b) —C(O)O$R^3$.
(1c) —C(O)O$R^{34}$, wherein $R^{34}$ is hydrogen, —$C_1$-$C_7$ alkyl, —$C_1$-$C_7$ alkylaryl, or a protecting group.
(1d) —C(O)O$R^{34}$, wherein $R^{34}$ is hydrogen or —$C_1$-$C_7$ alkyl aryl.
(1e) —C(O)O$R^{34}$, wherein $R^{34}$ is hydrogen or benzyl.
(1f) —C(O)O$R^{34}$, wherein $R^{34}$ is benzyl,
(1g) —C(O)O$R^{34}$, wherein $R^{34}$ is hydrogen or a protecting group.
(1h) —C(O)O$R^{34}$, wherein $R^{34}$ is a protecting group.
(1i) —C(O)OH.
(1j) —P(O)(O$R^3$)$_2$ or —OP(O)(O$R^3$)$_2$.
(1k) —S(O)$_2R^3$, —S(O)$_2$O$R^3$ or —S(O)$_2$N($R^3$)$_2$.
(1l) tetrazolyl.

$R^2$ in formula (I) is one of the following groups (2a)-(2l):
(2a) —C(O)O$R^3$ or —C(O)N($R^3$)$_2$.
(2b) —C(O)O$R^3$.
(2c) —C(O)O$R^{32}$ wherein $R^{32}$ is hydrogen, —$C_1$-$C_7$ alkyl, —$C_1$-$C_7$ alkylaryl, or a protecting group.
(2d) —C(O)O$R^{32}$ wherein $R^{32}$ is hydrogen or —$C_1$-$C_7$ alkylaryl.
(2e) —C(O)O$R^{32}$ wherein $R^{32}$ is hydrogen or benzyl.
(2f) —C(O)O$R^{32}$ wherein $R^{32}$ is benzyl.
(2g) —C(O)OH.
(2h) —P(O)(O$R^3$)$_2$ or —OP(O)(O$R^3$)$_2$.
(2i) —S(O)$_2R^3$, —S(O)$_2$O$R^3$ or —S(O)$_2$N($R^3$)$_2$.
(2j) tetrazolyl.

$R^4$ in formula (I) is one of the following groups (3a)-(3k):
(3a) hydrogen, —C(O)O$R^3$, or —C(O)N($R^3$)$_2$.
(3b) hydrogen or —C(O)O$R^3$.
(3e) —C(O)O$R^{33}$ wherein $R^{33}$ is hydrogen, —$C_1$-$C_7$ alkyl, —$C_1$-$C_7$ alkylaryl, or a protecting group.
(3d) —C(O)O$R^{33}$ wherein $R^{33}$ is hydrogen or —$C_1$-$C_7$ alkylaryl.
(3e) —C(O)O$R^{33}$ wherein $R^{33}$ is hydrogen or benzyl.
(3f) —C(O)O$R^{33}$ wherein $R^{33}$ is benzyl.
(3g) —C(O)OH.
(3h) —P(O)(O$R^3$)$_2$ or —OP(O)(O$R^3$)$_2$.
(3i) —S(O)$_2R^3$, —S(O)$_2$O$R^3$ or —S(O)$_2$N($R^3$)$_2$.
(3j) tetrazolyl.
(3k) hydrogen.

$R^7$ in formula (I) is one of the following groups (4a)-(4w):
(4a) C(O)$R^{10}$.
(4b) (Pep)-C(O)$R^{10}$.
(4e) —C(O)$C_1$-$C_7$alkyl-$R^8$.
(4d) —C(O)$C_1$-$C_7$alkyl-$R^8$, wherein $R^8$ is —C(H)(COO$R^3$)N(H)-$L^1$-($C_1$-$C_7$)alkyl-$R^9$, —C(H)(COO$R^3$)N(H)-$L^1$-heteroaryl-$R^9$, —C(H)(COO$R^3$)N(H)-$L^1$-G-$CH_2CH_2$—$R^9$, —C(H)(COO$R^3$)N(H)-$L^1$-($C_1$-$C_7$)alkyl-O—($C_1$-$C_7$)alkyl-$R^9$, or $R^9$.
(4e) —C(O)—$C_1$-$C_7$alkyl-$R^8$, wherein $R^8$ is —C(H)(COO$R^3$)N(H)-$L^1$-($C_1$-$C_7$)alkyl-$R^9$, —C(H)(COO$R^3$)N(H)-$L^1$-G-$CH_2CH_2$—$R^9$, —C(H)(COO$R^3$)N(H)-$L^1$-($C_1$-$C_7$)alkyl-O—($C_1$-$C_7$)alkyl-$R^9$, or $R^9$;
(4f) —C(O)—$C_1$-$C_7$alkyl-C(H)(COO$R^3$)N(H)-$L^1$-($C_1$-$C_7$)alkyl-$R^9$.
(4g) —C(O)—$C_1$-$C_7$alkyl-C(H)(COO$R^3$)N(H)-$L^1$-heteroaryl-$R^9$,
(4h) —C(O)—$C_1$-$C_7$alkyl-C(H)(COO$R^3$)N(H)-$L^1$-pyridyl-$R^9$,
(4i) —C(O)$C_1$-$C_7$alkyl-C(H)(COO$R^3$)N(H)-$L^1$-aryl-$R^9$,
(4j) —C(O)—$C_1$-$C_7$alkyl-C(H)(COO$R^3$)N(H)-$L^1$-phenyl-$R^9$,
(4k) —C(O)—$C_1$-$C_7$alkyl —C(H)(COO$R^3$)N(H)-$L^1$-G-$CH_2CH_2$—$R^9$.
(4l) —C(O)—$C_1$-$C_7$alkyl-C(H)(COO$R^3$)N(H)-$L^1$-($C_1$-$C_7$)alkyl-O—($C_1$-$C_7$)alkyl-$R^9$.
(4m) (Pep)-C(O)—$C_1$-$C_7$alkyl-$R^8$, wherein $R^8$ is C(H)(COO$R^3$)N(H)-$L^1$-($C_1$-$C_7$)alkyl-$R^9$, —C(H)(COO$R^3$)N(H)-$L^1$-heteroaryl-$R^9$, —C(H)(COO$R^3$)N(H)-$L^1$-G-$CH_2CH_2$—$R^9$, —C(H)(COO$R^3$)N(H)-$L^1$-($C_1$-$C_7$)alkyl-O—($C_1$-$C_7$)alkyl-$R^9$, or —$R^9$.
(4n) (Pep)-C(O)—$C_1$-$C_7$alkyl-$R^8$, wherein $R^8$ is C(H)(COO$R^3$)N(H)-$L^1$-($C_1$-$C_7$)alkyl-$R^9$, —C(H)(COO$R^3$)N(H)-$L^1$-G-$CH_2CH_2$—$R^9$, —C(H)(COO$R^3$)N(H)-$L^1$-($C_1$-$C_7$)alkyl-O—($C_1$-$C_7$)alkyl-$R^9$, or $R^9$.

(4o) -(Pep)-C(O)—$C_1$-$C_7$alkyl-C(H)(COOR$^3$)N(H)-L$^1$-($C_1$-$C_7$)alkyl-R$^9$.
(4p) -(Pep)-C(O)—$C_1$-$C_7$alkyl-C(H)(COOR$^3$)N(H)-L$^1$-G-CH$_2$CH$_2$—R$^9$.
(4q) -(Pep)-C(O)—$C_1$-$C_7$alkyl-C(H)(COOR$^3$)N(H)-L$^1$-($C_1$-$C_7$)alkyl-O—($C_1$-$C_7$)alkyl-R$^9$.
(4r) -(Pep)-C(O)—$C_1$-$C_7$alkyl-R$^8$.
(4s) any one of groups (4d)-(4o), wherein L$^1$ is —C(O)—.
(4t) any one of groups (4d)-(4o), wherein L$^1$ is —C(O)—, —C(O)N(H)—, —C(O)O—, —C(S)N(H)—, or —C(S)O—.
(4u) any one of groups (4d)-(4o), wherein L$^1$ is —C(O)N(H)—, —C(O)O—, —C(S)N(H)—, or —C(S)O—.
(4v) any one of groups (4d)-(4o), wherein L$^1$ is —C(O)N(H)— or —C(S)N(H)—.
(4w) any one of groups (4d)-(4o), wherein L$^1$ is —C(O)N(H)—.

R$^8$ in formula (I) is one of the following groups (5a)-(5o):
(5a) —C(H)(COOR$^3$)N(H)-L$^1$-($C_1$-$C_7$)alkyl-R$^9$, —C(H)(COOR$^3$)N(H)-L$^1$-heteroaryl-R$^9$, —C(H)(COOR$^3$)N(H)-L$^1$-G-CH$_2$CH$_2$—R$^9$, —C(H)(COOR$^3$)N(H)-L$^1$-($C_1$-$C_7$)alkyl-O—($C_1$-$C_7$)alkyl-R$^9$, or R$^9$.
(5b) —C(H)(COOR$^3$)N(H)-L$^1$-($C_1$-$C_7$)alkyl-R$^9$, —C(H)(COOR$^3$)N(H)-L$^1$-G-CH$_2$CH$_2$—R$^9$, —C(H)(COOR$^3$)N(H)-L$^1$-($C_1$-$C_7$)alkyl-O—($C_1$-$C_7$)alkyl-R$^9$, or —R$^9$.
(5c) —C(H)(COOR$^3$)N(H)-L$^1$-($C_1$-$C_7$)alkyl-R$^9$.
(5d) —C(H)(COOR$^3$)N(H)-L$^1$-G-CH$_2$CH$_2$—R$^9$.
(5e) —C(H)(COOR$^3$)N(H)-L$^1$-($C_1$-$C_7$)alkyl-O—($C_1$-$C_7$)alkyl-R$^9$.
(5f) —C(H)(COOR$^3$)N(H)-L$^1$-heteroaryl-R$^9$,
(5g) —C(H)(COOR$^3$)N(H)-L$^1$-pyridyl-R$^9$,
(5h) —C(H)(COOR$^3$)N(H)-L$^1$-aryl-R$^9$,
(5i) —C(H)(COOR$^3$)N(H)-L$^1$-phenyl-R$^9$,
(5j) —R$^9$.
(5k) any one of groups (5a)-(5g), wherein L$^1$ is —C(O)—.
(5l) any one of groups (5a)-(5g), wherein L$^1$ is —C(O)—, —C(O)N(H)—, —C(O)O—, —C(S)N(H)—, or —C(S)O—.
(5m) any one of groups (5a)-(5g), wherein L$^1$ is —C(O)N(H)—, —C(O)O—, —C(S)N(H)—, or —C(S)O—.
(5n) any one of groups (5a)-(5g), wherein L$^1$ is —C(O)N(H)— or —C(S)N(H)—.
(5o) any one of groups (5a)-(5g), wherein L$^1$ is —C(O)N(H)—.

L in formula (I) is one of the following groups (5p)-(5u):
(5p) —C(O)—.
(5q) -(Pep)-C(O)—.
(5r) —C(O)—, —C(O)N(H)—, —C(O)O—, —C(S)N(H)—, or —C(S)O—.
(5s) —C(O)N(H)—, —C(O)O—, —C(S)N(H)—, or —C(S)O—.
(5t) —C(O)N(H)— or —C(S)N(H)—.
(5u) —C(O)N(H)—.

L$^1$ in formula (I) is one of the following groups (5v)-(5z):
(5v) —C(O)—.
(5w) —C(O)—, —C(O)N(H)—, —C(O)O—, —C(S)N(H)—, or —C(S)O—.
(5x) —C(O)N(H)—, —C(O)O—, —C(S)N(H)—, or —C(S)O—.
(5y) —C(O)N(H)— or —C(S)N(H)—.
(5z) —C(O)N(H)—.

M in formula (I) is one of the following groups (6a)-(6e):
(6a) —O—, —S—, or —N(R$^{31}$)—.
(6b) —O—.
(6c) —S—.
(6d) —N(R$^3$)—.
(6e) —N(H)—.

X and Y in formula (I) are one of the following groups (7a)-(7g):
(7a) X and Y are each —O—.
(7b) X is —O— and Y is —N(R)—.
(7c) Y is —O— and X is —N(R)—.
(7d) X is —O— and Y is —N(H)—.
(7e) Y is —O— and X is —N(H)—.
(7f) X and Y are each —N(R)—.
(7g) X and Y are each —N(H)—.

m and n in formula (I) are one of the following groups (8a)-(8g):
(8a) m is 1, 2, 3, 4, 5, or 6 and n is 1, 2, or 3.
(8b) m is 1, 2, or 3 and n is 1, 2, 3, 4, 5, or 6.
(8c) m is 1, 2, or 3 and n is 1, 2, or 3.
(8d) m is 1 or 2 and n is 1 or 2.
(8e) m is 1 or 2 and n is 1.
(8f) m is 1 and n is 1 or 2.
(8g) m is 1 and n is 1.

R$^5$ in formula (I) is one of the following groups (8h)-(8l):
(8h) hydrogen, —$C_1$-$C_7$ alkyl, —$C_1$-$C_7$ alkylaryl, or —$C_1$-$C_7$ alkylheteroaryl.
(8i) hydrogen, methyl, ethyl, t-butyl, or benzyl.
(8j) hydrogen.
(8k) hydrogen or benzyl.
(8l) benzyl.

each R$^6$ in formula (I) is independently one of the following groups (8m)-(8q):
(8m) methyl or fluoro.
(8n) hydrogen, methyl, or fluoro.
(8o) hydrogen or methyl.
(8p) hydrogen or fluoro.
(8q) hydrogen.

each of variables R, R$^{11}$, R$^{12}$, R$^{15}$, R$^{31}$, R$^{81}$, and R$^{82}$ in formula (I) are independently selected from one of the following groups (8r)-(8v):
(8r) hydrogen, —$C_1$-$C_7$ alkyl, —$C_1$-$C_7$ alkylaryl, or —$C_1$-$C_7$ alkylheteroaryl.
(8s) hydrogen, —$C_1$-$C_7$ alkyl, or —$C_1$-$C_7$ alkylaryl.
(8t) hydrogen or —$C_1$-$C_7$ alkyl.
(8u) hydrogen.
(8v) —$C_1$-$C_7$ alkyl.

Particular embodiments of this aspect of the invention include compounds of formula (I) wherein are defined in each of the following rows, wherein each entry is a group number as defined above for formula (I) (e.g., (8e) refers to n is 1-6, in a sub-embodiment m is 1, n is 1):

| Embodiment | R$^1$ | R$^2$ | R$^4$ | R$^6$ | R$^7$ | X & Y | m & n | M |
|---|---|---|---|---|---|---|---|---|
| I-1 | 1b | 2b | 3b | 8m | 4d | 7a | 8c | 6a |
| I-2 | 1b | 2b | 3e | 8m | 4d | 7a | 8c | 6a |
| I-3 | 1b | 2b | 3k | 8m | 4d | 7a | 8c | 6a |
| I-4 | 1b | 2b | 3b | 8m | 4d | 7a | 8c | 6d |
| I-5 | 1b | 2b | 3e | 8m | 4d | 7a | 8c | 6d |
| I-6 | 1b | 2b | 3k | 8m | 4d | 7a | 8c | 6d |
| I-7 | 1b | 2b | 3b | 8m | 4d | 7a | 8e | 6a |
| I-8 | 1b | 2b | 3e | 8m | 4d | 7a | 8e | 6a |
| I-9 | 1b | 2b | 3k | 8m | 4d | 7a | 8e | 6a |
| I-10 | 1b | 2b | 3b | 8m | 4d | 7a | 8e | 6d |
| I-11 | 1b | 2b | 3e | 8m | 4d | 7a | 8e | 6d |
| I-12 | 1b | 2b | 3k | 8m | 4d | 7a | 8e | 6d |
| I-13 | 1b | 2b | 3b | 8m | 4d | 7b | 8c | 6a |
| I-14 | 1b | 2b | 3e | 8m | 4d | 7b | 8c | 6a |
| I-15 | 1b | 2b | 3k | 8m | 4d | 7b | 8c | 6a |
| I-16 | 1b | 2b | 3b | 8m | 4d | 7b | 8c | 6d |
| I-17 | 1b | 2b | 3e | 8m | 4d | 7b | 8c | 6d |
| I-18 | 1b | 2b | 3k | 8m | 4d | 7b | 8c | 6d |
| I-19 | 1b | 2b | 3b | 8m | 4d | 7b | 8e | 6a |
| I-20 | 1b | 2b | 3e | 8m | 4d | 7b | 8e | 6a |

| Embodiment | R¹ | R² | R⁴ | R⁶ | R⁷ | X & Y | m & n | M |
|---|---|---|---|---|---|---|---|---|
| I-21 | 1b | 2b | 3k | 8m | 4d | 7b | 8e | 6a |
| I-22 | 1b | 2b | 3b | 8m | 4d | 7b | 8e | 6d |
| I-23 | 1b | 2b | 3e | 8m | 4d | 7b | 8e | 6d |
| I-24 | 1b | 2b | 3k | 8m | 4d | 7b | 8e | 6d |
| I-25 | 1b | 2b | 3b | 8m | 4f | 7a | 8c | 6a |
| I-26 | 1b | 2b | 3e | 8m | 4f | 7a | 8c | 6a |
| I-27 | 1b | 2b | 3k | 8m | 4f | 7a | 8c | 6a |
| I-28 | 1b | 2b | 3b | 8m | 4f | 7a | 8c | 6d |
| I-29 | 1b | 2b | 3e | 8m | 4f | 7a | 8c | 6d |
| I-30 | 1b | 2b | 3k | 8m | 4f | 7a | 8c | 6d |
| I-31 | 1b | 2b | 3b | 8m | 4f | 7a | 8e | 6a |
| I-32 | 1b | 2b | 3e | 8m | 4f | 7a | 8e | 6a |
| I-33 | 1b | 2b | 3k | 8m | 4f | 7a | 8e | 6a |
| I-34 | 1b | 2b | 3b | 8m | 4f | 7a | 8e | 6d |
| I-35 | 1b | 2b | 3e | 8m | 4f | 7a | 8e | 6d |
| I-36 | 1b | 2b | 3k | 8m | 4f | 7a | 8e | 6d |
| I-37 | 1b | 2b | 3b | 8m | 4f | 7b | 8c | 6a |
| I-38 | 1b | 2b | 3e | 8m | 4f | 7b | 8c | 6a |
| I-39 | 1b | 2b | 3k | 8m | 4f | 7b | 8c | 6a |
| I-40 | 1b | 2b | 3b | 8m | 4f | 7b | 8c | 6d |
| I-41 | 1b | 2b | 3e | 8m | 4f | 7b | 8c | 6d |
| I-42 | 1b | 2b | 3k | 8m | 4f | 7b | 8c | 6d |
| I-43 | 1b | 2b | 3b | 8m | 4f | 7b | 8e | 6a |
| I-44 | 1b | 2b | 3e | 8m | 4f | 7b | 8e | 6a |
| I-45 | 1b | 2b | 3k | 8m | 4f | 7b | 8e | 6a |
| I-46 | 1b | 2b | 3b | 8m | 4f | 7b | 8e | 6d |
| I-47 | 1b | 2b | 3e | 8m | 4f | 7b | 8e | 6d |
| I-48 | 1b | 2b | 3k | 8m | 4f | 7b | 8e | 6d |
| I-49 | 1b | 2e | 3b | 8m | 4d | 7a | 8c | 6a |
| I-50 | 1b | 2e | 3e | 8m | 4d | 7a | 8c | 6a |
| I-51 | 1b | 2e | 3k | 8m | 4d | 7a | 8c | 6a |
| I-52 | 1b | 2e | 3b | 8m | 4d | 7a | 8c | 6d |
| I-53 | 1b | 2e | 3e | 8m | 4d | 7a | 8c | 6d |
| I-54 | 1b | 2e | 3k | 8m | 4d | 7a | 8c | 6d |
| I-55 | 1b | 2e | 3b | 8m | 4d | 7a | 8e | 6a |
| I-56 | 1b | 2e | 3e | 8m | 4d | 7a | 8e | 6a |
| I-57 | 1b | 2e | 3k | 8m | 4d | 7a | 8e | 6a |
| I-58 | 1b | 2e | 3b | 8m | 4d | 7a | 8e | 6d |
| I-59 | 1b | 2e | 3e | 8m | 4d | 7a | 8e | 6d |
| I-60 | 1b | 2e | 3k | 8m | 4d | 7a | 8e | 6d |
| I-61 | 1b | 2e | 3b | 8m | 4d | 7b | 8c | 6a |
| I-62 | 1b | 2e | 3e | 8m | 4d | 7b | 8c | 6a |
| I-63 | 1b | 2e | 3k | 8m | 4d | 7b | 8c | 6a |
| I-64 | 1b | 2e | 3b | 8m | 4d | 7b | 8c | 6d |
| I-65 | 1b | 2e | 3e | 8m | 4d | 7b | 8c | 6d |
| I-66 | 1b | 2e | 3k | 8m | 4d | 7b | 8c | 6d |
| I-67 | 1b | 2e | 3b | 8m | 4d | 7b | 8e | 6a |
| I-68 | 1b | 2e | 3e | 8m | 4d | 7b | 8e | 6a |
| I-69 | 1b | 2e | 3k | 8m | 4d | 7b | 8e | 6a |
| I-70 | 1b | 2e | 3b | 8m | 4d | 7b | 8e | 6d |
| I-71 | 1b | 2e | 3e | 8m | 4d | 7b | 8e | 6d |
| I-72 | 1b | 2e | 3k | 8m | 4d | 7b | 8e | 6d |
| I-73 | 1b | 2e | 3b | 8m | 4f | 7a | 8c | 6a |
| I-74 | 1b | 2e | 3e | 8m | 4f | 7a | 8c | 6a |
| I-75 | 1b | 2e | 3k | 8m | 4f | 7a | 8c | 6a |
| I-76 | 1b | 2e | 3b | 8m | 4f | 7a | 8c | 6d |
| I-77 | 1b | 2e | 3e | 8m | 4f | 7a | 8c | 6d |
| I-78 | 1b | 2e | 3k | 8m | 4f | 7a | 8c | 6d |
| I-79 | 1b | 2e | 3b | 8m | 4f | 7a | 8e | 6a |
| I-80 | 1b | 2e | 3e | 8m | 4f | 7a | 8e | 6a |
| I-81 | 1b | 2e | 3k | 8m | 4f | 7a | 8e | 6a |
| I-82 | 1b | 2e | 3b | 8m | 4f | 7a | 8e | 6d |
| I-83 | 1b | 2e | 3e | 8m | 4f | 7a | 8e | 6d |
| I-84 | 1b | 2e | 3k | 8m | 4f | 7a | 8e | 6d |
| I-85 | 1b | 2e | 3b | 8m | 4f | 7b | 8c | 6a |
| I-86 | 1b | 2e | 3e | 8m | 4f | 7b | 8c | 6a |
| I-87 | 1b | 2e | 3k | 8m | 4f | 7b | 8c | 6a |
| I-88 | 1b | 2e | 3b | 8m | 4f | 7b | 8c | 6d |
| I-89 | 1b | 2e | 3e | 8m | 4f | 7b | 8c | 6d |
| I-90 | 1b | 2e | 3k | 8m | 4f | 7b | 8c | 6d |
| I-91 | 1b | 2e | 3b | 8m | 4f | 7b | 8e | 6a |
| I-92 | 1b | 2e | 3e | 8m | 4f | 7b | 8e | 6a |
| I-93 | 1b | 2e | 3k | 8m | 4f | 7b | 8e | 6a |
| I-94 | 1b | 2e | 3b | 8m | 4f | 7b | 8e | 6d |
| I-95 | 1b | 2e | 3e | 8m | 4f | 7b | 8e | 6d |
| I-96 | 1b | 2e | 3k | 8m | 4f | 7b | 8e | 6d |
| I-97 | 1e | 2b | 3b | 8m | 4d | 7a | 8c | 6a |
| I-98 | 1e | 2b | 3e | 8m | 4d | 7a | 8c | 6a |
| I-99 | 1e | 2b | 3k | 8m | 4d | 7a | 8c | 6a |
| I-100 | 1e | 2b | 3b | 8m | 4d | 7a | 8c | 6d |
| I-101 | 1e | 2b | 3e | 8m | 4d | 7a | 8c | 6d |
| I-102 | 1e | 2b | 3k | 8m | 4d | 7a | 8c | 6d |
| I-103 | 1e | 2b | 3b | 8m | 4d | 7a | 8e | 6a |
| I-104 | 1e | 2b | 3e | 8m | 4d | 7a | 8e | 6a |
| I-105 | 1e | 2b | 3k | 8m | 4d | 7a | 8e | 6a |
| I-106 | 1e | 2b | 3b | 8m | 4d | 7a | 8e | 6d |
| I-107 | 1e | 2b | 3e | 8m | 4d | 7a | 8e | 6d |
| I-108 | 1e | 2b | 3k | 8m | 4d | 7a | 8e | 6d |
| I-109 | 1e | 2b | 3b | 8m | 4d | 7b | 8c | 6a |
| I-110 | 1e | 2b | 3e | 8m | 4d | 7b | 8c | 6a |
| I-111 | 1e | 2b | 3k | 8m | 4d | 7b | 8c | 6a |
| I-112 | 1e | 2b | 3b | 8m | 4d | 7b | 8c | 6d |
| I-113 | 1e | 2b | 3e | 8m | 4d | 7b | 8c | 6d |
| I-114 | 1e | 2b | 3k | 8m | 4d | 7b | 8c | 6d |
| I-115 | 1e | 2b | 3b | 8m | 4d | 7b | 8e | 6a |
| I-116 | 1e | 2b | 3e | 8m | 4d | 7b | 8e | 6a |
| I-117 | 1e | 2b | 3k | 8m | 4d | 7b | 8e | 6a |
| I-118 | 1e | 2b | 3b | 8m | 4d | 7b | 8e | 6d |
| I-119 | 1e | 2b | 3e | 8m | 4d | 7b | 8e | 6d |
| I-120 | 1e | 2b | 3k | 8m | 4d | 7b | 8e | 6d |
| I-121 | 1e | 2b | 3b | 8m | 4f | 7a | 8c | 6a |
| I-122 | 1e | 2b | 3e | 8m | 4f | 7a | 8c | 6a |
| I-123 | 1e | 2b | 3k | 8m | 4f | 7a | 8c | 6a |
| I-124 | 1e | 2b | 3b | 8m | 4f | 7a | 8c | 6d |
| I-125 | 1e | 2b | 3e | 8m | 4f | 7a | 8c | 6d |
| I-126 | 1e | 2b | 3k | 8m | 4f | 7a | 8c | 6d |
| I-127 | 1e | 2b | 3b | 8m | 4f | 7a | 8e | 6a |
| I-128 | 1e | 2b | 3e | 8m | 4f | 7a | 8e | 6a |
| I-129 | 1e | 2b | 3k | 8m | 4f | 7a | 8e | 6a |
| I-130 | 1e | 2b | 3b | 8m | 4f | 7a | 8e | 6d |
| I-131 | 1e | 2b | 3e | 8m | 4f | 7a | 8e | 6d |
| I-132 | 1e | 2b | 3k | 8m | 4f | 7a | 8e | 6d |
| I-133 | 1e | 2b | 3b | 8m | 4f | 7b | 8c | 6a |
| I-134 | 1e | 2b | 3e | 8m | 4f | 7b | 8c | 6a |
| I-135 | 1e | 2b | 3k | 8m | 4f | 7b | 8c | 6a |
| I-136 | 1e | 2b | 3b | 8m | 4f | 7b | 8c | 6d |
| I-137 | 1e | 2b | 3e | 8m | 4f | 7b | 8c | 6d |
| I-138 | 1e | 2b | 3k | 8m | 4f | 7b | 8c | 6d |
| I-139 | 1e | 2b | 3b | 8m | 4f | 7b | 8e | 6a |
| I-140 | 1e | 2b | 3e | 8m | 4f | 7b | 8e | 6a |
| I-141 | 1e | 2b | 3k | 8m | 4f | 7b | 8e | 6a |
| I-142 | 1e | 2b | 3b | 8m | 4f | 7b | 8e | 6d |
| I-143 | 1e | 2b | 3e | 8m | 4f | 7b | 8e | 6d |
| I-144 | 1e | 2b | 3k | 8m | 4f | 7b | 8e | 6d |
| I-145 | 1e | 2e | 3b | 8m | 4d | 7a | 8c | 6a |
| I-146 | 1e | 2e | 3e | 8m | 4d | 7a | 8c | 6a |
| I-147 | 1e | 2e | 3k | 8m | 4d | 7a | 8c | 6a |
| I-148 | 1e | 2e | 3b | 8m | 4d | 7a | 8c | 6d |
| I-149 | 1e | 2e | 3e | 8m | 4d | 7a | 8c | 6d |
| I-150 | 1e | 2e | 3k | 8m | 4d | 7a | 8c | 6d |
| I-151 | 1e | 2e | 3b | 8m | 4d | 7a | 8e | 6a |
| I-152 | 1e | 2e | 3e | 8m | 4d | 7a | 8e | 6a |
| I-153 | 1e | 2e | 3k | 8m | 4d | 7a | 8e | 6a |
| I-154 | 1e | 2e | 3b | 8m | 4d | 7a | 8e | 6d |
| I-155 | 1e | 2e | 3e | 8m | 4d | 7a | 8e | 6d |
| I-156 | 1e | 2e | 3k | 8m | 4d | 7a | 8e | 6d |
| I-157 | 1e | 2e | 3b | 8m | 4d | 7b | 8c | 6a |
| I-158 | 1e | 2e | 3e | 8m | 4d | 7b | 8c | 6a |
| I-159 | 1e | 2e | 3k | 8m | 4d | 7b | 8c | 6a |
| I-160 | 1e | 2e | 3b | 8m | 4d | 7b | 8c | 6d |
| I-161 | 1e | 2e | 3e | 8m | 4d | 7b | 8c | 6d |
| I-162 | 1e | 2e | 3k | 8m | 4d | 7b | 8c | 6d |
| I-163 | 1e | 2e | 3b | 8m | 4d | 7b | 8e | 6a |
| I-164 | 1e | 2e | 3e | 8m | 4d | 7b | 8e | 6a |
| I-165 | 1e | 2e | 3k | 8m | 4d | 7b | 8e | 6a |
| I-166 | 1e | 2e | 3b | 8m | 4d | 7b | 8e | 6d |
| I-167 | 1e | 2e | 3e | 8m | 4d | 7b | 8e | 6d |
| I-168 | 1e | 2e | 3k | 8m | 4d | 7b | 8e | 6d |
| I-169 | 1e | 2e | 3b | 8m | 4f | 7a | 8c | 6a |
| I-170 | 1e | 2e | 3e | 8m | 4f | 7a | 8c | 6a |
| I-171 | 1e | 2e | 3k | 8m | 4f | 7a | 8c | 6a |
| I-172 | 1e | 2e | 3b | 8m | 4f | 7a | 8c | 6d |
| I-173 | 1e | 2e | 3e | 8m | 4f | 7a | 8c | 6d |
| I-174 | 1e | 2e | 3k | 8m | 4f | 7a | 8c | 6d |

-continued

| Embodiment | R¹ | R² | R⁴ | R⁶ | R⁷ | X & Y | m & n | M |
|---|---|---|---|---|---|---|---|---|
| I-175 | 1e | 2e | 3b | 8m | 4f | 7a | 8e | 6a |
| I-176 | 1e | 2e | 3e | 8m | 4f | 7a | 8e | 6a |
| I-177 | 1e | 2e | 3k | 8m | 4f | 7a | 8e | 6a |
| I-178 | 1e | 2e | 3b | 8m | 4f | 7a | 8e | 6d |
| I-179 | 1e | 2e | 3e | 8m | 4f | 7a | 8e | 6d |
| I-180 | 1e | 2e | 3k | 8m | 4f | 7a | 8e | 6d |
| I-181 | 1e | 2e | 3b | 8m | 4f | 7b | 8c | 6a |
| I-182 | 1e | 2e | 3e | 8m | 4f | 7b | 8c | 6a |
| I-183 | 1e | 2e | 3k | 8m | 4f | 7b | 8c | 6a |
| I-184 | 1e | 2e | 3b | 8m | 4f | 7b | 8c | 6d |
| I-185 | 1e | 2e | 3e | 8m | 4f | 7b | 8c | 6d |
| I-186 | 1e | 2e | 3k | 8m | 4f | 7b | 8c | 6d |
| I-187 | 1e | 2e | 3b | 8m | 4f | 7b | 8e | 6a |
| I-188 | 1e | 2e | 3e | 8m | 4f | 7b | 8e | 6a |
| I-189 | 1e | 2e | 3k | 8m | 4f | 7b | 8e | 6a |
| I-190 | 1e | 2e | 3b | 8m | 4f | 7b | 8e | 6d |
| I-191 | 1e | 2e | 3e | 8m | 4f | 7b | 8e | 6d |
| I-192 | 1e | 2e | 3k | 8m | 4f | 7b | 8e | 6d |
| I-193 | 1b | 2b | 3b | 8q | 4d | 7a | 8c | 6a |
| I-194 | 1b | 2b | 3e | 8q | 4d | 7a | 8c | 6a |
| I-195 | 1b | 2b | 3k | 8q | 4d | 7a | 8c | 6a |
| I-196 | 1b | 2b | 3b | 8q | 4d | 7a | 8c | 6d |
| I-197 | 1b | 2b | 3e | 8q | 4d | 7a | 8c | 6d |
| I-198 | 1b | 2b | 3k | 8q | 4d | 7a | 8c | 6d |
| I-199 | 1b | 2b | 3b | 8q | 4d | 7a | 8e | 6a |
| I-200 | 1b | 2b | 3e | 8q | 4d | 7a | 8e | 6a |
| I-201 | 1b | 2b | 3k | 8q | 4d | 7a | 8e | 6a |
| I-202 | 1b | 2b | 3b | 8q | 4d | 7a | 8e | 6d |
| I-203 | 1b | 2b | 3e | 8q | 4d | 7a | 8e | 6d |
| I-204 | 1b | 2b | 3k | 8q | 4d | 7a | 8e | 6d |
| I-205 | 1b | 2b | 3b | 8q | 4d | 7b | 8c | 6a |
| I-206 | 1b | 2b | 3e | 8q | 4d | 7b | 8c | 6a |
| I-207 | 1b | 2b | 3k | 8q | 4d | 7b | 8c | 6a |
| I-208 | 1b | 2b | 3b | 8q | 4d | 7b | 8c | 6d |
| I-209 | 1b | 2b | 3e | 8q | 4d | 7b | 8c | 6d |
| I-210 | 1b | 2b | 3k | 8q | 4d | 7b | 8c | 6d |
| I-211 | 1b | 2b | 3b | 8q | 4d | 7b | 8e | 6a |
| I-212 | 1b | 2b | 3e | 8q | 4d | 7b | 8e | 6a |
| I-213 | 1b | 2b | 3k | 8q | 4d | 7b | 8e | 6a |
| I-214 | 1b | 2b | 3b | 8q | 4d | 7b | 8e | 6d |
| I-215 | 1b | 2b | 3e | 8q | 4d | 7b | 8e | 6d |
| I-216 | 1b | 2b | 3k | 8q | 4d | 7b | 8e | 6d |
| I-217 | 1b | 2b | 3b | 8q | 4f | 7a | 8c | 6a |
| I-218 | 1b | 2b | 3e | 8q | 4f | 7a | 8c | 6a |
| I-219 | 1b | 2b | 3k | 8q | 4f | 7a | 8c | 6a |
| I-220 | 1b | 2b | 3b | 8q | 4f | 7a | 8c | 6d |
| I-221 | 1b | 2b | 3e | 8q | 4f | 7a | 8c | 6d |
| I-222 | 1b | 2b | 3k | 8q | 4f | 7a | 8c | 6d |
| I-223 | 1b | 2b | 3b | 8q | 4f | 7a | 8e | 6a |
| I-224 | 1b | 2b | 3e | 8q | 4f | 7a | 8e | 6a |
| I-225 | 1b | 2b | 3k | 8q | 4f | 7a | 8e | 6a |
| I-226 | 1b | 2b | 3b | 8q | 4f | 7a | 8e | 6d |
| I-227 | 1b | 2b | 3e | 8q | 4f | 7a | 8e | 6d |
| I-228 | 1b | 2b | 3k | 8q | 4f | 7a | 8e | 6d |
| I-229 | 1b | 2b | 3b | 8q | 4f | 7b | 8c | 6a |
| I-230 | 1b | 2b | 3e | 8q | 4f | 7b | 8c | 6a |
| I-231 | 1b | 2b | 3k | 8q | 4f | 7b | 8c | 6a |
| I-232 | 1b | 2b | 3b | 8q | 4f | 7b | 8c | 6d |
| I-233 | 1b | 2b | 3e | 8q | 4f | 7b | 8c | 6d |
| I-234 | 1b | 2b | 3k | 8q | 4f | 7b | 8c | 6d |
| I-235 | 1b | 2b | 3b | 8q | 4f | 7b | 8e | 6a |
| I-236 | 1b | 2b | 3e | 8q | 4f | 7b | 8e | 6a |
| I-237 | 1b | 2b | 3k | 8q | 4f | 7b | 8e | 6a |
| I-238 | 1b | 2b | 3b | 8q | 4f | 7b | 8e | 6d |
| I-239 | 1b | 2b | 3e | 8q | 4f | 7b | 8e | 6d |
| I-240 | 1b | 2b | 3k | 8q | 4f | 7b | 8e | 6d |
| I-241 | 1b | 2e | 3b | 8q | 4d | 7a | 8c | 6a |
| I-242 | 1b | 2e | 3e | 8q | 4d | 7a | 8c | 6a |
| I-243 | 1b | 2e | 3k | 8q | 4d | 7a | 8c | 6a |
| I-244 | 1b | 2e | 3b | 8q | 4d | 7a | 8c | 6d |
| I-245 | 1b | 2e | 3e | 8q | 4d | 7a | 8c | 6d |
| I-246 | 1b | 2e | 3k | 8q | 4d | 7a | 8c | 6d |
| I-247 | 1b | 2e | 3b | 8q | 4d | 7a | 8e | 6a |
| I-248 | 1b | 2e | 3e | 8q | 4d | 7a | 8e | 6a |
| I-249 | 1b | 2e | 3k | 8q | 4d | 7a | 8e | 6a |
| I-250 | 1b | 2e | 3b | 8q | 4d | 7a | 8e | 6d |
| I-251 | 1b | 2e | 3e | 8q | 4d | 7a | 8e | 6d |
| I-252 | 1b | 2e | 3k | 8q | 4d | 7a | 8e | 6d |
| I-253 | 1b | 2e | 3b | 8q | 4d | 7b | 8c | 6a |
| I-254 | 1b | 2e | 3e | 8q | 4d | 7b | 8c | 6a |
| I-255 | 1b | 2e | 3k | 8q | 4d | 7b | 8c | 6a |
| I-256 | 1b | 2e | 3b | 8q | 4d | 7b | 8c | 6d |
| I-257 | 1b | 2e | 3e | 8q | 4d | 7b | 8c | 6d |
| I-258 | 1b | 2e | 3k | 8q | 4d | 7b | 8c | 6d |
| I-259 | 1b | 2e | 3b | 8q | 4d | 7b | 8e | 6a |
| I-260 | 1b | 2e | 3e | 8q | 4d | 7b | 8e | 6a |
| I-261 | 1b | 2e | 3k | 8q | 4d | 7b | 8e | 6a |
| I-262 | 1b | 2e | 3b | 8q | 4d | 7b | 8e | 6d |
| I-263 | 1b | 2e | 3e | 8q | 4d | 7b | 8e | 6d |
| I-264 | 1b | 2e | 3k | 8q | 4d | 7b | 8e | 6d |
| I-265 | 1b | 2e | 3b | 8q | 4f | 7a | 8c | 6a |
| I-266 | 1b | 2e | 3e | 8q | 4f | 7a | 8c | 6a |
| I-267 | 1b | 2e | 3k | 8q | 4f | 7a | 8c | 6a |
| I-268 | 1b | 2e | 3b | 8q | 4f | 7a | 8c | 6d |
| I-269 | 1b | 2e | 3e | 8q | 4f | 7a | 8c | 6d |
| I-270 | 1b | 2e | 3k | 8q | 4f | 7a | 8c | 6d |
| I-271 | 1b | 2e | 3b | 8q | 4f | 7a | 8e | 6a |
| I-272 | 1b | 2e | 3e | 8q | 4f | 7a | 8e | 6a |
| I-273 | 1b | 2e | 3k | 8q | 4f | 7a | 8e | 6a |
| I-274 | 1b | 2e | 3b | 8q | 4f | 7a | 8e | 6d |
| I-275 | 1b | 2e | 3e | 8q | 4f | 7a | 8e | 6d |
| I-276 | 1b | 2e | 3k | 8q | 4f | 7a | 8e | 6d |
| I-277 | 1b | 2e | 3b | 8q | 4f | 7b | 8c | 6a |
| I-278 | 1b | 2e | 3e | 8q | 4f | 7b | 8c | 6a |
| I-279 | 1b | 2e | 3k | 8q | 4f | 7b | 8c | 6a |
| I-280 | 1b | 2e | 3b | 8q | 4f | 7b | 8c | 6d |
| I-281 | 1b | 2e | 3e | 8q | 4f | 7b | 8c | 6d |
| I-282 | 1b | 2e | 3k | 8q | 4f | 7b | 8c | 6d |
| I-283 | 1b | 2e | 3b | 8q | 4f | 7b | 8e | 6a |
| I-284 | 1b | 2e | 3e | 8q | 4f | 7b | 8e | 6a |
| I-285 | 1b | 2e | 3k | 8q | 4f | 7b | 8e | 6a |
| I-286 | 1b | 2e | 3b | 8q | 4f | 7b | 8e | 6d |
| I-287 | 1b | 2e | 3e | 8q | 4f | 7b | 8e | 6d |
| I-288 | 1b | 2e | 3k | 8q | 4f | 7b | 8e | 6d |
| I-289 | 1e | 2b | 3b | 8q | 4d | 7a | 8c | 6a |
| I-290 | 1e | 2b | 3e | 8q | 4d | 7a | 8c | 6a |
| I-291 | 1e | 2b | 3k | 8q | 4d | 7a | 8c | 6a |
| I-292 | 1e | 2b | 3b | 8q | 4d | 7a | 8c | 6d |
| I-293 | 1e | 2b | 3e | 8q | 4d | 7a | 8c | 6d |
| I-294 | 1e | 2b | 3k | 8q | 4d | 7a | 8c | 6d |
| I-295 | 1e | 2b | 3b | 8q | 4d | 7a | 8e | 6a |
| I-296 | 1e | 2b | 3e | 8q | 4d | 7a | 8e | 6a |
| I-297 | 1e | 2b | 3k | 8q | 4d | 7a | 8e | 6a |
| I-298 | 1e | 2b | 3b | 8q | 4d | 7a | 8e | 6d |
| I-299 | 1e | 2b | 3e | 8q | 4d | 7a | 8e | 6d |
| I-300 | 1e | 2b | 3k | 8q | 4d | 7a | 8e | 6d |
| I-301 | 1e | 2b | 3b | 8q | 4d | 7b | 8c | 6a |
| I-302 | 1e | 2b | 3e | 8q | 4d | 7b | 8c | 6a |
| I-303 | 1e | 2b | 3k | 8q | 4d | 7b | 8c | 6a |
| I-304 | 1e | 2b | 3b | 8q | 4d | 7b | 8c | 6d |
| I-305 | 1e | 2b | 3e | 8q | 4d | 7b | 8c | 6d |
| I-306 | 1e | 2b | 3k | 8q | 4d | 7b | 8c | 6d |
| I-307 | 1e | 2b | 3b | 8q | 4d | 7b | 8e | 6a |
| I-308 | 1e | 2b | 3e | 8q | 4d | 7b | 8e | 6a |
| I-309 | 1e | 2b | 3k | 8q | 4d | 7b | 8e | 6a |
| I-310 | 1e | 2b | 3b | 8q | 4d | 7b | 8e | 6d |
| I-311 | 1e | 2b | 3e | 8q | 4d | 7b | 8e | 6d |
| I-312 | 1e | 2b | 3k | 8q | 4d | 7b | 8e | 6d |
| I-313 | 1e | 2b | 3b | 8q | 4f | 7a | 8c | 6a |
| I-314 | 1e | 2b | 3e | 8q | 4f | 7a | 8c | 6a |
| I-315 | 1e | 2b | 3k | 8q | 4f | 7a | 8c | 6a |
| I-316 | 1e | 2b | 3b | 8q | 4f | 7a | 8c | 6d |
| I-317 | 1e | 2b | 3e | 8q | 4f | 7a | 8c | 6d |
| I-318 | 1e | 2b | 3k | 8q | 4f | 7a | 8c | 6d |
| I-319 | 1e | 2b | 3b | 8q | 4f | 7a | 8e | 6a |
| I-320 | 1e | 2b | 3e | 8q | 4f | 7a | 8e | 6a |
| I-321 | 1e | 2b | 3k | 8q | 4f | 7a | 8e | 6a |
| I-322 | 1e | 2b | 3b | 8q | 4f | 7a | 8e | 6d |
| I-323 | 1e | 2b | 3e | 8q | 4f | 7a | 8e | 6d |
| I-324 | 1e | 2b | 3k | 8q | 4f | 7a | 8e | 6d |
| I-325 | 1e | 2b | 3b | 8q | 4f | 7b | 8c | 6a |
| I-326 | 1e | 2b | 3e | 8q | 4f | 7b | 8c | 6a |
| I-327 | 1e | 2b | 3k | 8q | 4f | 7b | 8c | 6a |
| I-328 | 1e | 2b | 3b | 8q | 4f | 7b | 8c | 6d |

| Embodiment | R$^1$ | R$^2$ | R$^4$ | R$^6$ | R$^7$ | X & Y | m & n | M |
|---|---|---|---|---|---|---|---|---|
| I-329 | 1e | 2b | 3e | 8q | 4f | 7b | 8c | 6d |
| I-330 | 1e | 2b | 3k | 8q | 4f | 7b | 8c | 6d |
| I-331 | 1e | 2b | 3b | 8q | 4f | 7b | 8e | 6a |
| I-332 | 1e | 2b | 3e | 8q | 4f | 7b | 8e | 6a |
| I-333 | 1e | 2b | 3k | 8q | 4f | 7b | 8e | 6a |
| I-334 | 1e | 2b | 3b | 8q | 4f | 7b | 8e | 6d |
| I-335 | 1e | 2b | 3e | 8q | 4f | 7b | 8e | 6d |
| I-336 | 1e | 2b | 3k | 8q | 4f | 7b | 8e | 6d |
| I-337 | 1e | 2e | 3b | 8q | 4d | 7a | 8c | 6a |
| I-338 | 1e | 2e | 3e | 8q | 4d | 7a | 8c | 6a |
| I-339 | 1e | 2e | 3k | 8q | 4d | 7a | 8c | 6a |
| I-340 | 1e | 2e | 3b | 8q | 4d | 7a | 8c | 6d |
| I-341 | 1e | 2e | 3e | 8q | 4d | 7a | 8c | 6d |
| I-342 | 1e | 2e | 3k | 8q | 4d | 7a | 8c | 6d |
| I-343 | 1e | 2e | 3b | 8q | 4d | 7a | 8e | 6a |
| I-344 | 1e | 2e | 3e | 8q | 4d | 7a | 8e | 6a |
| I-345 | 1e | 2e | 3k | 8q | 4d | 7a | 8e | 6a |
| I-346 | 1e | 2e | 3b | 8q | 4d | 7a | 8e | 6d |
| I-347 | 1e | 2e | 3e | 8q | 4d | 7a | 8e | 6d |
| I-348 | 1e | 2e | 3k | 8q | 4d | 7a | 8e | 6d |
| I-349 | 1e | 2e | 3b | 8q | 4d | 7b | 8c | 6a |
| I-350 | 1e | 2e | 3e | 8q | 4d | 7b | 8c | 6a |
| I-351 | 1e | 2e | 3k | 8q | 4d | 7b | 8c | 6a |
| I-352 | 1e | 2e | 3b | 8q | 4d | 7b | 8c | 6d |
| I-353 | 1e | 2e | 3e | 8q | 4d | 7b | 8c | 6d |
| I-354 | 1e | 2e | 3k | 8q | 4d | 7b | 8c | 6d |
| I-355 | 1e | 2e | 3b | 8q | 4d | 7b | 8e | 6a |
| I-356 | 1e | 2e | 3e | 8q | 4d | 7b | 8e | 6a |
| I-357 | 1e | 2e | 3k | 8q | 4d | 7b | 8e | 6a |
| I-358 | 1e | 2e | 3b | 8q | 4d | 7b | 8e | 6d |
| I-359 | 1e | 2e | 3e | 8q | 4d | 7b | 8e | 6d |
| I-360 | 1e | 2e | 3k | 8q | 4d | 7b | 8e | 6d |
| I-361 | 1e | 2e | 3b | 8q | 4f | 7a | 8c | 6a |
| I-362 | 1e | 2e | 3e | 8q | 4f | 7a | 8c | 6a |
| I-363 | 1e | 2e | 3k | 8q | 4f | 7a | 8c | 6a |
| I-364 | 1e | 2e | 3b | 8q | 4f | 7a | 8c | 6d |
| I-365 | 1e | 2e | 3e | 8q | 4f | 7a | 8c | 6d |
| I-366 | 1e | 2e | 3k | 8q | 4f | 7a | 8c | 6d |
| I-367 | 1e | 2e | 3b | 8q | 4f | 7a | 8e | 6a |
| I-368 | 1e | 2e | 3e | 8q | 4f | 7a | 8e | 6a |
| I-369 | 1e | 2e | 3k | 8q | 4f | 7a | 8e | 6a |
| I-370 | 1e | 2e | 3b | 8q | 4f | 7a | 8e | 6d |
| I-371 | 1e | 2e | 3e | 8q | 4f | 7a | 8e | 6d |
| I-372 | 1e | 2e | 3k | 8q | 4f | 7a | 8e | 6d |
| I-373 | 1e | 2e | 3b | 8q | 4f | 7b | 8c | 6a |
| I-374 | 1e | 2e | 3e | 8q | 4f | 7b | 8c | 6a |
| I-375 | 1e | 2e | 3k | 8q | 4f | 7b | 8c | 6a |
| I-376 | 1e | 2e | 3b | 8q | 4f | 7b | 8c | 6d |
| I-377 | 1e | 2e | 3e | 8q | 4f | 7b | 8c | 6d |
| I-378 | 1e | 2e | 3k | 8q | 4f | 7b | 8c | 6d |
| I-379 | 1e | 2e | 3b | 8q | 4f | 7b | 8e | 6a |
| I-380 | 1e | 2e | 3e | 8q | 4f | 7b | 8e | 6a |
| I-381 | 1e | 2e | 3k | 8q | 4f | 7b | 8e | 6a |
| I-382 | 1e | 2e | 3b | 8q | 4f | 7b | 8e | 6d |
| I-383 | 1e | 2e | 3e | 8q | 4f | 7b | 8e | 6d |
| I-384 | 1e | 2e | 3k | 8q | 4f | 7b | 8e | 6d |

In embodiment (2) of the first aspect, the invention comprises the compound of formula (II), or any one of formulae (IIa)-(IIe),

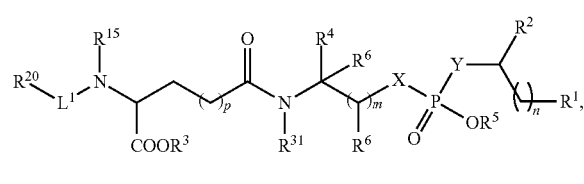

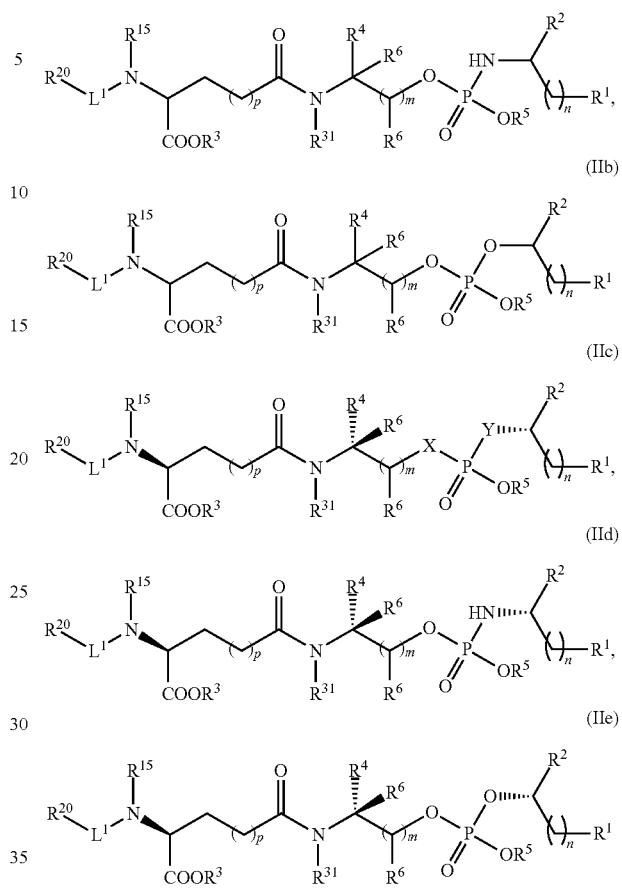

and pharmaceutically acceptable salts thereof, wherein p is 0 or 1; $R^{20}$ is —$C_1$-$C_7$alkyl-$R^9$, aryl-$R^9$, -aryl($C_1$-$C_7$)alkyl-$R^9$, or -heteroaryl-$R^9$, and m, n, X, Y, $L^1$, $R^1$-$R^6$, $R^9$, $R^{15}$, and $R^{31}$ are as defined for formula (I).

The invention further comprises subgenera of embodiment (2) of the first aspect in which the substituents are selected as any and all combinations of m, n, $L^1$, $R^1$, $R^2$, $R^4$, $R^5$, $R^6$, $R^{15}$, $R^{20}$, $R^{31}$, X, and Y as defined herein, including without limitation, the following:

$R^1$ is one of groups (1a)-(1l) as defined above for formula (I).

$R^2$ is one of groups (2a)-(2j) as defined above for formula (I).

$R^4$ is one of groups (3a)-(3k) as defined above for formula (I).

$R^5$ is one of groups (8h)-(8l) as defined above for formula (I).

each $R^6$ is independently one of groups (8m)-(8q) as defined above for formula (I).

$L^1$ is one of groups (5v)-(5z) as defined above for formula (I).

X and Y are one of groups (7a)-(7g) as defined above for formula (I).

m and n are one of groups (8a)-(8g) as defined above for formula (I).

each $R^3$ is independently one of the following groups (9a)-(9e):

(9a) hydrogen, —$C_1$-$C_7$ alkyl, —$C_1$-$C_7$ alkylaryl, or —$C_1$-$C_7$ alkylheteroaryl.

(9b) hydrogen, methyl, ethyl, t-butyl, or benzyl.
(9c) benzyl.
(9d) hydrogen or benzyl.
(9e) hydrogen.

$R^{15}$ and $R^{31}$ are each independently one of the following groups (10a)-(10e):
(10a) hydrogen, —$C_1$-$C_7$ alkyl, or benzyl.
(10b) hydrogen or —$C_1$-$C_7$ alkyl.
(10c) hydrogen or methyl.
(10d) hydrogen.
(10e) methyl $R^{20}$ is one of the following groups (11a)-(11gg):
(11a) $R^{20}$ is —$C_1$-$C_1$alkyl-$R^9$, -aryl($C_1$-$C_7$) alkyl-$R^9$, or -heteroaryl-$R^9$.
(11b) $R^{20}$ is —$C_1$-$C_7$alkyl-$R^9$ or -aryl($C_1$-$C_7$) alkyl-$R^9$.
(11c) $R^{20}$ is -heteroaryl-$R^9$.
(11d) $R^{20}$ is -pyridyl-$R^9$.
(11e) $R^{20}$ is -pyrimidinyl-$R^9$.
(11f) $R^{20}$ is —$C_1$-$C_7$alkyl-$R^9$.
(11g) $R^{20}$ is —$C_1$-$C_7$alkyl-$R^9$, -aryl($C_1$-$C_7$) alkyl-$R^9$, or -heteroaryl-$R^9$.
(11h) $R^{20}$ is —$C_1$-$C_7$alkyl-$R^9$.
(11i) $R^{20}$ is selected from the group consisting of,

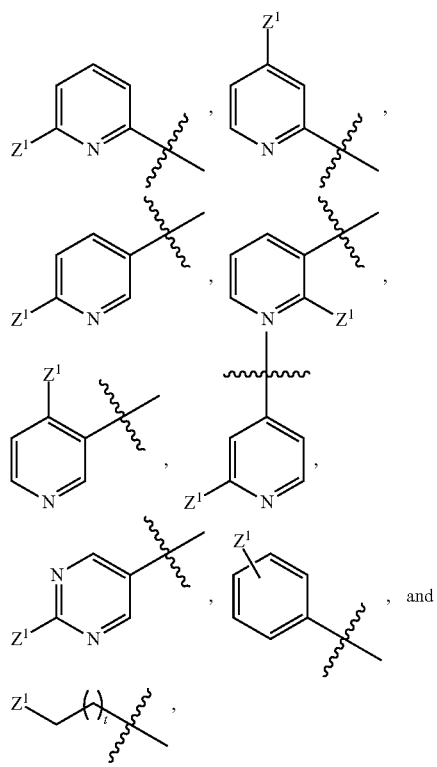

wherein $Z^1$ is a fluoro cold standard and t is 0, 1, 2, 3, 4, or 5.

(11j) $R^{20}$ is selected from the group consisting of,

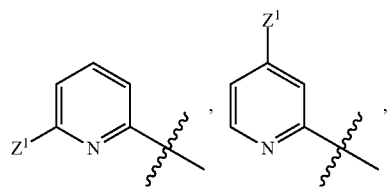

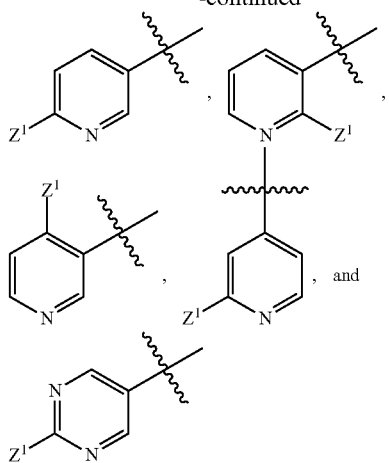

wherein $Z^1$ is a fluoro cold standard.

(11k) $R^{20}$ is selected from the group consisting of,

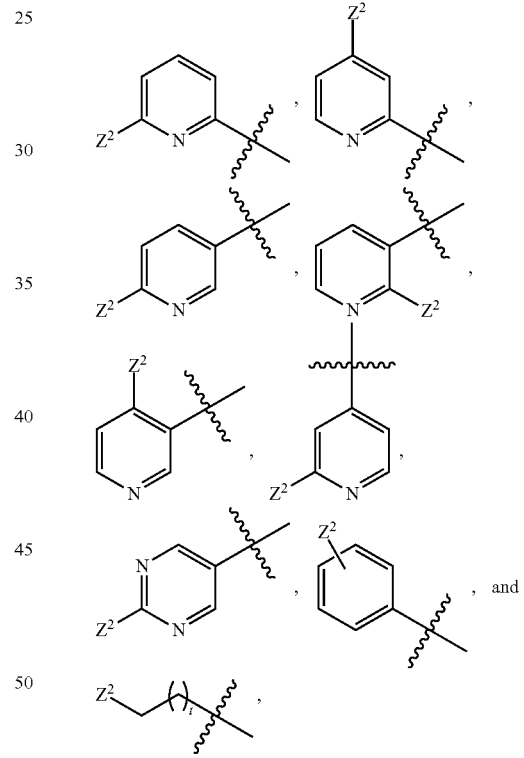

wherein $Z^2$ is fluoro cold standard.

(11l) $R^{20}$ is selected from the group consisting of, (11m)

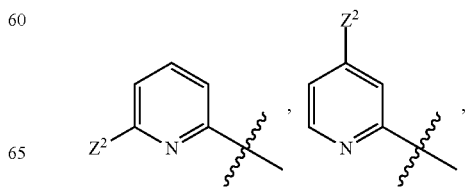

-continued
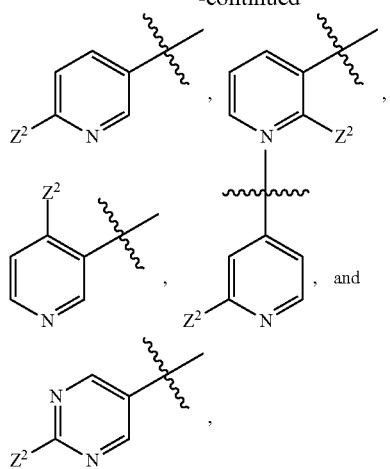
wherein $Z^2$ is a fluoro cold standard. $R^{20}$ is selected from the group consisting of,
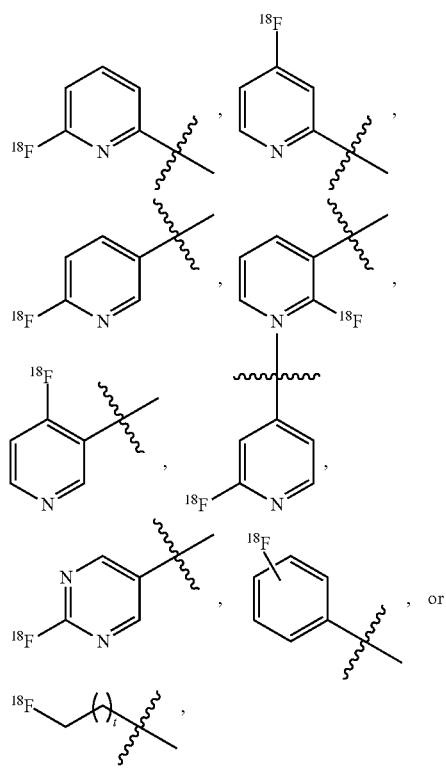
wherein t is 0, 1, 2, 3, 4, or 5.
(11n) $R^{20}$ is selected from the group consisting of,
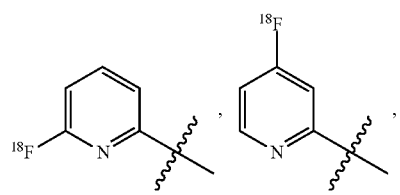
-continued
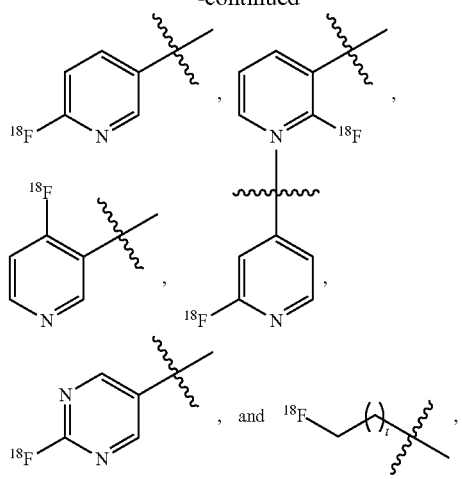
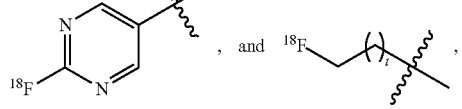
wherein t is 0, 1, 2, 3, 4, or 5.
(11o) $R^{20}$ is selected from the group consisting of,
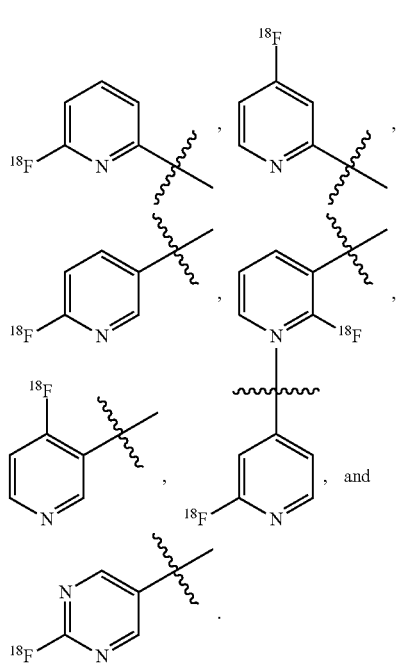
(11p) $R^{20}$ is selected from the group consisting of,
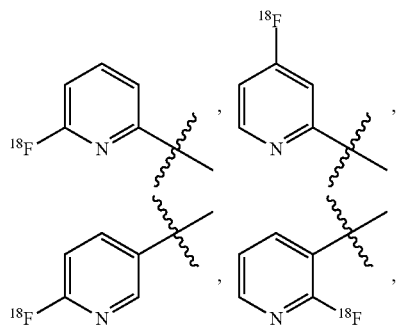

-continued

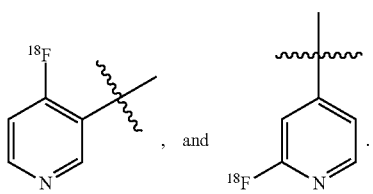, and (11q) R²⁰ is

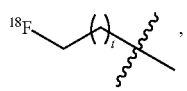, wherein t is 0, 1, 2, 3, 4, or 5.

(11r) R²⁰ is

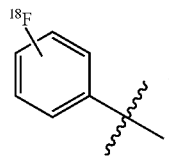.

(11s) R²⁰ is

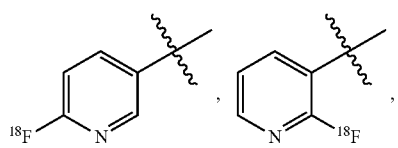,

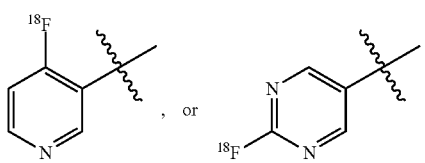, or (11t) R²⁰ is

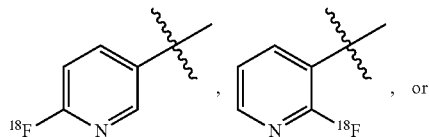, or

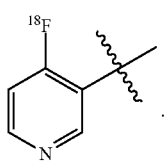.

(11u) R²⁰ is

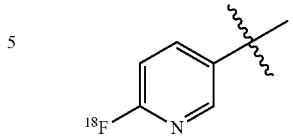.

(11v) R²⁰ is

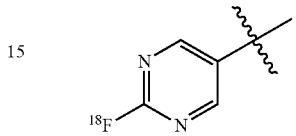.

Particular embodiments of this aspect of the invention include compounds of any one of formulae (II) and (IIa)-(IIc) wherein are defined in each of the following rows, wherein each entry is a group number as defined above:

| Embodiment | R¹, R², R⁴, R⁵ | R³ | R⁶ | L¹ | R²⁰ | R³¹ |
|---|---|---|---|---|---|---|
| II-1 | 1b, 2b, 3b, 8h | 9a | 8m | 5v | 11a | 10c |
| II-2 | 1b, 2b, 3b, 8h | 9a | 8m | 5v | 11b | 10c |
| II-3 | 1b, 2b, 3b, 8h | 9a | 8m | 5v | 11c | 10c |
| II-4 | 1b, 2b, 3b, 8h | 9a | 8m | 5v | 11d | 10c |
| II-5 | 1b, 2b, 3b, 8h | 9a | 8m | 5v | 11e | 10c |
| II-6 | 1b, 2b, 3b, 8h | 9a | 8m | 5v | 11f | 10c |
| II-7 | 1b, 2b, 3b, 8h | 9a | 8m | 5v | 11g | 10c |
| II-8 | 1b, 2b, 3b, 8h | 9a | 8m | 5v | 11h | 10c |
| II-9 | 1b, 2b, 3b, 8h | 9a | 8m | 5v | 11i | 10c |
| II-10 | 1b, 2b, 3b, 8h | 9a | 8m | 5v | 11j | 10c |
| II-11 | 1b, 2b, 3b, 8h | 9a | 8m | 5v | 11k | 10c |
| II-12 | 1b, 2b, 3b, 8h | 9a | 8m | 5v | 11l | 10c |
| II-13 | 1b, 2b, 3b, 8h | 9a | 8m | 5v | 11m | 10c |
| II-14 | 1b, 2b, 3b, 8h | 9a | 8m | 5v | 11n | 10c |
| II-15 | 1b, 2b, 3b, 8h | 9a | 8m | 5v | 11o | 10c |
| II-16 | 1b, 2b, 3b, 8h | 9a | 8m | 5v | 11p | 10c |
| II-17 | 1b, 2b, 3b, 8h | 9a | 8m | 5v | 11q | 10c |
| II-18 | 1b, 2b, 3b, 8h | 9a | 8m | 5v | 11r | 10c |
| II-19 | 1b, 2b, 3b, 8h | 9a | 8m | 5v | 11s | 10c |
| II-20 | 1b, 2b, 3b, 8h | 9a | 8m | 5v | 11t | 10c |
| II-21 | 1b, 2b, 3b, 8h | 9a | 8m | 5v | 11u | 10c |
| II-22 | 1b, 2b, 3b, 8h | 9a | 8m | 5v | 11v | 10c |
| II-23 | 1b, 2b, 3b, 8h | 9a | 8m | 5v | 11w | 10c |
| II-24 | 1b, 2b, 3b, 8h | 9a | 8m | 5v | 11x | 10c |
| II-25 | 1b, 2b, 3b, 8h | 9a | 8m | 5v | 11y | 10c |
| II-26 | 1b, 2b, 3b, 8h | 9a | 8m | 5v | 11z | 10c |
| II-27 | 1b, 2b, 3b, 8h | 9a | 8m | 5v | 11aa | 10c |
| II-28 | 1b, 2b, 3b, 8h | 9a | 8m | 5v | 11bb | 10c |
| II-29 | 1b, 2b, 3b, 8h | 9a | 8m | 5v | 11cc | 10c |
| II-30 | 1b, 2b, 3b, 8h | 9a | 8m | 5v | 11dd | 10c |
| II-31 | 1b, 2b, 3b, 8h | 9a | 8m | 5v | 11ee | 10c |
| II-32 | 1b, 2b, 3b, 8h | 9a | 8m | 5v | 11ff | 10c |
| II-33 | 1b, 2b, 3b, 8h | 9a | 8m | 5v | 11gg | 10c |
| II-34 | 1b, 2b, 3b, 8h | 9a | 8q | 5v | 11a | 10c |
| II-35 | 1b, 2b, 3b, 8h | 9a | 8q | 5v | 11b | 10c |
| II-36 | 1b, 2b, 3b, 8h | 9a | 8q | 5v | 11c | 10c |
| II-37 | 1b, 2b, 3b, 8h | 9a | 8q | 5v | 11d | 10c |
| II-38 | 1b, 2b, 3b, 8h | 9a | 8q | 5v | 11e | 10c |
| II-39 | 1b, 2b, 3b, 8h | 9a | 8q | 5v | 11f | 10c |
| II-40 | 1b, 2b, 3b, 8h | 9a | 8q | 5v | 11g | 10c |
| II-41 | 1b, 2b, 3b, 8h | 9a | 8q | 5v | 11h | 10c |
| II-42 | 1b, 2b, 3b, 8h | 9a | 8q | 5v | 11i | 10c |
| II-43 | 1b, 2b, 3b, 8h | 9a | 8q | 5v | 11j | 10c |
| II-44 | 1b, 2b, 3b, 8h | 9a | 8q | 5v | 11k | 10c |
| II-45 | 1b, 2b, 3b, 8h | 9a | 8q | 5v | 11l | 10c |
| II-46 | 1b, 2b, 3b, 8h | 9a | 8q | 5v | 11m | 10c |
| II-47 | 1b, 2b, 3b, 8h | 9a | 8q | 5v | 11n | 10c |
| II-48 | 1b, 2b, 3b, 8h | 9a | 8q | 5v | 11o | 10c |
| II-49 | 1b, 2b, 3b, 8h | 9a | 8q | 5v | 11p | 10c |

-continued

| Embodiment | R¹, R², R⁴, R⁵ | R³ | R⁶ | L¹ | R²⁰ | R³¹ |
|---|---|---|---|---|---|---|
| II-50 | 1b, 2b, 3b, 8h | 9a | 8q | 5v | 11q | 10c |
| II-51 | 1b, 2b, 3b, 8h | 9a | 8q | 5v | 11r | 10c |
| II-52 | 1b, 2b, 3b, 8h | 9a | 8q | 5v | 11s | 10c |
| II-53 | 1b, 2b, 3b, 8h | 9a | 8q | 5v | 11t | 10c |
| II-54 | 1b, 2b, 3b, 8h | 9a | 8q | 5v | 11u | 10c |
| II-55 | 1b, 2b, 3b, 8h | 9a | 8q | 5v | 11v | 10c |
| II-56 | 1b, 2b, 3b, 8h | 9a | 8q | 5v | 11w | 10c |
| II-57 | 1b, 2b, 3b, 8h | 9a | 8q | 5v | 11x | 10c |
| II-58 | 1b, 2b, 3b, 8h | 9a | 8q | 5v | 11y | 10c |
| II-59 | 1b, 2b, 3b, 8h | 9a | 8q | 5v | 11z | 10c |
| II-60 | 1b, 2b, 3b, 8h | 9a | 8q | 5v | 11aa | 10c |
| II-61 | 1b, 2b, 3b, 8h | 9a | 8q | 5v | 11bb | 10c |
| II-62 | 1b, 2b, 3b, 8h | 9a | 8q | 5v | 11cc | 10c |
| II-63 | 1b, 2b, 3b, 8h | 9a | 8q | 5v | 11dd | 10c |
| II-64 | 1b, 2b, 3b, 8h | 9a | 8q | 5v | 11ee | 10c |
| II-65 | 1b, 2b, 3b, 8h | 9a | 8q | 5v | 11ff | 10c |
| II-66 | 1b, 2b, 3b, 8h | 9a | 8q | 5v | 11gg | 10c |
| II-67 | 1b, 2b, 3b, 8h | 9d | 8m | 5v | 11a | 10c |
| II-68 | 1b, 2b, 3b, 8h | 9d | 8m | 5v | 11b | 10c |
| II-69 | 1b, 2b, 3b, 8h | 9d | 8m | 5v | 11c | 10c |
| II-70 | 1b, 2b, 3b, 8h | 9d | 8m | 5v | 11d | 10c |
| II-71 | 1b, 2b, 3b, 8h | 9d | 8m | 5v | 11e | 10c |
| II-72 | 1b, 2b, 3b, 8h | 9d | 8m | 5v | 11f | 10c |
| II-73 | 1b, 2b, 3b, 8h | 9d | 8m | 5v | 11g | 10c |
| II-74 | 1b, 2b, 3b, 8h | 9d | 8m | 5v | 11h | 10c |
| II-75 | 1b, 2b, 3b, 8h | 9d | 8m | 5v | 11i | 10c |
| II-76 | 1b, 2b, 3b, 8h | 9d | 8m | 5v | 11j | 10c |
| II-77 | 1b, 2b, 3b, 8h | 9d | 8m | 5v | 11k | 10c |
| II-78 | 1b, 2b, 3b, 8h | 9d | 8m | 5v | 11l | 10c |
| II-79 | 1b, 2b, 3b, 8h | 9d | 8m | 5v | 11m | 10c |
| II-80 | 1b, 2b, 3b, 8h | 9d | 8m | 5v | 11n | 10c |
| II-81 | 1b, 2b, 3b, 8h | 9d | 8m | 5v | 11o | 10c |
| II-82 | 1b, 2b, 3b, 8h | 9d | 8m | 5v | 11p | 10c |
| II-83 | 1b, 2b, 3b, 8h | 9d | 8m | 5v | 11q | 10c |
| II-84 | 1b, 2b, 3b, 8h | 9d | 8m | 5v | 11r | 10c |
| II-85 | 1b, 2b, 3b, 8h | 9d | 8m | 5v | 11s | 10c |
| II-86 | 1b, 2b, 3b, 8h | 9d | 8m | 5v | 11t | 10c |
| II-87 | 1b, 2b, 3b, 8h | 9d | 8m | 5v | 11u | 10c |
| II-88 | 1b, 2b, 3b, 8h | 9d | 8m | 5v | 11v | 10c |
| II-89 | 1b, 2b, 3b, 8h | 9d | 8m | 5v | 11w | 10c |
| II-90 | 1b, 2b, 3b, 8h | 9d | 8m | 5v | 11x | 10c |
| II-91 | 1b, 2b, 3b, 8h | 9d | 8m | 5v | 11y | 10c |
| II-92 | 1b, 2b, 3b, 8h | 9d | 8m | 5v | 11z | 10c |
| II-93 | 1b, 2b, 3b, 8h | 9d | 8m | 5v | 11aa | 10c |
| II-94 | 1b, 2b, 3b, 8h | 9d | 8m | 5v | 11bb | 10c |
| II-95 | 1b, 2b, 3b, 8h | 9d | 8m | 5v | 11cc | 10c |
| II-96 | 1b, 2b, 3b, 8h | 9d | 8m | 5v | 11dd | 10c |
| II-97 | 1b, 2b, 3b, 8h | 9d | 8m | 5v | 11ee | 10c |
| II-98 | 1b, 2b, 3b, 8h | 9d | 8m | 5v | 11ff | 10c |
| II-99 | 1b, 2b, 3b, 8h | 9d | 8m | 5v | 11gg | 10c |
| II-100 | 1b, 2b, 3b, 8h | 9d | 8q | 5v | 11a | 10c |
| II-101 | 1b, 2b, 3b, 8h | 9d | 8q | 5v | 11b | 10c |
| II-102 | 1b, 2b, 3b, 8h | 9d | 8q | 5v | 11c | 10c |
| II-103 | 1b, 2b, 3b, 8h | 9d | 8q | 5v | 11d | 10c |
| II-104 | 1b, 2b, 3b, 8h | 9d | 8q | 5v | 11e | 10c |
| II-105 | 1b, 2b, 3b, 8h | 9d | 8q | 5v | 11f | 10c |
| II-106 | 1b, 2b, 3b, 8h | 9d | 8q | 5v | 11g | 10c |
| II-107 | 1b, 2b, 3b, 8h | 9d | 8q | 5v | 11h | 10c |
| II-108 | 1b, 2b, 3b, 8h | 9d | 8q | 5v | 11i | 10c |
| II-109 | 1b, 2b, 3b, 8h | 9d | 8q | 5v | 11j | 10c |
| II-110 | 1b, 2b, 3b, 8h | 9d | 8q | 5v | 11k | 10c |
| II-111 | 1b, 2b, 3b, 8h | 9d | 8q | 5v | 11l | 10c |
| II-112 | 1b, 2b, 3b, 8h | 9d | 8q | 5v | 11m | 10c |
| II-113 | 1b, 2b, 3b, 8h | 9d | 8q | 5v | 11n | 10c |
| II-114 | 1b, 2b, 3b, 8h | 9d | 8q | 5v | 11o | 10c |
| II-115 | 1b, 2b, 3b, 8h | 9d | 8q | 5v | 11p | 10c |
| II-116 | 1b, 2b, 3b, 8h | 9d | 8q | 5v | 11q | 10c |
| II-117 | 1b, 2b, 3b, 8h | 9d | 8q | 5v | 11r | 10c |
| II-118 | 1b, 2b, 3b, 8h | 9d | 8q | 5v | 11s | 10c |
| II-119 | 1b, 2b, 3b, 8h | 9d | 8q | 5v | 11t | 10c |
| II-120 | 1b, 2b, 3b, 8h | 9d | 8q | 5v | 11u | 10c |
| II-121 | 1b, 2b, 3b, 8h | 9d | 8q | 5v | 11v | 10c |
| II-122 | 1b, 2b, 3b, 8h | 9d | 8q | 5v | 11w | 10c |
| II-123 | 1b, 2b, 3b, 8h | 9d | 8q | 5v | 11x | 10c |
| II-124 | 1b, 2b, 3b, 8h | 9d | 8q | 5v | 11y | 10c |
| II-125 | 1b, 2b, 3b, 8h | 9d | 8q | 5v | 11z | 10c |
| II-126 | 1b, 2b, 3b, 8h | 9d | 8q | 5v | 11aa | 10c |
| II-127 | 1b, 2b, 3b, 8h | 9d | 8q | 5v | 11bb | 10c |
| II-128 | 1b, 2b, 3b, 8h | 9d | 8q | 5v | 11cc | 10c |
| II-129 | 1b, 2b, 3b, 8h | 9d | 8q | 5v | 11dd | 10c |
| II-130 | 1b, 2b, 3b, 8h | 9d | 8q | 5v | 11ee | 10c |
| II-131 | 1b, 2b, 3b, 8h | 9d | 8q | 5v | 11ff | 10c |
| II-132 | 1b, 2b, 3b, 8h | 9d | 8q | 5v | 11gg | 10c |
| II-133 | 1e, 2e, 3e, 8k | 9a | 8m | 5v | 11a | 10c |
| II-134 | 1e, 2e, 3e, 8k | 9a | 8m | 5v | 11b | 10c |
| II-135 | 1e, 2e, 3e, 8k | 9a | 8m | 5v | 11c | 10c |
| II-136 | 1e, 2e, 3e, 8k | 9a | 8m | 5v | 11d | 10c |
| II-137 | 1e, 2e, 3e, 8k | 9a | 8m | 5v | 11e | 10c |
| II-138 | 1e, 2e, 3e, 8k | 9a | 8m | 5v | 11f | 10c |
| II-139 | 1e, 2e, 3e, 8k | 9a | 8m | 5v | 11g | 10c |
| II-140 | 1e, 2e, 3e, 8k | 9a | 8m | 5v | 11h | 10c |
| II-141 | 1e, 2e, 3e, 8k | 9a | 8m | 5v | 11i | 10c |
| II-142 | 1e, 2e, 3e, 8k | 9a | 8m | 5v | 11j | 10c |
| II-143 | 1e, 2e, 3e, 8k | 9a | 8m | 5v | 11k | 10c |
| II-144 | 1e, 2e, 3e, 8k | 9a | 8m | 5v | 11l | 10c |
| II-145 | 1e, 2e, 3e, 8k | 9a | 8m | 5v | 11m | 10c |
| II-146 | 1e, 2e, 3e, 8k | 9a | 8m | 5v | 11n | 10c |
| II-147 | 1e, 2e, 3e, 8k | 9a | 8m | 5v | 11o | 10c |
| II-148 | 1e, 2e, 3e, 8k | 9a | 8m | 5v | 11p | 10c |
| II-149 | 1e, 2e, 3e, 8k | 9a | 8m | 5v | 11q | 10c |
| II-150 | 1e, 2e, 3e, 8k | 9a | 8m | 5v | 11r | 10c |
| II-151 | 1e, 2e, 3e, 8k | 9a | 8m | 5v | 11s | 10c |
| II-152 | 1e, 2e, 3e, 8k | 9a | 8m | 5v | 11t | 10c |
| II-153 | 1e, 2e, 3e, 8k | 9a | 8m | 5v | 11u | 10c |
| II-154 | 1e, 2e, 3e, 8k | 9a | 8m | 5v | 11v | 10c |
| II-155 | 1e, 2e, 3e, 8k | 9a | 8m | 5v | 11w | 10c |
| II-156 | 1e, 2e, 3e, 8k | 9a | 8m | 5v | 11x | 10c |
| II-157 | 1e, 2e, 3e, 8k | 9a | 8m | 5v | 11y | 10c |
| II-158 | 1e, 2e, 3e, 8k | 9a | 8m | 5v | 11z | 10c |
| II-159 | 1e, 2e, 3e, 8k | 9a | 8m | 5v | 11aa | 10c |
| II-160 | 1e, 2e, 3e, 8k | 9a | 8m | 5v | 11bb | 10c |
| II-161 | 1e, 2e, 3e, 8k | 9a | 8m | 5v | 11cc | 10c |
| II-162 | 1e, 2e, 3e, 8k | 9a | 8m | 5v | 11dd | 10c |
| II-163 | 1e, 2e, 3e, 8k | 9a | 8m | 5v | 11ee | 10c |
| II-164 | 1e, 2e, 3e, 8k | 9a | 8m | 5v | 11ff | 10c |
| II-165 | 1e, 2e, 3e, 8k | 9a | 8m | 5v | 11gg | 10c |
| II-166 | 1e, 2e, 3e, 8k | 9a | 8q | 5v | 11a | 10c |
| II-167 | 1e, 2e, 3e, 8k | 9a | 8q | 5v | 11b | 10c |
| II-168 | 1e, 2e, 3e, 8k | 9a | 8q | 5v | 11c | 10c |
| II-169 | 1e, 2e, 3e, 8k | 9a | 8q | 5v | 11d | 10c |
| II-170 | 1e, 2e, 3e, 8k | 9a | 8q | 5v | 11e | 10c |
| II-171 | 1e, 2e, 3e, 8k | 9a | 8q | 5v | 11f | 10c |
| II-172 | 1e, 2e, 3e, 8k | 9a | 8q | 5v | 11g | 10c |
| II-173 | 1e, 2e, 3e, 8k | 9a | 8q | 5v | 11h | 10c |
| II-174 | 1e, 2e, 3e, 8k | 9a | 8q | 5v | 11i | 10c |
| II-175 | 1e, 2e, 3e, 8k | 9a | 8q | 5v | 11j | 10c |
| II-176 | 1e, 2e, 3e, 8k | 9a | 8q | 5v | 11k | 10c |
| II-177 | 1e, 2e, 3e, 8k | 9a | 8q | 5v | 11l | 10c |
| II-178 | 1e, 2e, 3e, 8k | 9a | 8q | 5v | 11m | 10c |
| II-179 | 1e, 2e, 3e, 8k | 9a | 8q | 5v | 11n | 10c |
| II-180 | 1e, 2e, 3e, 8k | 9a | 8q | 5v | 11o | 10c |
| II-181 | 1e, 2e, 3e, 8k | 9a | 8q | 5v | 11p | 10c |
| II-182 | 1e, 2e, 3e, 8k | 9a | 8q | 5v | 11q | 10c |
| II-183 | 1e, 2e, 3e, 8k | 9a | 8q | 5v | 11r | 10c |
| II-184 | 1e, 2e, 3e, 8k | 9a | 8q | 5v | 11s | 10c |
| II-185 | 1e, 2e, 3e, 8k | 9a | 8q | 5v | 11t | 10c |
| II-186 | 1e, 2e, 3e, 8k | 9a | 8q | 5v | 11u | 10c |
| II-187 | 1e, 2e, 3e, 8k | 9a | 8q | 5v | 11v | 10c |
| II-188 | 1e, 2e, 3e, 8k | 9a | 8q | 5v | 11w | 10c |
| II-189 | 1e, 2e, 3e, 8k | 9a | 8q | 5v | 11x | 10c |
| II-190 | 1e, 2e, 3e, 8k | 9a | 8q | 5v | 11y | 10c |
| II-191 | 1e, 2e, 3e, 8k | 9a | 8q | 5v | 11z | 10c |
| II-192 | 1e, 2e, 3e, 8k | 9a | 8q | 5v | 11aa | 10c |
| II-193 | 1e, 2e, 3e, 8k | 9a | 8q | 5v | 11bb | 10c |
| II-194 | 1e, 2e, 3e, 8k | 9a | 8q | 5v | 11cc | 10c |
| II-195 | 1e, 2e, 3e, 8k | 9a | 8q | 5v | 11dd | 10c |
| II-196 | 1e, 2e, 3e, 8k | 9a | 8q | 5v | 11ee | 10c |
| II-197 | 1e, 2e, 3e, 8k | 9a | 8q | 5v | 11ff | 10c |
| II-198 | 1e, 2e, 3e, 8k | 9a | 8q | 5v | 11gg | 10c |
| II-199 | 1e, 2e, 3e, 8k | 9d | 8m | 5v | 11a | 10c |
| II-200 | 1e, 2e, 3e, 8k | 9d | 8m | 5v | 11b | 10c |
| II-201 | 1e, 2e, 3e, 8k | 9d | 8m | 5v | 11c | 10c |
| II-202 | 1e, 2e, 3e, 8k | 9d | 8m | 5v | 11d | 10c |
| II-203 | 1e, 2e, 3e, 8k | 9d | 8m | 5v | 11e | 10c |

-continued

| Embodiment | R¹, R², R⁴, R⁵ | R³ | R⁶ | L¹ | R²⁰ | R³¹ |
|---|---|---|---|---|---|---|
| II-204 | 1e, 2e, 3e, 8k | 9d | 8m | 5v | 11f | 10c |
| II-205 | 1e, 2e, 3e, 8k | 9d | 8m | 5v | 11g | 10c |
| II-206 | 1e, 2e, 3e, 8k | 9d | 8m | 5v | 11h | 10c |
| II-207 | 1e, 2e, 3e, 8k | 9d | 8m | 5v | 11i | 10c |
| II-208 | 1e, 2e, 3e, 8k | 9d | 8m | 5v | 11j | 10c |
| II-209 | 1e, 2e, 3e, 8k | 9d | 8m | 5v | 11k | 10c |
| II-210 | 1e, 2e, 3e, 8k | 9d | 8m | 5v | 11l | 10c |
| II-211 | 1e, 2e, 3e, 8k | 9d | 8m | 5v | 11m | 10c |
| II-212 | 1e, 2e, 3e, 8k | 9d | 8m | 5v | 11n | 10c |
| II-213 | 1e, 2e, 3e, 8k | 9d | 8m | 5v | 11o | 10c |
| II-214 | 1e, 2e, 3e, 8k | 9d | 8m | 5v | 11p | 10c |
| II-215 | 1e, 2e, 3e, 8k | 9d | 8m | 5v | 11q | 10c |
| II-216 | 1e, 2e, 3e, 8k | 9d | 8m | 5v | 11r | 10c |
| II-217 | 1e, 2e, 3e, 8k | 9d | 8m | 5v | 11s | 10c |
| II-218 | 1e, 2e, 3e, 8k | 9d | 8m | 5v | 11t | 10c |
| II-219 | 1e, 2e, 3e, 8k | 9d | 8m | 5v | 11u | 10c |
| II-220 | 1e, 2e, 3e, 8k | 9d | 8m | 5v | 11v | 10c |
| II-221 | 1e, 2e, 3e, 8k | 9d | 8m | 5v | 11w | 10c |
| II-222 | 1e, 2e, 3e, 8k | 9d | 8m | 5v | 11x | 10c |
| II-223 | 1e, 2e, 3e, 8k | 9d | 8m | 5v | 11y | 10c |
| II-224 | 1e, 2e, 3e, 8k | 9d | 8m | 5v | 11z | 10c |
| II-225 | 1e, 2e, 3e, 8k | 9d | 8m | 5v | 11aa | 10c |
| II-226 | 1e, 2e, 3e, 8k | 9d | 8m | 5v | 11bb | 10c |
| II-227 | 1e, 2e, 3e, 8k | 9d | 8m | 5v | 11cc | 10c |
| II-228 | 1e, 2e, 3e, 8k | 9d | 8m | 5v | 11dd | 10c |
| II-229 | 1e, 2e, 3e, 8k | 9d | 8m | 5v | 11ee | 10c |
| II-230 | 1e, 2e, 3e, 8k | 9d | 8m | 5v | 11ff | 10c |
| II-231 | 1e, 2e, 3e, 8k | 9d | 8m | 5v | 11gg | 10c |
| II-232 | 1e, 2e, 3e, 8k | 9d | 8q | 5v | 11a | 10c |
| II-233 | 1e, 2e, 3e, 8k | 9d | 8q | 5v | 11b | 10c |
| II-234 | 1e, 2e, 3e, 8k | 9d | 8q | 5v | 11c | 10c |
| II-235 | 1e, 2e, 3e, 8k | 9d | 8q | 5v | 11d | 10c |
| II-236 | 1e, 2e, 3e, 8k | 9d | 8q | 5v | 11e | 10c |
| II-237 | 1e, 2e, 3e, 8k | 9d | 8q | 5v | 11f | 10c |
| II-238 | 1e, 2e, 3e, 8k | 9d | 8q | 5v | 11g | 10c |
| II-239 | 1e, 2e, 3e, 8k | 9d | 8q | 5v | 11h | 10c |
| II-240 | 1e, 2e, 3e, 8k | 9d | 8q | 5v | 11i | 10c |
| II-241 | 1e, 2e, 3e, 8k | 9d | 8q | 5v | 11j | 10c |
| II-242 | 1e, 2e, 3e, 8k | 9d | 8q | 5v | 11k | 10c |
| II-243 | 1e, 2e, 3e, 8k | 9d | 8q | 5v | 11l | 10c |
| II-244 | 1e, 2e, 3e, 8k | 9d | 8q | 5v | 11m | 10c |
| II-245 | 1e, 2e, 3e, 8k | 9d | 8q | 5v | 11n | 10c |
| II-246 | 1e, 2e, 3e, 8k | 9d | 8q | 5v | 11o | 10c |
| II-247 | 1e, 2e, 3e, 8k | 9d | 8q | 5v | 11p | 10c |
| II-248 | 1e, 2e, 3e, 8k | 9d | 8q | 5v | 11q | 10c |
| II-249 | 1e, 2e, 3e, 8k | 9d | 8q | 5v | 11r | 10c |
| II-250 | 1e, 2e, 3e, 8k | 9d | 8q | 5v | 11s | 10c |
| II-251 | 1e, 2e, 3e, 8k | 9d | 8q | 5v | 11t | 10c |
| II-252 | 1e, 2e, 3e, 8k | 9d | 8q | 5v | 11u | 10c |
| II-253 | 1e, 2e, 3e, 8k | 9d | 8q | 5v | 11v | 10c |
| II-254 | 1e, 2e, 3e, 8k | 9d | 8q | 5v | 11w | 10c |
| II-255 | 1e, 2e, 3e, 8k | 9d | 8q | 5v | 11x | 10c |
| II-256 | 1e, 2e, 3e, 8k | 9d | 8q | 5v | 11y | 10c |
| II-257 | 1e, 2e, 3e, 8k | 9d | 8q | 5v | 11z | 10c |
| II-258 | 1e, 2e, 3e, 8k | 9d | 8q | 5v | 11aa | 10c |
| II-259 | 1e, 2e, 3e, 8k | 9d | 8q | 5v | 11bb | 10c |
| II-260 | 1e, 2e, 3e, 8k | 9d | 8q | 5v | 11cc | 10c |
| II-261 | 1e, 2e, 3e, 8k | 9d | 8q | 5v | 11dd | 10c |
| II-262 | 1e, 2e, 3e, 8k | 9d | 8q | 5v | 11ee | 10c |
| II-263 | 1e, 2e, 3e, 8k | 9d | 8q | 5v | 11ff | 10c |
| II-264 | 1e, 2e, 3e, 8k | 9d | 8q | 5v | 11gg | 10c |
| II-265 | 1b, 2b, 3b, 8h | 9a | 8m | 5y | 11a | 10c |
| II-266 | 1b, 2b, 3b, 8h | 9a | 8m | 5y | 11b | 10c |
| II-267 | 1b, 2b, 3b, 8h | 9a | 8m | 5y | 11c | 10c |
| II-268 | 1b, 2b, 3b, 8h | 9a | 8m | 5y | 11d | 10c |
| II-269 | 1b, 2b, 3b, 8h | 9a | 8m | 5y | 11e | 10c |
| II-270 | 1b, 2b, 3b, 8h | 9a | 8m | 5y | 11f | 10c |
| II-271 | 1b, 2b, 3b, 8h | 9a | 8m | 5y | 11g | 10c |
| II-272 | 1b, 2b, 3b, 8h | 9a | 8m | 5y | 11h | 10c |
| II-273 | 1b, 2b, 3b, 8h | 9a | 8m | 5y | 11i | 10c |
| II-274 | 1b, 2b, 3b, 8h | 9a | 8m | 5y | 11j | 10c |
| II-275 | 1b, 2b, 3b, 8h | 9a | 8m | 5y | 11k | 10c |
| II-276 | 1b, 2b, 3b, 8h | 9a | 8m | 5y | 11l | 10c |
| II-277 | 1b, 2b, 3b, 8h | 9a | 8m | 5y | 11m | 10c |
| II-278 | 1b, 2b, 3b, 8h | 9a | 8m | 5y | 11n | 10c |
| II-279 | 1b, 2b, 3b, 8h | 9a | 8m | 5y | 11o | 10c |
| II-280 | 1b, 2b, 3b, 8h | 9a | 8m | 5y | 11p | 10c |
| II-281 | 1b, 2b, 3b, 8h | 9a | 8m | 5y | 11q | 10c |
| II-282 | 1b, 2b, 3b, 8h | 9a | 8m | 5y | 11r | 10c |
| II-283 | 1b, 2b, 3b, 8h | 9a | 8m | 5y | 11s | 10c |
| II-284 | 1b, 2b, 3b, 8h | 9a | 8m | 5y | 11t | 10c |
| II-285 | 1b, 2b, 3b, 8h | 9a | 8m | 5y | 11u | 10c |
| II-286 | 1b, 2b, 3b, 8h | 9a | 8m | 5y | 11v | 10c |
| II-287 | 1b, 2b, 3b, 8h | 9a | 8m | 5y | 11w | 10c |
| II-288 | 1b, 2b, 3b, 8h | 9a | 8m | 5y | 11x | 10c |
| II-289 | 1b, 2b, 3b, 8h | 9a | 8m | 5y | 11y | 10c |
| II-290 | 1b, 2b, 3b, 8h | 9a | 8m | 5y | 11z | 10c |
| II-291 | 1b, 2b, 3b, 8h | 9a | 8m | 5y | 11aa | 10c |
| II-292 | 1b, 2b, 3b, 8h | 9a | 8m | 5y | 11bb | 10c |
| II-293 | 1b, 2b, 3b, 8h | 9a | 8m | 5y | 11cc | 10c |
| II-294 | 1b, 2b, 3b, 8h | 9a | 8m | 5y | 11dd | 10c |
| II-295 | 1b, 2b, 3b, 8h | 9a | 8m | 5y | 11ee | 10c |
| II-296 | 1b, 2b, 3b, 8h | 9a | 8m | 5y | 11ff | 10c |
| II-297 | 1b, 2b, 3b, 8h | 9a | 8m | 5y | 11gg | 10c |
| II-298 | 1b, 2b, 3b, 8h | 9a | 8q | 5y | 11a | 10c |
| II-299 | 1b, 2b, 3b, 8h | 9a | 8q | 5y | 11b | 10c |
| II-300 | 1b, 2b, 3b, 8h | 9a | 8q | 5y | 11c | 10c |
| II-301 | 1b, 2b, 3b, 8h | 9a | 8q | 5y | 11d | 10c |
| II-302 | 1b, 2b, 3b, 8h | 9a | 8q | 5y | 11e | 10c |
| II-303 | 1b, 2b, 3b, 8h | 9a | 8q | 5y | 11f | 10c |
| II-304 | 1b, 2b, 3b, 8h | 9a | 8q | 5y | 11g | 10c |
| II-305 | 1b, 2b, 3b, 8h | 9a | 8q | 5y | 11h | 10c |
| II-306 | 1b, 2b, 3b, 8h | 9a | 8q | 5y | 11i | 10c |
| II-307 | 1b, 2b, 3b, 8h | 9a | 8q | 5y | 11j | 10c |
| II-308 | 1b, 2b, 3b, 8h | 9a | 8q | 5y | 11k | 10c |
| II-309 | 1b, 2b, 3b, 8h | 9a | 8q | 5y | 11l | 10c |
| II-310 | 1b, 2b, 3b, 8h | 9a | 8q | 5y | 11m | 10c |
| II-311 | 1b, 2b, 3b, 8h | 9a | 8q | 5y | 11n | 10c |
| II-312 | 1b, 2b, 3b, 8h | 9a | 8q | 5y | 11o | 10c |
| II-313 | 1b. 2b, 3b, 8h | 9a | 8q | 5y | 11p | 10c |
| II-314 | 1b, 2b, 3b, 8h | 9a | 8q | 5y | 11q | 10c |
| II-315 | 1b, 2b, 3b, 8h | 9a | 8q | 5y | 11r | 10c |
| II-316 | 1b, 2b, 3b, 8h | 9a | 8q | 5y | 11s | 10c |
| II-317 | 1b, 2b, 3b, 8h | 9a | 8q | 5y | 11t | 10c |
| II-318 | 1b, 2b, 3b, 8h | 9a | 8q | 5y | 11u | 10c |
| II-319 | 1b, 2b, 3b, 8h | 9a | 8q | 5y | 11v | 10c |
| II-320 | 1b, 2b, 3b, 8h | 9a | 8q | 5y | 11w | 10c |
| II-321 | 1b, 2b, 3b, 8h | 9a | 8q | 5y | 11x | 10c |
| II-322 | 1b, 2b, 3b, 8h | 9a | 8q | 5y | 11y | 10c |
| II-323 | 1b, 2b, 3b, 8h | 9a | 8q | 5y | 11z | 10c |
| II-324 | 1b, 2b, 3b, 8h | 9a | 8q | 5y | 11aa | 10c |
| II-325 | 1b, 2b, 3b, 8h | 9a | 8q | 5y | 11bb | 10c |
| II-326 | 1b, 2b, 3b, 8h | 9a | 8q | 5y | 11cc | 10c |
| II-327 | 1b, 2b, 3b, 8h | 9a | 8q | 5y | 11dd | 10c |
| II-328 | 1b, 2b, 3b, 8h | 9a | 8q | 5y | 11ee | 10c |
| II-329 | 1b, 2b, 3b, 8h | 9a | 8q | 5y | 11ff | 10c |
| II-330 | 1b, 2b, 3b, 8h | 9a | 8q | 5y | 11gg | 10c |
| II-331 | 1b, 2b, 3b, 8h | 9d | 8m | 5y | 11a | 10c |
| II-332 | 1b, 2b, 3b, 8h | 9d | 8m | 5y | 11b | 10c |
| II-333 | 1b, 2b, 3b, 8h | 9d | 8m | 5y | 11c | 10c |
| II-334 | 1b, 2b, 3b, 8h | 9d | 8m | 5y | 11d | 10c |
| II-335 | 1b, 2b, 3b, 8h | 9d | 8m | 5y | 11e | 10c |
| II-336 | 1b, 2b, 3b, 8h | 9d | 8m | 5y | 11f | 10c |
| II-337 | 1b, 2b, 3b, 8h | 9d | 8m | 5y | 11g | 10c |
| II-338 | 1b, 2b, 3b, 8h | 9d | 8m | 5y | 11h | 10c |
| II-339 | 1b, 2b, 3b, 8h | 9d | 8m | 5y | 11i | 10c |
| II-340 | 1b, 2b, 3b, 8h | 9d | 8m | 5y | 11j | 10c |
| II-341 | 1b, 2b, 3b, 8h | 9d | 8m | 5y | 11k | 10c |
| II-342 | 1b, 2b, 3b, 8h | 9d | 8m | 5y | 11l | 10c |
| II-343 | 1b, 2b, 3b, 8h | 9d | 8m | 5y | 11m | 10c |
| II-344 | 1b, 2b, 3b, 8h | 9d | 8m | 5y | 11n | 10c |
| II-345 | 1b, 2b, 3b, 8h | 9d | 8m | 5y | 11o | 10c |
| II-346 | 1b, 2b, 3b, 8h | 9d | 8m | 5y | 11p | 10c |
| II-347 | 1b, 2b, 3b, 8h | 9d | 8m | 5y | 11q | 10c |
| II-348 | 1b, 2b, 3b, 8h | 9d | 8m | 5y | 11r | 10c |
| II-349 | 1b, 2b, 3b, 8h | 9d | 8m | 5y | 11s | 10c |
| II-350 | 1b, 2b, 3b, 8h | 9d | 8m | 5y | 11t | 10c |
| II-351 | 1b, 2b, 3b, 8h | 9d | 8m | 5y | 11u | 10c |
| II-352 | 1b, 2b, 3b, 8h | 9d | 8m | 5y | 11v | 10c |
| II-353 | 1b, 2b, 3b, 8h | 9d | 8m | 5y | 11w | 10c |
| II-354 | 1b, 2b, 3b, 8h | 9d | 8m | 5y | 11x | 10c |
| II-355 | 1b, 2b, 3b, 8h | 9d | 8m | 5y | 11y | 10c |
| II-356 | 1b, 2b, 3b, 8h | 9d | 8m | 5y | 11z | 10c |
| II-357 | 1b, 2b, 3b, 8h | 9d | 8m | 5y | 11aa | 10c |

| Embodiment | R¹, R², R⁴, R⁵ | R³ | R⁶ | L¹ | R²⁰ | R³¹ |
|---|---|---|---|---|---|---|
| II-358 | 1b, 2b, 3b, 8h | 9d | 8m | 5y | 11bb | 10c |
| II-359 | 1b, 2b, 3b, 8h | 9d | 8m | 5y | 11cc | 10c |
| II-360 | 1b, 2b, 3b, 8h | 9d | 8m | 5y | 11dd | 10c |
| II-361 | 1b, 2b, 3b, 8h | 9d | 8m | 5y | 11ee | 10c |
| II-362 | 1b, 2b, 3b, 8h | 9d | 8m | 5y | 11ff | 10c |
| II-363 | 1b, 2b, 3b, 8h | 9d | 8m | 5y | 11gg | 10c |
| II-364 | 1b, 2b, 3b, 8h | 9d | 8q | 5y | 11a | 10c |
| II-365 | 1b, 2b, 3b, 8h | 9d | 8q | 5y | 11b | 10c |
| II-366 | 1b, 2b, 3b, 8h | 9d | 8q | 5y | 11c | 10c |
| II-367 | 1b, 2b, 3b, 8h | 9d | 8q | 5y | 11d | 10c |
| II-368 | 1b, 2b, 3b, 8h | 9d | 8q | 5y | 11e | 10c |
| II-369 | 1b, 2b, 3b, 8h | 9d | 8q | 5y | 11f | 10c |
| II-370 | 1b, 2b, 3b, 8h | 9d | 8q | 5y | 11g | 10c |
| II-371 | 1b, 2b, 3b, 8h | 9d | 8q | 5y | 11h | 10c |
| II-372 | 1b, 2b, 3b, 8h | 9d | 8q | 5y | 11i | 10c |
| II-373 | 1b, 2b, 3b, 8h | 9d | 8q | 5y | 11j | 10c |
| II-374 | 1b, 2b, 3b, 8h | 9d | 8q | 5y | 11k | 10c |
| II-375 | 1b, 2b, 3b, 8h | 9d | 8q | 5y | 11l | 10c |
| II-376 | 1b, 2b, 3b, 8h | 9d | 8q | 5y | 11m | 10c |
| II-377 | 1b, 2b, 3b, 8h | 9d | 8q | 5y | 11n | 10c |
| II-378 | 1b, 2b, 3b, 8h | 9d | 8q | 5y | 11o | 10c |
| II-379 | 1b, 2b, 3b, 8h | 9d | 8q | 5y | 11p | 10c |
| II-380 | 1b, 2b, 3b, 8h | 9d | 8q | 5y | 11q | 10c |
| II-381 | 1b, 2b, 3b, 8h | 9d | 8q | 5y | 11r | 10c |
| II-382 | 1b, 2b, 3b, 8h | 9d | 8q | 5y | 11s | 10c |
| II-383 | 1b, 2b, 3b, 8h | 9d | 8q | 5y | 11t | 10c |
| II-384 | 1b, 2b, 3b, 8h | 9d | 8q | 5y | 11u | 10c |
| II-385 | 1b, 2b, 3b, 8h | 9d | 8q | 5y | 11v | 10c |
| II-386 | 1b, 2b, 3b, 8h | 9d | 8q | 5y | 11w | 10c |
| II-387 | 1b, 2b, 3b, 8h | 9d | 8q | 5y | 11x | 10c |
| II-388 | 1b, 2b, 3b, 8h | 9d | 8q | 5y | 11y | 10c |
| II-389 | 1b, 2b, 3b, 8h | 9d | 8q | 5y | 11z | 10c |
| II-390 | 1b, 2b, 3b, 8h | 9d | 8q | 5y | 11aa | 10c |
| II-391 | 1b, 2b, 3b, 8h | 9d | 8q | 5y | 11bb | 10c |
| II-392 | 1b, 2b, 3b, 8h | 9d | 8q | 5y | 11cc | 10c |
| II-393 | 1b, 2b, 3b, 8h | 9d | 8q | 5y | 11dd | 10c |
| II-394 | 1b, 2b, 3b, 8h | 9d | 8q | 5y | 11ee | 10c |
| II-395 | 1b, 2b, 3b, 8h | 9d | 8q | 5y | 11ff | 10c |
| II-396 | 1b, 2b, 3b, 8h | 9d | 8q | 5y | 11gg | 10c |
| II-397 | 1e, 2e, 3e, 8k | 9a | 8m | 5y | 11a | 10c |
| II-398 | 1e, 2e, 3e, 8k | 9a | 8m | 5y | 11b | 10c |
| II-399 | 1e, 2e, 3e, 8k | 9a | 8m | 5y | 11c | 10c |
| II-400 | 1e, 2e, 3e, 8k | 9a | 8m | 5y | 11d | 10c |
| II-401 | 1e, 2e, 3e, 8k | 9a | 8m | 5y | 11e | 10c |
| II-402 | 1e, 2e, 3e, 8k | 9a | 8m | 5y | 11f | 10c |
| II-403 | 1e, 2e, 3e, 8k | 9a | 8m | 5y | 11g | 10c |
| II-404 | 1e, 2e, 3e, 8k | 9a | 8m | 5y | 11h | 10c |
| II-405 | 1e, 2e, 3e, 8k | 9a | 8m | 5y | 11i | 10c |
| II-406 | 1e, 2e, 3e, 8k | 9a | 8m | 5y | 11j | 10c |
| II-407 | 1e, 2e, 3e, 8k | 9a | 8m | 5y | 11k | 10c |
| II-408 | 1e, 2e, 3e, 8k | 9a | 8m | 5y | 11l | 10c |
| II-409 | 1e, 2e, 3e, 8k | 9a | 8m | 5y | 11m | 10c |
| II-410 | 1e, 2e, 3e, 8k | 9a | 8m | 5y | 11n | 10c |
| II-411 | 1e, 2e, 3e, 8k | 9a | 8m | 5y | 11o | 10c |
| II-412 | 1e, 2e, 3e, 8k | 9a | 8m | 5y | 11p | 10c |
| II-413 | 1e, 2e, 3e, 8k | 9a | 8m | 5y | 11q | 10c |
| II-414 | 1e, 2e, 3e, 8k | 9a | 8m | 5y | 11r | 10c |
| II-415 | 1e, 2e, 3e, 8k | 9a | 8m | 5y | 11s | 10c |
| II-416 | 1e, 2e, 3e, 8k | 9a | 8m | 5y | 11t | 10c |
| II-417 | 1e, 2e, 3e, 8k | 9a | 8m | 5y | 11u | 10c |
| II-418 | 1e, 2e, 3e, 8k | 9a | 8m | 5y | 11v | 10c |
| II-419 | 1e, 2e, 3e, 8k | 9a | 8m | 5y | 11w | 10c |
| II-420 | 1e, 2e, 3e, 8k | 9a | 8m | 5y | 11x | 10c |
| II-421 | 1e, 2e, 3e, 8k | 9a | 8m | 5y | 11y | 10c |
| II-422 | 1e, 2e, 3e, 8k | 9a | 8m | 5y | 11z | 10c |
| II-423 | 1e, 2e, 3e, 8k | 9a | 8m | 5y | 11aa | 10c |
| II-424 | 1e, 2e, 3e, 8k | 9a | 8m | 5y | 11bb | 10c |
| II-425 | 1e, 2e, 3e, 8k | 9a | 8m | 5y | 11cc | 10c |
| II-426 | 1e, 2e, 3e, 8k | 9a | 8m | 5y | 11dd | 10c |
| II-427 | 1e, 2e, 3e, 8k | 9a | 8m | 5y | 11ee | 10c |
| II-428 | 1e, 2e, 3e, 8k | 9a | 8m | 5y | 11ff | 10c |
| II-429 | 1e, 2e, 3e, 8k | 9a | 8m | 5y | 11gg | 10c |
| II-430 | 1e, 2e, 3e, 8k | 9a | 8q | 5y | 11a | 10c |
| II-431 | 1e, 2e, 3e, 8k | 9a | 8q | 5y | 11b | 10c |
| II-432 | 1e, 2e, 3e, 8k | 9a | 8q | 5y | 11c | 10c |
| II-433 | 1e, 2e, 3e, 8k | 9a | 8q | 5y | 11d | 10c |
| II-434 | 1e, 2e, 3e, 8k | 9a | 8q | 5y | 11e | 10c |
| II-435 | 1e, 2e, 3e, 8k | 9a | 8q | 5y | 11f | 10c |
| II-436 | 1e, 2e, 3e, 8k | 9a | 8q | 5y | 11g | 10c |
| II-437 | 1e, 2e, 3e, 8k | 9a | 8q | 5y | 11h | 10c |
| II-438 | 1e, 2e, 3e, 8k | 9a | 8q | 5y | 11i | 10c |
| II-439 | 1e, 2e, 3e, 8k | 9a | 8q | 5y | 11j | 10c |
| II-440 | 1e, 2e, 3e, 8k | 9a | 8q | 5y | 11k | 10c |
| II-441 | 1e, 2e, 3e, 8k | 9a | 8q | 5y | 11l | 10c |
| II-442 | 1e, 2e, 3e, 8k | 9a | 8q | 5y | 11m | 10c |
| II-443 | 1e, 2e, 3e, 8k | 9a | 8q | 5y | 11n | 10c |
| II-444 | 1e, 2e, 3e, 8k | 9a | 8q | 5y | 11o | 10c |
| II-445 | 1e, 2e, 3e, 8k | 9a | 8q | 5y | 11p | 10c |
| II-446 | 1e, 2e, 3e, 8k | 9a | 8q | 5y | 11q | 10c |
| II-447 | 1e, 2e, 3e, 8k | 9a | 8q | 5y | 11r | 10c |
| II-448 | 1e, 2e, 3e, 8k | 9a | 8q | 5y | 11s | 10c |
| II-449 | 1e, 2e, 3e, 8k | 9a | 8q | 5y | 11t | 10c |
| II-450 | 1e, 2e, 3e, 8k | 9a | 8q | 5y | 11u | 10c |
| II-451 | 1e, 2e, 3e, 8k | 9a | 8q | 5y | 11v | 10c |
| II-452 | 1e, 2e, 3e, 8k | 9a | 8q | 5y | 11w | 10c |
| II-453 | 1e, 2e, 3e, 8k | 9a | 8q | 5y | 11x | 10c |
| II-454 | 1e, 2e, 3e, 8k | 9a | 8q | 5y | 11y | 10c |
| II-455 | 1e, 2e, 3e, 8k | 9a | 8q | 5y | 11z | 10c |
| II-456 | 1e, 2e, 3e, 8k | 9a | 8q | 5y | 11aa | 10c |
| II-457 | 1e, 2e, 3e, 8k | 9a | 8q | 5y | 11bb | 10c |
| II-458 | 1e, 2e, 3e, 8k | 9a | 8q | 5y | 11cc | 10c |
| II-459 | 1e, 2e, 3e, 8k | 9a | 8q | 5y | 11dd | 10c |
| II-460 | 1e, 2e, 3e, 8k | 9a | 8q | 5y | 11ee | 10c |
| II-461 | 1e, 2e, 3e, 8k | 9a | 8q | 5y | 11ff | 10c |
| II-462 | 1e, 2e, 3e, 8k | 9a | 8q | 5y | 11gg | 10c |
| II-463 | 1e, 2e, 3e, 8k | 9d | 8m | 5y | 11a | 10c |
| II-464 | 1e, 2e, 3e, 8k | 9d | 8m | 5y | 11b | 10c |
| II-465 | 1e, 2e, 3e, 8k | 9d | 8m | 5y | 11c | 10c |
| II-466 | 1e, 2e, 3e, 8k | 9d | 8m | 5y | 11d | 10c |
| II-467 | 1e, 2e, 3e, 8k | 9d | 8m | 5y | 11e | 10c |
| II-468 | 1e, 2e, 3e, 8k | 9d | 8m | 5y | 11f | 10c |
| II-469 | 1e, 2e, 3e, 8k | 9d | 8m | 5y | 11g | 10c |
| II-470 | 1e, 2e, 3e, 8k | 9d | 8m | 5y | 11h | 10c |
| II-471 | 1e, 2e, 3e, 8k | 9d | 8m | 5y | 11i | 10c |
| II-472 | 1e, 2e, 3e, 8k | 9d | 8m | 5y | 11j | 10c |
| II-473 | 1e, 2e, 3e, 8k | 9d | 8m | 5y | 11k | 10c |
| II-474 | 1e, 2e, 3e, 8k | 9d | 8m | 5y | 11l | 10c |
| II-475 | 1e, 2e, 3e, 8k | 9d | 8m | 5y | 11m | 10c |
| II-476 | 1e, 2e, 3e, 8k | 9d | 8m | 5y | 11n | 10c |
| II-477 | 1e, 2e, 3e, 8k | 9d | 8m | 5y | 11o | 10c |
| II-478 | 1e, 2e, 3e, 8k | 9d | 8m | 5y | 11p | 10c |
| II-479 | 1e, 2e, 3e, 8k | 9d | 8m | 5y | 11q | 10c |
| II-480 | 1e, 2e, 3e, 8k | 9d | 8m | 5y | 11r | 10c |
| II-481 | 1e, 2e, 3e, 8k | 9d | 8m | 5y | 11s | 10c |
| II-482 | 1e, 2e, 3e, 8k | 9d | 8m | 5y | 11t | 10c |
| II-483 | 1e, 2e, 3e, 8k | 9d | 8m | 5y | 11u | 10c |
| II-484 | 1e, 2e, 3e, 8k | 9d | 8m | 5y | 11v | 10c |
| II-485 | 1e, 2e, 3e, 8k | 9d | 8m | 5y | 11w | 10c |
| II-486 | 1e, 2e, 3e, 8k | 9d | 8m | 5y | 11x | 10c |
| II-487 | 1e, 2e, 3e, 8k | 9d | 8m | 5y | 11y | 10c |
| II-488 | 1e, 2e, 3e, 8k | 9d | 8m | 5y | 11z | 10c |
| II-489 | 1e, 2e, 3e, 8k | 9d | 8m | 5y | 11aa | 10c |
| II-490 | 1e, 2e, 3e, 8k | 9d | 8m | 5y | 11bb | 10c |
| II-491 | 1e, 2e, 3e, 8k | 9d | 8m | 5y | 11cc | 10c |
| II-492 | 1e, 2e, 3e, 8k | 9d | 8m | 5y | 11dd | 10c |
| II-493 | 1e, 2e, 3e, 8k | 9d | 8m | 5y | 11ee | 10c |
| II-494 | 1e, 2e, 3e, 8k | 9d | 8m | 5y | 11ff | 10c |
| II-495 | 1e, 2e, 3e, 8k | 9d | 8m | 5y | 11gg | 10c |
| II-496 | 1e, 2e, 3e, 8k | 9d | 8q | 5y | 11a | 10c |
| II-497 | 1e, 2e, 3e, 8k | 9d | 8q | 5y | 11b | 10c |
| II-498 | 1e, 2e, 3e, 8k | 9d | 8q | 5y | 11c | 10c |
| II-499 | 1e, 2e, 3e, 8k | 9d | 8q | 5y | 11d | 10c |
| II-500 | 1e, 2e, 3e, 8k | 9d | 8q | 5y | 11e | 10c |
| II-501 | 1e, 2e, 3e, 8k | 9d | 8q | 5y | 11f | 10c |
| II-502 | 1e, 2e, 3e, 8k | 9d | 8q | 5y | 11g | 10c |
| II-503 | 1e, 2e, 3e, 8k | 9d | 8q | 5y | 11h | 10c |
| II-504 | 1e, 2e, 3e, 8k | 9d | 8q | 5y | 11i | 10c |
| II-505 | 1e, 2e, 3e, 8k | 9d | 8q | 5y | 11j | 10c |
| II-506 | 1e, 2e, 3e, 8k | 9d | 8q | 5y | 11k | 10c |
| II-507 | 1e, 2e, 3e, 8k | 9d | 8q | 5y | 11l | 10c |
| II-508 | 1e, 2e, 3e, 8k | 9d | 8q | 5y | 11m | 10c |
| II-509 | 1e, 2e, 3e, 8k | 9d | 8q | 5y | 11n | 10c |
| II-510 | 1e, 2e, 3e, 8k | 9d | 8q | 5y | 11o | 10c |
| II-511 | 1e, 2e, 3e, 8k | 9d | 8q | 5y | 11p | 10c |

-continued

| Embodiment | R¹, R², R⁴, R⁵ | R³ | R⁶ | L¹ | R²⁰ | R³¹ |
|---|---|---|---|---|---|---|
| II-512 | 1e, 2e, 3e, 8k | 9d | 8q | 5y | 11q | 10c |
| II-513 | 1e, 2e, 3e, 8k | 9d | 8q | 5y | 11r | 10c |
| II-514 | 1e, 2e, 3e, 8k | 9d | 8q | 5y | 11s | 10c |
| II-515 | 1e, 2e, 3e, 8k | 9d | 8q | 5y | 11t | 10c |
| II-516 | 1e, 2e, 3e, 8k | 9d | 8q | 5y | 11u | 10c |
| II-517 | 1e, 2e, 3e, 8k | 9d | 8q | 5y | 11v | 10c |
| II-518 | 1e, 2e, 3e, 8k | 9d | 8q | 5y | 11w | 10c |
| II-519 | 1e, 2e, 3e, 8k | 9d | 8q | 5y | 11x | 10c |
| II-520 | 1e, 2e, 3e, 8k | 9d | 8q | 5y | 11y | 10c |
| II-521 | 1e, 2e, 3e, 8k | 9d | 8q | 5y | 11z | 10c |
| II-522 | 1e, 2e, 3e, 8k | 9d | 8q | 5y | 11aa | 10c |
| II-523 | 1e, 2e, 3e, 8k | 9d | 8q | 5y | 11bb | 10c |
| II-524 | 1e, 2e, 3e, 8k | 9d | 8q | 5y | 11cc | 10c |
| II-525 | 1e, 2e, 3e, 8k | 9d | 8q | 5y | 11dd | 10c |
| II-526 | 1e, 2e, 3e, 8k | 9d | 8q | 5y | 11ee | 10c |
| II-527 | 1e, 2e, 3e, 8k | 9d | 8q | 5y | 11ff | 10c |
| II-528 | 1e, 2e, 3e, 8k | 9d | 8q | 5y | 11gg | 10c |

In embodiment (3) of the first aspect, the invention comprises the compound of formula (III), or any one of (IIIa)-(IIIe),

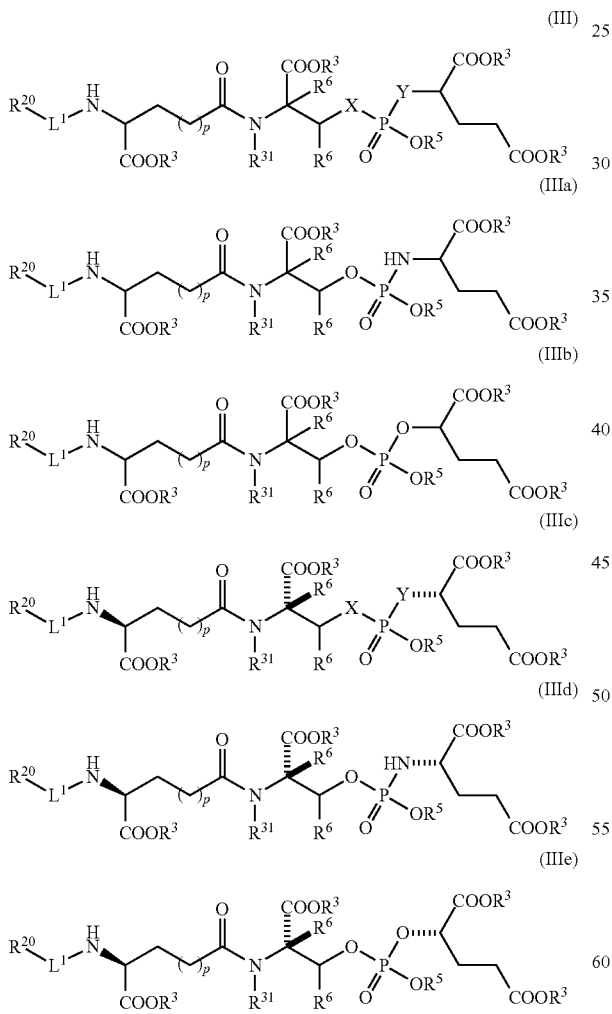

and pharmaceutically acceptable salts thereof, wherein p is 0 or 1; $R^{20}$ is —$C_1$-$C_7$alkyl-$R^9$, -aryl-$R^9$, -aryl($C_1$-$C_7$) alkyl-$R^9$, or -heteroaryl-$R^9$, and $R^3$, $R^5$, $R^6$, $R^9$, $R^{31}$, $L^1$, X and Y are as defined for formula (I).

The invention further comprises subgenera of embodiment (3) of the first aspect in which the substituents are selected as any and all combinations of $R^3$, $R^5$, $R^6$, $R^{20}$, $R^{31}$, $L^1$, X, and Y as defined herein, including without limitation, the following:

each $R^3$ is independently one of groups (9a)-(9e) as defined above for formula (II).

$R^5$ is one of groups (8h)-(8l) as defined above for formula (I).

each $R^6$ is independently one of groups (8m)-(8q) as defined above for formula (I).

$R^{20}$ is one of groups (11a)-(11gg) as defined above for formula (II).

$R^{31}$ is one of groups (10a)-(10e) as defined above for formula (II).

$L^1$ is one of groups (5v)-(5z) as defined above for foiniula (I).

X and Y are one of groups (7a)-(7g) as defined above for formula (I).

Particular embodiments of this embodiment of the invention include compounds of any one of formulae (III) and (IIIa)-(IIIe) wherein are defined in each of the following rows, wherein each entry is a group number as defined above:

| Embodiment | R³ & R⁵ | R⁶ | R²⁰ | R³¹ | L¹ |
|---|---|---|---|---|---|
| III-1 | 9a, 8h | 8m | 11a | 10c | 5v |
| III-2 | 9a, 8h | 8m | 11b | 10c | 5v |
| III-3 | 9a, 8h | 8m | 11c | 10c | 5v |
| III-4 | 9a, 8h | 8m | 11d | 10c | 5v |
| III-5 | 9a, 8h | 8m | 11e | 10c | 5v |
| III-6 | 9a, 8h | 8m | 11f | 10c | 5v |
| III-7 | 9a, 8h | 8m | 11g | 10c | 5v |
| III-8 | 9a, 8h | 8m | 11h | 10c | 5v |
| III-9 | 9a, 8h | 8m | 11i | 10c | 5v |
| III-10 | 9a, 8h | 8m | 11j | 10c | 5v |
| III-11 | 9a, 8h | 8m | 11k | 10c | 5v |
| III-12 | 9a, 8h | 8m | 11l | 10c | 5v |
| III-13 | 9a, 8h | 8m | 11m | 10c | 5v |
| III-14 | 9a, 8h | 8m | 11n | 10c | 5v |
| III-15 | 9a, 8h | 8m | 11o | 10c | 5v |
| III-16 | 9a, 8h | 8m | 11p | 10c | 5v |
| III-17 | 9a, 8h | 8m | 11q | 10c | 5v |
| III-18 | 9a, 8h | 8m | 11r | 10c | 5v |
| III-19 | 9a, 8h | 8m | 11s | 10c | 5v |
| III-20 | 9a, 8h | 8m | 11t | 10c | 5v |
| III-21 | 9a, 8h | 8m | 11u | 10c | 5v |
| III-22 | 9a, 8h | 8m | 11v | 10c | 5v |
| III-23 | 9a, 8h | 8m | 11w | 10c | 5v |
| III-24 | 9a, 8h | 8m | 11x | 10c | 5v |
| III-25 | 9a, 8h | 8m | 11y | 10c | 5v |
| III-26 | 9a, 8h | 8m | 11z | 10c | 5v |
| III-27 | 9a, 8h | 8m | 11aa | 10c | 5v |
| III-28 | 9a, 8h | 8m | 11bb | 10c | 5v |
| III-29 | 9a, 8h | 8m | 11cc | 10c | 5v |
| III-30 | 9a, 8h | 8m | 11dd | 10c | 5v |
| III-31 | 9a, 8h | 8m | 11ee | 10c | 5v |
| III-32 | 9a, 8h | 8m | 11ff | 10c | 5v |
| III-33 | 9a, 8h | 8m | 11gg | 10c | 5v |
| III-34 | 9a, 8h | 8q | 11a | 10c | 5v |
| III-35 | 9a, 8h | 8q | 11b | 10c | 5v |
| III-36 | 9a, 8h | 8q | 11c | 10c | 5v |
| III-37 | 9a, 8h | 8q | 11d | 10c | 5v |
| III-38 | 9a, 8h | 8q | 11e | 10c | 5v |
| III-39 | 9a, 8h | 8q | 11f | 10c | 5v |
| III-40 | 9a, 8h | 8q | 11g | 10c | 5v |
| III-41 | 9a, 8h | 8q | 11h | 10c | 5v |
| III-42 | 9a, 8h | 8q | 11i | 10c | 5v |
| III-43 | 9a, 8h | 8q | 11j | 10c | 5v |
| III-44 | 9a, 8h | 8q | 11k | 10c | 5v |
| III-45 | 9a, 8h | 8q | 11l | 10c | 5v |
| III-46 | 9a, 8h | 8q | 11m | 10c | 5v |
| III-47 | 9a, 8h | 8q | 11n | 10c | 5v |
| III-48 | 9a, 8h | 8q | 11o | 10c | 5v |
| III-49 | 9a, 8h | 8q | 11p | 10c | 5v |

-continued

| Embodiment | R³ & R⁵ | R⁶ | R²⁰ | R³¹ | L¹ |
|---|---|---|---|---|---|
| III-50 | 9a, 8h | 8q | 11q | 10c | 5v |
| III-51 | 9a, 8h | 8q | 11r | 10c | 5v |
| III-52 | 9a, 8h | 8q | 11s | 10c | 5v |
| III-53 | 9a, 8h | 8q | 11t | 10c | 5v |
| III-54 | 9a, 8h | 8q | 11u | 10c | 5v |
| III-55 | 9a, 8h | 8q | 11v | 10c | 5v |
| III-56 | 9a, 8h | 8q | 11w | 10c | 5v |
| III-57 | 9a, 8h | 8q | 11x | 10c | 5v |
| III-58 | 9a, 8h | 8q | 11y | 10c | 5v |
| III-59 | 9a, 8h | 8q | 11z | 10c | 5v |
| III-60 | 9a, 8h | 8q | 11aa | 10c | 5v |
| III-61 | 9a, 8h | 8q | 11bb | 10c | 5v |
| III-62 | 9a, 8h | 8q | 11cc | 10c | 5v |
| III-63 | 9a, 8h | 8q | 11dd | 10c | 5v |
| III-64 | 9a, 8h | 8q | 11ee | 10c | 5v |
| III-65 | 9a, 8h | 8q | 11ff | 10c | 5v |
| III-66 | 9a, 8h | 8q | 11gg | 10c | 5v |
| III-67 | 9d, 8k | 8m | 11a | 10c | 5v |
| III-68 | 9d, 8k | 8m | 11b | 10c | 5v |
| III-69 | 9d, 8k | 8m | 11c | 10c | 5v |
| III-70 | 9d, 8k | 8m | 11d | 10c | 5v |
| III-71 | 9d, 8k | 8m | 11e | 10c | 5v |
| III-72 | 9d, 8k | 8m | 11f | 10c | 5v |
| III-73 | 9d, 8k | 8m | 11g | 10c | 5v |
| III-74 | 9d, 8k | 8m | 11h | 10c | 5v |
| III-75 | 9d, 8k | 8m | 11i | 10c | 5v |
| III-76 | 9d, 8k | 8m | 11j | 10c | 5v |
| III-77 | 9d, 8k | 8m | 11k | 10c | 5v |
| III-78 | 9d, 8k | 8m | 11l | 10c | 5v |
| III-79 | 9d, 8k | 8m | 11m | 10c | 5v |
| III-80 | 9d, 8k | 8m | 11n | 10c | 5v |
| III-81 | 9d, 8k | 8m | 11o | 10c | 5v |
| III-82 | 9d, 8k | 8m | 11p | 10c | 5v |
| III-83 | 9d, 8k | 8m | 11q | 10c | 5v |
| III-84 | 9d, 8k | 8m | 11r | 10c | 5v |
| III-85 | 9d, 8k | 8m | 11s | 10c | 5v |
| III-86 | 9d, 8k | 8m | 11t | 10c | 5v |
| III-87 | 9d, 8k | 8m | 11u | 10c | 5v |
| III-88 | 9d, 8k | 8m | 11v | 10c | 5v |
| III-89 | 9d, 8k | 8m | 11w | 10c | 5v |
| III-90 | 9d, 8k | 8m | 11x | 10c | 5v |
| III-91 | 9d, 8k | 8m | 11y | 10c | 5v |
| III-92 | 9d, 8k | 8m | 11z | 10c | 5v |
| III-93 | 9d, 8k | 8m | 11aa | 10c | 5v |
| III-94 | 9d, 8k | 8m | 11bb | 10c | 5v |
| III-95 | 9d, 8k | 8m | 11cc | 10c | 5v |
| III-96 | 9d, 8k | 8m | 11dd | 10c | 5v |
| III-97 | 9d, 8k | 8m | 11ee | 10c | 5v |
| III-98 | 9d, 8k | 8m | 11ff | 10c | 5v |
| III-99 | 9d, 8k | 8m | 11gg | 10c | 5v |
| III-100 | 9d, 8k | 8q | 11a | 10c | 5v |
| III-101 | 9d, 8k | 8q | 11b | 10c | 5v |
| III-102 | 9d, 8k | 8q | 11c | 10c | 5v |
| III-103 | 9d, 8k | 8q | 11d | 10c | 5v |
| III-104 | 9d, 8k | 8q | 11e | 10c | 5v |
| III-105 | 9d, 8k | 8q | 11f | 10c | 5v |
| III-106 | 9d, 8k | 8q | 11g | 10c | 5v |
| III-107 | 9d, 8k | 8q | 11h | 10c | 5v |
| III-108 | 9d, 8k | 8q | 11i | 10c | 5v |
| III-109 | 9d, 8k | 8q | 11j | 10c | 5v |
| III-110 | 9d, 8k | 8q | 11k | 10c | 5v |
| III-111 | 9d, 8k | 8q | 11l | 10c | 5v |
| III-112 | 9d, 8k | 8q | 11m | 10c | 5v |
| III-113 | 9d, 8k | 8q | 11n | 10c | 5v |
| III-114 | 9d, 8k | 8q | 11o | 10c | 5v |
| III-115 | 9d, 8k | 8q | 11p | 10c | 5v |
| III-116 | 9d, 8k | 8q | 11q | 10c | 5v |
| III-117 | 9d, 8k | 8q | 11r | 10c | 5v |
| III-118 | 9d, 8k | 8q | 11s | 10c | 5v |
| III-119 | 9d, 8k | 8q | 11t | 10c | 5v |
| III-120 | 9d, 8k | 8q | 11u | 10c | 5v |
| III-121 | 9d, 8k | 8q | 11v | 10c | 5v |
| III-122 | 9d, 8k | 8q | 11w | 10c | 5v |
| III-123 | 9d, 8k | 8q | 11x | 10c | 5v |
| III-124 | 9d, 8k | 8q | 11y | 10c | 5v |
| III-125 | 9d, 8k | 8q | 11z | 10c | 5v |
| III-126 | 9d, 8k | 8q | 11aa | 10c | 5v |
| III-127 | 9d, 8k | 8q | 11bb | 10c | 5v |
| III-128 | 9d, 8k | 8q | 11cc | 10c | 5v |
| III-129 | 9d, 8k | 8q | 11dd | 10c | 5v |
| III-130 | 9d, 8k | 8q | 11ee | 10c | 5v |
| III-131 | 9d, 8k | 8q | 11ff | 10c | 5v |
| III-132 | 9d, 8k | 8q | 11gg | 10c | 5v |
| III-133 | 9a, 8h | 8m | 11a | 10c | 5y |
| III-134 | 9a, 8h | 8m | 11b | 10c | 5y |
| III-135 | 9a, 8h | 8m | 11c | 10c | 5y |
| III-136 | 9a, 8h | 8m | 11d | 10c | 5y |
| III-137 | 9a, 8h | 8m | 11e | 10c | 5y |
| III-138 | 9a, 8h | 8m | 11f | 10c | 5y |
| III-139 | 9a, 8h | 8m | 11g | 10c | 5y |
| III-140 | 9a, 8h | 8m | 11h | 10c | 5y |
| III-141 | 9a, 8h | 8m | 11i | 10c | 5y |
| III-142 | 9a, 8h | 8m | 11j | 10c | 5y |
| III-143 | 9a, 8h | 8m | 11k | 10c | 5y |
| III-144 | 9a, 8h | 8m | 11l | 10c | 5y |
| III-145 | 9a, 8h | 8m | 11m | 10c | 5y |
| III-146 | 9a, 8h | 8m | 11n | 10c | 5y |
| III-147 | 9a, 8h | 8m | 11o | 10c | 5y |
| III-148 | 9a, 8h | 8m | 11p | 10c | 5y |
| III-149 | 9a, 8h | 8m | 11q | 10c | 5y |
| III-150 | 9a, 8h | 8m | 11r | 10c | 5y |
| III-151 | 9a, 8h | 8m | 11s | 10c | 5y |
| III-152 | 9a, 8h | 8m | 11t | 10c | 5y |
| III-153 | 9a, 8h | 8m | 11u | 10c | 5y |
| III-154 | 9a, 8h | 8m | 11v | 10c | 5y |
| III-155 | 9a, 8h | 8m | 11w | 10c | 5y |
| III-156 | 9a, 8h | 8m | 11x | 10c | 5y |
| III-157 | 9a, 8h | 8m | 11y | 10c | 5y |
| III-158 | 9a, 8h | 8m | 11z | 10c | 5y |
| III-159 | 9a, 8h | 8m | 11aa | 10c | 5y |
| III-160 | 9a, 8h | 8m | 11bb | 10c | 5y |
| III-161 | 9a, 8h | 8m | 11cc | 10c | 5y |
| III-162 | 9a, 8h | 8m | 1dd | 10c | 5y |
| III-163 | 9a, 8h | 8m | 11ee | 10c | 5y |
| III-164 | 9a, 8h | 8m | 11ff | 10c | 5y |
| III-165 | 9a, 8h | 8m | 11gg | 10c | 5y |
| III-166 | 9a, 8h | 8q | 11a | 10c | 5y |
| III-167 | 9a, 8h | 8q | 11b | 10c | 5y |
| III-168 | 9a, 8h | 8q | 11c | 10c | 5y |
| III-169 | 9a, 8h | 8q | 11d | 10c | 5y |
| III-170 | 9a, 8h | 8q | 11e | 10c | 5y |
| III-171 | 9a, 8h | 8q | 11f | 10c | 5y |
| III-172 | 9a, 8h | 8q | 11g | 10c | 5y |
| III-173 | 9a, 8h | 8q | 11h | 10c | 5y |
| III-174 | 9a, 8h | 8q | 11i | 10c | 5y |
| III-175 | 9a, 8h | 8q | 11j | 10c | 5y |
| III-176 | 9a, 8h | 8q | 11k | 10c | 5y |
| III-177 | 9a, 8h | 8q | 11l | 10c | 5y |
| III-178 | 9a, 8h | 8q | 11m | 10c | 5y |
| III-179 | 9a, 8h | 8q | 11n | 10c | 5y |
| III-180 | 9a, 8h | 8q | 11o | 10c | 5y |
| III-181 | 9a, 8h | 8q | 11p | 10c | 5y |
| III-182 | 9a, 8h | 8q | 11q | 10c | 5y |
| III-183 | 9a, 8h | 8q | 11r | 10c | 5y |
| III-184 | 9a, 8h | 8q | 11s | 10c | 5y |
| III-185 | 9a, 8h | 8q | 11t | 10c | 5y |
| III-186 | 9a, 8h | 8q | 11u | 10c | 5y |
| III-187 | 9a, 8h | 8q | 11v | 10c | 5y |
| III-188 | 9a, 8h | 8q | 11w | 10c | 5y |
| III-189 | 9a, 8h | 8q | 11x | 10c | 5y |
| III-190 | 9a, 8h | 8q | 11y | 10c | 5y |
| III-191 | 9a, 8h | 8q | 11z | 10c | 5y |
| III-192 | 9a, 8h | 8q | 11aa | 10c | 5y |
| III-193 | 9a, 8h | 8q | 11bb | 10c | 5y |
| III-194 | 9a, 8h | 8q | 11cc | 10c | 5y |
| III-195 | 9a, 8h | 8q | 11dd | 10c | 5y |
| III-196 | 9a, 8h | 8q | 11ee | 10c | 5y |
| III-197 | 9a, 8h | 8q | 11ff | 10c | 5y |
| III-198 | 9a, 8h | 8q | 11gg | 10c | 5y |
| III-199 | 9d, 8k | 8m | 11a | 10c | 5y |
| III-200 | 9d, 8k | 8m | 11b | 10c | 5y |
| III-201 | 9d, 8k | 8m | 11c | 10c | 5y |
| III-202 | 9d, 8k | 8m | 11d | 10c | 5y |
| III-203 | 9d, 8k | 8m | 11e | 10c | 5y |

-continued

| Embodiment | R³ & R⁵ | R⁶ | R²⁰ | R³¹ | L¹ |
|---|---|---|---|---|---|
| III-204 | 9d, 8k | 8m | 11f | 10c | 5y |
| III-205 | 9d, 8k | 8m | 11g | 10c | 5y |
| III-206 | 9d, 8k | 8m | 11h | 10c | 5y |
| III-207 | 9d, 8k | 8m | 11i | 10c | 5y |
| III-208 | 9d, 8k | 8m | 11j | 10c | 5y |
| III-209 | 9d, 8k | 8m | 11k | 10c | 5y |
| III-210 | 9d, 8k | 8m | 11l | 10c | 5y |
| III-211 | 9d, 8k | 8m | 11m | 10c | 5y |
| III-212 | 9d, 8k | 8m | 11n | 10c | 5y |
| III-213 | 9d, 8k | 8m | 11o | 10c | 5y |
| III-214 | 9d, 8k | 8m | 11p | 10c | 5y |
| III-215 | 9d, 8k | 8m | 11q | 10c | 5y |
| III-216 | 9d, 8k | 8m | 11r | 10c | 5y |
| III-211 | 9d, 8k | 8m | 11s | 10c | 5y |
| III-218 | 9d, 8k | 8m | 11t | 10c | 5y |
| III-219 | 9d, 8k | 8m | 11u | 10c | 5y |
| III-220 | 9d, 8k | 8m | 11v | 10c | 5y |
| III-221 | 9d, 8k | 8m | 11w | 10c | 5y |
| III-222 | 9d, 8k | 8m | 11x | 10c | 5y |
| III-223 | 9d, 8k | 8m | 11y | 10c | 5y |
| III-224 | 9d, 8k | 8m | 11z | 10c | 5y |
| III-225 | 9d, 8k | 8m | 11aa | 10c | 5y |
| III-226 | 9d, 8k | 8m | 11bb | 10c | 5y |
| III-227 | 9d, 8k | 8m | 11cc | 10c | 5y |
| III-228 | 9d, 8k | 8m | 11dd | 10c | 5y |
| III-229 | 9d, 8k | 8m | 11ee | 10c | 5y |
| III-230 | 9d, 8k | 8m | 11ff | 10c | 5y |
| III-231 | 9d, 8k | 8m | 11gg | 10c | 5y |
| III-232 | 9d, 8k | 8q | 11a | 10c | 5y |
| III-233 | 9d, 8k | 8q | 11b | 10c | 5y |
| III-234 | 9d, 8k | 8q | 11c | 10c | 5y |
| III-235 | 9d, 8k | 8q | 11d | 10c | 5y |
| III-236 | 9d, 8k | 8q | 11e | 10c | 5y |
| III-237 | 9d, 8k | 8q | 11f | 10c | 5y |
| III-238 | 9d, 8k | 8q | 11g | 10c | 5y |
| III-239 | 9d, 8k | 8q | 11h | 10c | 5y |
| III-240 | 9d, 8k | 8q | 11i | 10c | 5y |
| III-241 | 9d, 8k | 8q | 11j | 10c | 5y |
| III-242 | 9d, 8k | 8q | 11k | 10c | 5y |
| III-243 | 9d, 8k | 8q | 11l | 10c | 5y |
| III-244 | 9d, 8k | 8q | 11m | 10c | 5y |
| III-245 | 9d, 8k | 8q | 11n | 10c | 5y |
| III-246 | 9d, 8k | 8q | 11o | 10c | 5y |
| III-247 | 9d, 8k | 8q | 11p | 10c | 5y |
| III-248 | 9d, 8k | 8q | 11q | 10c | 5y |
| III-249 | 9d, 8k | 8q | 11r | 10c | 5y |
| III-250 | 9d, 8k | 8q | 11s | 10c | 5y |
| III-251 | 9d, 8k | 8q | 11t | 10c | 5y |
| III-252 | 9d, 8k | 8q | 11u | 10c | 5y |
| III-253 | 9d, 8k | 8q | 11v | 10c | 5y |
| III-254 | 9d, 8k | 8q | 11w | 10c | 5y |
| III-255 | 9d, 8k | 8q | 11x | 10c | 5y |
| III-256 | 9d, 8k | 8q | 11y | 10c | 5y |
| III-257 | 9d, 8k | 8q | 11z | 10c | 5y |
| III-258 | 9d, 8k | 8q | 11aa | 10c | 5y |
| III-259 | 9d, 8k | 8q | 11bb | 10c | 5y |
| III-260 | 9d, 8k | 8q | 11cc | 10c | 5y |
| III-261 | 9d, 8k | 8q | 11dd | 10c | 5y |
| III-262 | 9d, 8k | 8q | 11ee | 10c | 5y |
| III-263 | 9d, 8k | 8q | 11ff | 10c | 5y |
| III-264 | 9d, 8k | 8q | 11gg | 10c | 5y |

In embodiment (4) of the first aspect, the invention comprises the compound of formula (IV), or any one of (IVa)-(IVe),

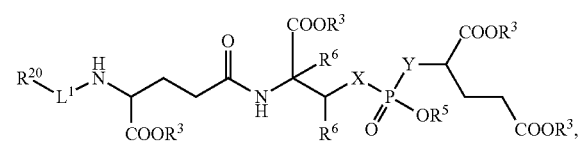
(IV)

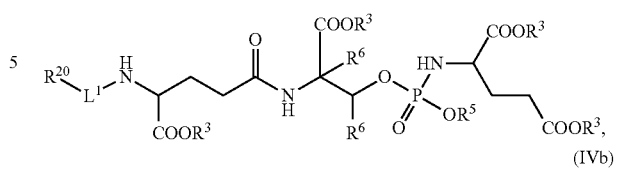
(IVa)

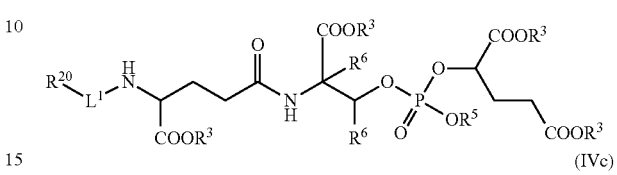
(IVb)

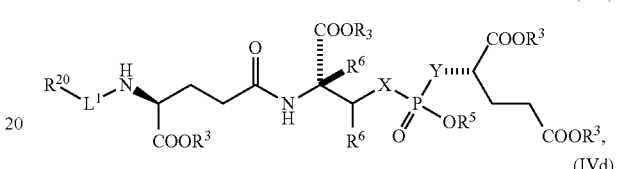
(IVc)

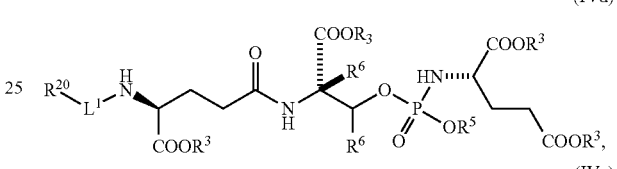
(IVd)

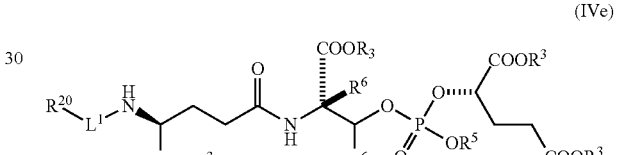
(IVe)

and pharmaceutically acceptable salts thereof, wherein $R^{20}$ is —$C_1$-$C_7$alkyl-$R^9$, aryl-$R^9$, -aryl($C_1$-$C_7$) alkyl-$R^9$, or -heteroaryl-$R^9$, and $R^3$, $R^5$, $R^6$, $L^1$, and $R^9$ are as defined for formula (I).

The invention further comprises subgenera of embodiment (4) of the first aspect in which the substituents are selected as any and all combinations of $R^3$, $R^5$, $R^6$, $R^{20}$, $L^1$, X, and Y as defined herein, including without limitation, each $R^3$ is independently one of groups (9a)-(9e) as defined above for formula (II).

$R^5$ is one of groups (8h)-(8l) as defined above for foimula (I).

each $R^6$ is independently one of groups (8m)-(8q) as defined above for formula (I).

$L^1$ is one of groups (5v)-(5z) as defined above for formula (I).

X and Y are one of groups (7a)-(7g) as defined above for formula (I).

$R^{20}$ is one of groups (11a) (11gg) as defined above for formula (II).

Particular embodiments of this embodiment of the invention include compounds of any one of formulae (IV) and (IVa)-(IVe) wherein are defined in each of the following rows, wherein each entry is a group number as defined above:

| Embodiment | R³ & R⁵ | R⁶ | R²⁰ | L¹ |
|---|---|---|---|---|
| IV-1 | 9a, 8h | 8m | 11a | 5v |
| IV-2 | 9a, 8h | 8m | 11b | 5v |
| IV-3 | 9a, 8h | 8m | 11c | 5v |

-continued

| Embodiment | R³ & R⁵ | R⁶ | R²⁰ | L¹ |
|---|---|---|---|---|
| IV-4 | 9a, 8h | 8m | 11d | 5v |
| IV-5 | 9a, 8h | 8m | 11e | 5v |
| IV-6 | 9a, 8h | 8m | 11f | 5v |
| IV-7 | 9a, 8h | 8m | 11g | 5v |
| IV-8 | 9a, 8h | 8m | 11h | 5v |
| IV-9 | 9a, 8h | 8m | 11i | 5v |
| IV-10 | 9a, 8h | 8m | 11j | 5v |
| IV-11 | 9a, 8h | 8m | 11k | 5v |
| IV-12 | 9a, 8h | 8m | 11l | 5v |
| IV-13 | 9a, 8h | 8m | 11m | 5v |
| IV-14 | 9a, 8h | 8m | 11n | 5v |
| IV-15 | 9a, 8h | 8m | 11o | 5v |
| IV-16 | 9a, 8h | 8m | 11p | 5v |
| IV-17 | 9a, 8h | 8m | 11q | 5v |
| IV-18 | 9a, 8h | 8m | 11r | 5v |
| IV-19 | 9a, 8h | 8m | 11s | 5v |
| IV-20 | 9a, 8h | 8m | 11t | 5v |
| IV-21 | 9a, 8h | 8m | 11u | 5v |
| IV-22 | 9a, 8h | 8m | 11v | 5v |
| IV-23 | 9a, 8h | 8m | 11w | 5v |
| IV-24 | 9a, 8h | 8m | 11x | 5v |
| IV-25 | 9a, 8h | 8m | 11y | 5v |
| IV-26 | 9a, 8h | 8m | 11z | 5v |
| IV-27 | 9a, 8h | 8m | 11aa | 5v |
| IV-28 | 9a, 8h | 8m | 11bb | 5v |
| IV-29 | 9a, 8h | 8m | 11cc | 5v |
| IV-30 | 9a, 8h | 8m | 11dd | 5v |
| IV-31 | 9a, 8h | 8m | 11ee | 5v |
| IV-32 | 9a, 8h | 8m | 11ff | 5v |
| IV-33 | 9a, 8h | 8m | 11gg | 5v |
| IV-34 | 9a, 8h | 8q | 11a | 5v |
| IV-35 | 9a, 8h | 8q | 11b | 5v |
| IV-36 | 9a, 8h | 8q | 11c | 5v |
| IV-37 | 9a, 8h | 8q | 11d | 5v |
| IV-38 | 9a, 8h | 8q | 11e | 5v |
| IV-39 | 9a, 8h | 8q | 11f | 5v |
| IV-40 | 9a, 8h | 8q | 11g | 5v |
| IV-41 | 9a, 8h | 8q | 11h | 5v |
| IV-42 | 9a, 8h | 8q | 11i | 5v |
| IV-43 | 9a, 8h | 8q | 11j | 5v |
| IV-44 | 9a, 8h | 8q | 11k | 5v |
| IV-45 | 9a, 8h | 8q | 11l | 5v |
| IV-46 | 9a, 8h | 8q | 11m | 5v |
| IV-47 | 9a, 8h | 8q | 11n | 5v |
| IV-48 | 9a, 8h | 8q | 11o | 5v |
| IV-49 | 9a, 8h | 8q | 11p | 5v |
| IV-50 | 9a, 8h | 8q | 11q | 5v |
| IV-51 | 9a, 8h | 8q | 11r | 5v |
| IV-52 | 9a, 8h | 8q | 11s | 5v |
| IV-53 | 9a, 8h | 8q | 11t | 5v |
| IV-54 | 9a, 8h | 8q | 11u | 5v |
| IV-55 | 9a, 8h | 8q | 11v | 5v |
| IV-56 | 9a, 8h | 8q | 11w | 5v |
| IV-57 | 9a, 8h | 8q | 11x | 5v |
| IV-58 | 9a, 8h | 8q | 11y | 5v |
| IV-59 | 9a, 8h | 8q | 11z | 5v |
| IV-60 | 9a, 8h | 8q | 11aa | 5v |
| IV-61 | 9a, 8h | 8q | 11bb | 5v |
| IV-62 | 9a, 8h | 8q | 11cc | 5v |
| IV-63 | 9a, 8h | 8q | 11dd | 5v |
| IV-64 | 9a, 8h | 8q | 11ee | 5v |
| IV-65 | 9a, 8h | 8q | 11ff | 5v |
| IV-66 | 9a, 8h | 8q | 11gg | 5v |
| IV-67 | 9d, 8k | 8m | 11a | 5v |
| IV-68 | 9d, 8k | 8m | 11b | 5v |
| IV-69 | 9d, 8k | 8m | 11c | 5v |
| IV-70 | 9d, 8k | 8m | 11d | 5v |
| IV-71 | 9d, 8k | 8m | 11e | 5v |
| IV-72 | 9d, 8k | 8m | 11f | 5v |
| IV-73 | 9d, 8k | 8m | 11g | 5v |
| IV-74 | 9d, 8k | 8m | 11h | 5v |
| IV-75 | 9d, 8k | 8m | 11i | 5v |
| IV-76 | 9d, 8k | 8m | 11j | 5v |
| IV-77 | 9d, 8k | 8m | 11k | 5v |
| IV-78 | 9d, 8k | 8m | 11l | 5v |
| IV-79 | 9d, 8k | 8m | 11m | 5v |
| IV-80 | 9d, 8k | 8m | 11n | 5v |
| IV-81 | 9d, 8k | 8m | 11o | 5v |
| IV-82 | 9d, 8k | 8m | 11p | 5v |
| IV-83 | 9d, 8k | 8m | 11q | 5v |
| IV-84 | 9d, 8k | 8m | 11r | 5v |
| IV-85 | 9d, 8k | 8m | 11s | 5v |
| IV-86 | 9d, 8k | 8m | 11t | 5v |
| IV-87 | 9d, 8k | 8m | 11u | 5v |
| IV-88 | 9d, 8k | 8m | 11v | 5v |
| IV-89 | 9d, 8k | 8m | 11w | 5v |
| IV-90 | 9d, 8k | 8m | 11x | 5v |
| IV-91 | 9d, 8k | 8m | 11y | 5v |
| IV-92 | 9d, 8k | 8m | 11z | 5v |
| IV-93 | 9d, 8k | 8m | 11aa | 5v |
| IV-94 | 9d, 8k | 8m | 11bb | 5v |
| IV-95 | 9d, 8k | 8m | 11cc | 5v |
| IV-96 | 9d, 8k | 8m | 11dd | 5v |
| IV-97 | 9d, 8k | 8m | 11ee | 5v |
| IV-98 | 9d, 8k | 8m | 11ff | 5v |
| IV-99 | 9d, 8k | 8m | 11gg | 5v |
| IV-100 | 9d, 8k | 8q | 11a | 5v |
| IV-101 | 9d, 8k | 8q | 11b | 5v |
| IV-102 | 9d, 8k | 8q | 11c | 5v |
| IV-103 | 9d, 8k | 8q | 11d | 5v |
| IV-104 | 9d, 8k | 8q | 11e | 5v |
| IV-105 | 9d, 8k | 8q | 11f | 5v |
| IV-106 | 9d, 8k | 8q | 11g | 5v |
| IV-107 | 9d, 8k | 8q | 11h | 5v |
| IV-108 | 9d, 8k | 8q | 11i | 5v |
| IV-109 | 9d, 8k | 8q | 11j | 5v |
| IV-110 | 9d, 8k | 8q | 11k | 5v |
| IV-111 | 9d, 8k | 8q | 11l | 5v |
| IV-112 | 9d, 8k | 8q | 11m | 5v |
| IV-113 | 9d, 8k | 8q | 11n | 5v |
| IV-114 | 9d, 8k | 8q | 11o | 5v |
| IV-115 | 9d, 8k | 8q | 11p | 5v |
| IV-116 | 9d, 8k | 8q | 11q | 5v |
| IV-117 | 9d, 8k | 8q | 11r | 5v |
| IV-118 | 9d, 8k | 8q | 11s | 5v |
| IV-119 | 9d, 8k | 8q | 11t | 5v |
| IV-120 | 9d, 8k | 8q | 11u | 5v |
| IV-121 | 9d, 8k | 8q | 11v | 5v |
| IV-122 | 9d, 8k | 8q | 11w | 5v |
| IV-123 | 9d, 8k | 8q | 11x | 5v |
| IV-124 | 9d, 8k | 8q | 11y | 5v |
| IV-125 | 9d, 8k | 8q | 11z | 5v |
| IV-126 | 9d, 8k | 8q | 11aa | 5v |
| IV-127 | 9d, 8k | 8q | 11bb | 5v |
| IV-128 | 9d, 8k | 8q | 11cc | 5v |
| IV-129 | 9d, 8k | 8q | 11dd | 5v |
| IV-130 | 9d, 8k | 8q | 11ee | 5v |
| IV-131 | 9d, 8k | 8q | 11ff | 5v |
| IV-132 | 9d, 8k | 8q | 11gg | 5v |
| IV-133 | 9a, 8h | 8m | 11a | 5y |
| IV-134 | 9a, 8h | 8m | 11b | 5y |
| IV-135 | 9a, 8h | 8m | 11c | 5y |
| IV-136 | 9a, 8h | 8m | 11d | 5y |
| IV-137 | 9a, 8h | 8m | 11e | 5y |
| IV-138 | 9a, 8h | 8m | 11f | 5y |
| IV-139 | 9a, 8h | 8m | 11g | 5y |
| IV-140 | 9a, 8h | 8m | 11h | 5y |
| IV-141 | 9a, 8h | 8m | 11i | 5y |
| IV-142 | 9a, 8h | 8m | 11j | 5y |
| IV-143 | 9a, 8h | 8m | 11k | 5y |
| IV-144 | 9a, 8h | 8m | 11l | 5y |
| IV-145 | 9a, 8h | 8m | 11m | 5y |
| IV-146 | 9a, 8h | 8m | 11n | 5y |
| IV-147 | 9a, 8h | 8m | 11o | 5y |
| IV-148 | 9a, 8h | 8m | 11p | 5y |
| IV-149 | 9a, 8h | 8m | 11q | 5y |
| IV-150 | 9a, 8h | 8m | 11r | 5y |
| IV-151 | 9a, 8h | 8m | 11s | 5y |
| IV-152 | 9a, 8h | 8m | 11t | 5y |
| IV-153 | 9a, 8h | 8m | 11u | 5y |
| IV-154 | 9a, 8h | 8m | 11v | 5y |
| IV-155 | 9a, 8h | 8m | 11w | 5y |
| IV-156 | 9a, 8h | 8m | 11x | 5y |
| IV-157 | 9a, 8h | 8m | 11y | 5y |

| Embodiment | R³ & R⁵ | R⁶ | R²⁰ | L¹ |
|---|---|---|---|---|
| IV-158 | 9a, 8h | 8m | 11z | 5y |
| IV-159 | 9a, 8h | 8m | 11aa | 5y |
| IV-160 | 9a, 8h | 8m | 11bb | 5y |
| IV-161 | 9a, 8h | 8m | 11cc | 5y |
| IV-162 | 9a, 8h | 8m | 11dd | 5y |
| IV-163 | 9a, 8h | 8m | 11ee | 5y |
| IV-164 | 9a, 8h | 8m | 11ff | 5y |
| IV-165 | 9a, 8h | 8m | 11gg | 5y |
| IV-166 | 9a, 8h | 8q | 11a | 5y |
| IV-167 | 9a, 8h | 8q | 11b | 5y |
| IV-168 | 9a, 8h | 8q | 11c | 5y |
| IV-169 | 9a, 8h | 8q | 11d | 5y |
| IV-170 | 9a, 8h | 8q | 11e | 5y |
| IV-171 | 9a, 8h | 8q | 11f | 5y |
| IV-172 | 9a, 8h | 8q | 11g | 5y |
| IV-173 | 9a, 8h | 8q | 11h | 5y |
| IV-174 | 9a, 8h | 8q | 11i | 5y |
| IV-175 | 9a, 8h | 8q | 11j | 5y |
| IV-176 | 9a, 8h | 8q | 11k | 5y |
| IV-177 | 9a, 8h | 8q | 11l | 5y |
| IV-178 | 9a, 8h | 8q | 11m | 5y |
| IV-179 | 9a, 8h | 8q | 11n | 5y |
| IV-180 | 9a, 8h | 8q | 11o | 5y |
| IV-181 | 9a, 8h | 8q | 11p | 5y |
| IV-182 | 9a, 8h | 8q | 11q | 5y |
| IV-183 | 9a, 8h | 8q | 11r | 5y |
| IV-184 | 9a, 8h | 8q | 11s | 5y |
| IV-185 | 9a, 8h | 8q | 11t | 5y |
| IV-186 | 9a, 8h | 8q | 11u | 5y |
| IV-187 | 9a, 8h | 8q | 11v | 5y |
| IV-188 | 9a, 8h | 8q | 11w | 5y |
| IV-189 | 9a, 8h | 8q | 11x | 5y |
| IV-190 | 9a, 8h | 8q | 11y | 5y |
| IV-191 | 9a, 8h | 8q | 11z | 5y |
| IV-192 | 9a, 8h | 8q | 11aa | 5y |
| IV-193 | 9a, 8h | 8q | 11bb | 5y |
| IV-194 | 9a, 8h | 8q | 11cc | 5y |
| IV-195 | 9a, 8h | 8q | 11dd | 5y |
| IV-196 | 9a, 8h | 8q | 11ee | 5y |
| IV-197 | 9a, 8h | 8q | 11ff | 5y |
| IV-198 | 9a, 8h | 8q | 11gg | 5y |
| IV-199 | 9d, 8k | 8m | 11a | 5y |
| IV-200 | 9d, 8k | 8m | 11b | 5y |
| IV-201 | 9d, 8k | 8m | 11c | 5y |
| IV-202 | 9d, 8k | 8m | 11d | 5y |
| IV-203 | 9d, 8k | 8m | 11e | 5y |
| IV-204 | 9d, 8k | 8m | 11f | 5y |
| IV-205 | 9d, 8k | 8m | 11g | 5y |
| IV-206 | 9d, 8k | 8m | 11h | 5y |
| IV-207 | 9d, 8k | 8m | 11i | 5y |
| IV-208 | 9d, 8k | 8m | 11j | 5y |
| IV-209 | 9d, 8k | 8m | 11k | 5y |
| IV-210 | 9d, 8k | 8m | 11l | 5y |
| IV-211 | 9d, 8k | 8m | 11m | 5y |
| IV-212 | 9d, 8k | 8m | 11n | 5y |
| IV-213 | 9d, 8k | 8m | 11o | 5y |
| IV-214 | 9d, 8k | 8m | 11p | 5y |
| IV-215 | 9d, 8k | 8m | 11q | 5y |
| IV-216 | 9d, 8k | 8m | 11r | 5y |
| IV-217 | 9d, 8k | 8m | 11s | 5y |
| IV-218 | 9d, 8k | 8m | 11t | 5y |
| IV-219 | 9d, 8k | 8m | 11u | 5y |
| IV-220 | 9d, 8k | 8m | 11v | 5y |
| IV-221 | 9d, 8k | 8m | 11w | 5y |
| IV-222 | 9d, 8k | 8m | 11x | 5y |
| IV-223 | 9d, 8k | 8m | 11y | 5y |
| IV-224 | 9d, 8k | 8m | 11z | 5y |
| IV-225 | 9d, 8k | 8m | 11aa | 5y |
| IV-226 | 9d, 8k | 8m | 11bb | 5y |
| IV-227 | 9d, 8k | 8m | 11cc | 5y |
| IV-228 | 9d, 8k | 8m | 11dd | 5y |
| IV-229 | 9d, 8k | 8m | 11ee | 5y |
| IV-230 | 9d, 8k | 8m | 11ff | 5y |
| IV-231 | 9d, 8k | 8m | 11gg | 5y |
| IV-232 | 9d, 8k | 8q | 11a | 5y |
| IV-233 | 9d, 8k | 8q | 11b | 5y |
| IV-234 | 9d, 8k | 8q | 11c | 5y |
| IV-235 | 9d, 8k | 8q | 11d | 5y |
| IV-236 | 9d, 8k | 8q | 11e | 5y |
| IV-237 | 9d, 8k | 8q | 11f | 5y |
| IV-238 | 9d, 8k | 8q | 11g | 5y |
| IV-239 | 9d, 8k | 8q | 11h | 5y |
| IV-240 | 9d, 8k | 8q | 11i | 5y |
| IV-241 | 9d, 8k | 8q | 11j | 5y |
| IV-242 | 9d, 8k | 8q | 11k | 5y |
| IV-243 | 9d, 8k | 8q | 11l | 5y |
| IV-244 | 9d, 8k | 8q | 11m | 5y |
| IV-245 | 9d, 8k | 8q | 11n | 5y |
| IV-246 | 9d, 8k | 8q | 11o | 5y |
| IV-247 | 9d, 8k | 8q | 11p | 5y |
| IV-248 | 9d, 8k | 8q | 11q | 5y |
| IV-249 | 9d, 8k | 8q | 11r | 5y |
| IV-250 | 9d, 8k | 8q | 11s | 5y |
| IV-251 | 9d, 8k | 8q | 11t | 5y |
| IV-252 | 9d, 8k | 8q | 11u | 5y |
| IV-253 | 9d, 8k | 8q | 11v | 5y |
| IV-254 | 9d, 8k | 8q | 11w | 5y |
| IV-255 | 9d, 8k | 8q | 11x | 5y |
| IV-256 | 9d, 8k | 8q | 11y | 5y |
| IV-257 | 9d, 8k | 8q | 11z | 5y |
| IV-258 | 9d, 8k | 8q | 11aa | 5y |
| IV-259 | 9d, 8k | 8q | 11bb | 5y |
| IV-260 | 9d, 8k | 8q | 11cc | 5y |
| IV-261 | 9d, 8k | 8q | 11dd | 5y |
| IV-262 | 9d, 8k | 8q | 11ee | 5y |
| IV-263 | 9d, 8k | 8q | 11ff | 5y |
| IV-264 | 9d, 8k | 8q | 11gg | 5y |

Examples of a PSMA inhibitor bearing a polymer conjugate (PEG)

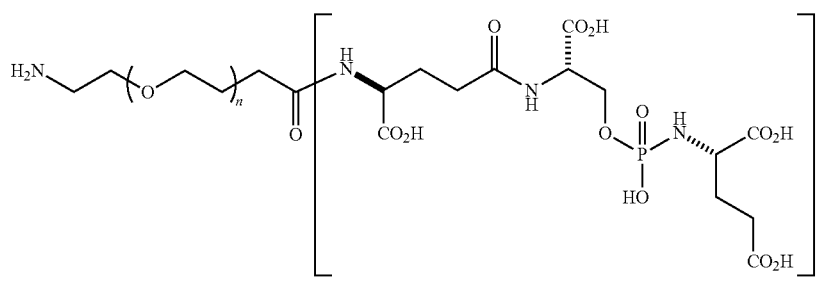

CTT-54

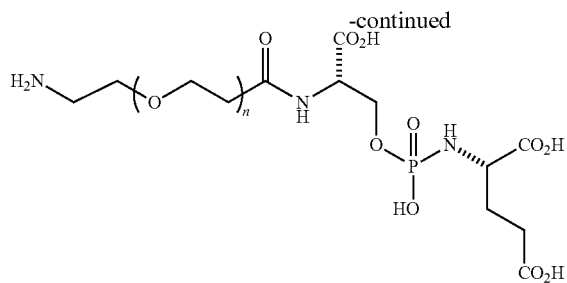
where n is 1-200, 100-200, 150-200, 1-100, 1-50, 1-10, or 1, 2, 3, 4, 5, 6, 7, 8, 9, or 10.
The invention compounds falling under the embodiments as disclosed above are not one or all of the following compounds in Table 1:
TABLE 1
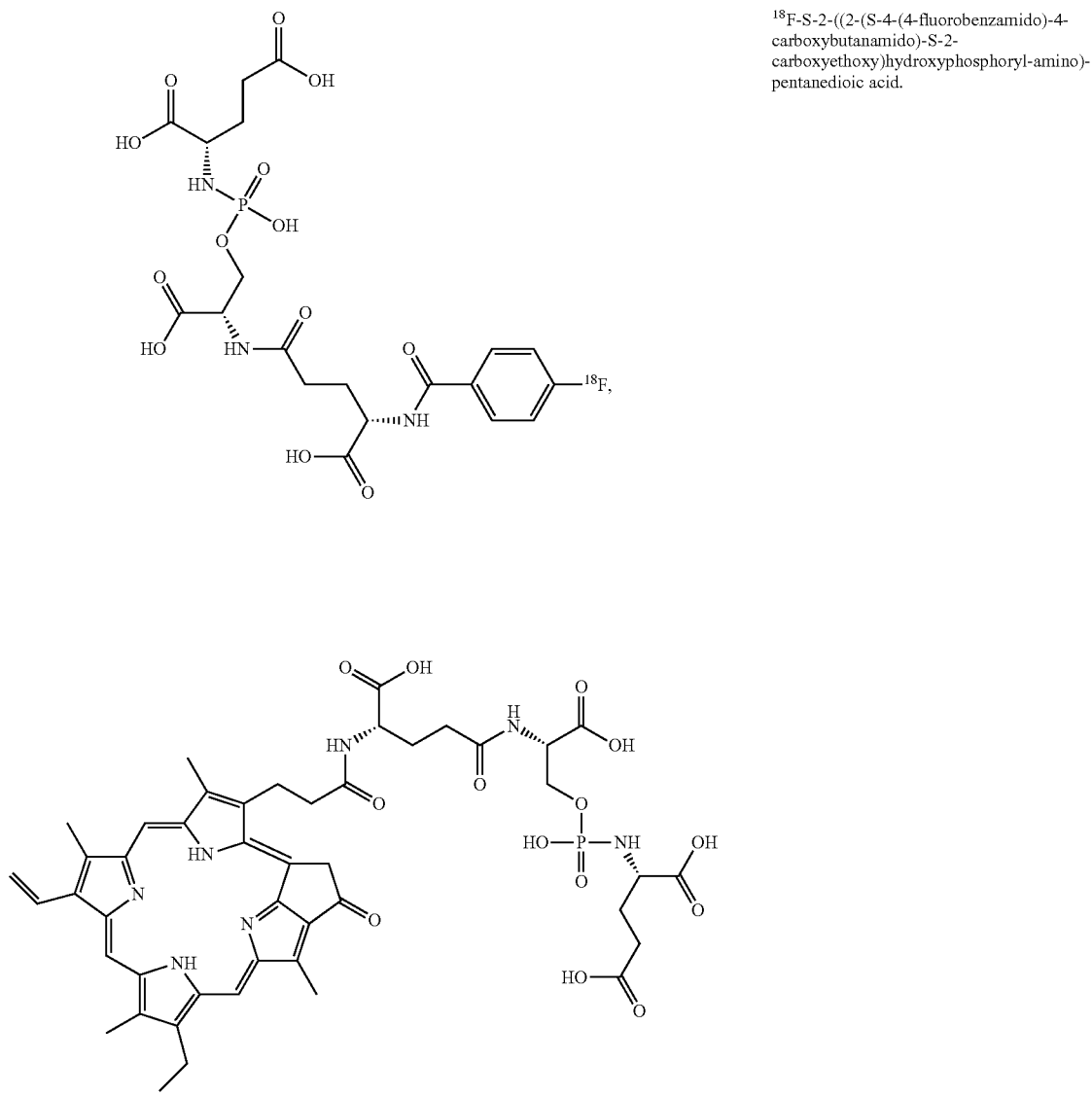
$^{18}$F-S-2-((2-(S-4-(4-fluorobenzamido)-4-carboxybutanamido)-S-2-carboxyethoxy)hydroxyphosphoryl-amino)-pentanedioic acid.

TABLE 1-continued
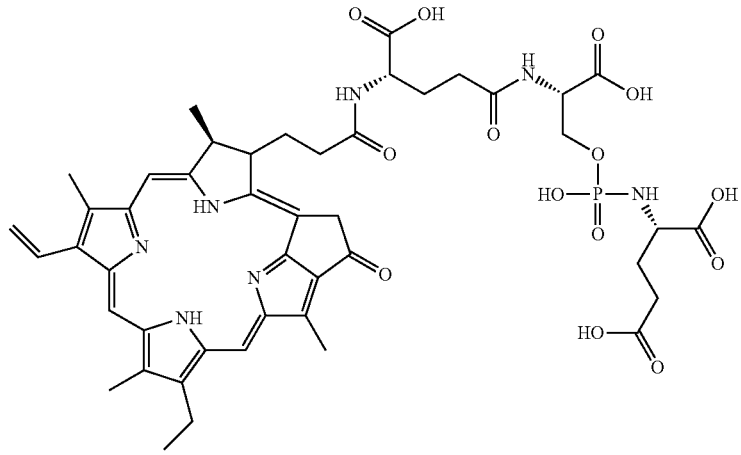 [SMILES: C=CC1=C(C)c2cc3[nH]c(c4c5nc(cc6[nH]c(cc1n2)c(C)c6CC)C(C)=C5C(=O)C4)C(CCC(=O)N[C@@H](CCC(=O)N[C@@H](COP(=O)(O)N[C@@H](CCC(=O)O)C(=O)O)C(=O)O)C(=O)O)[C@@H]3C]
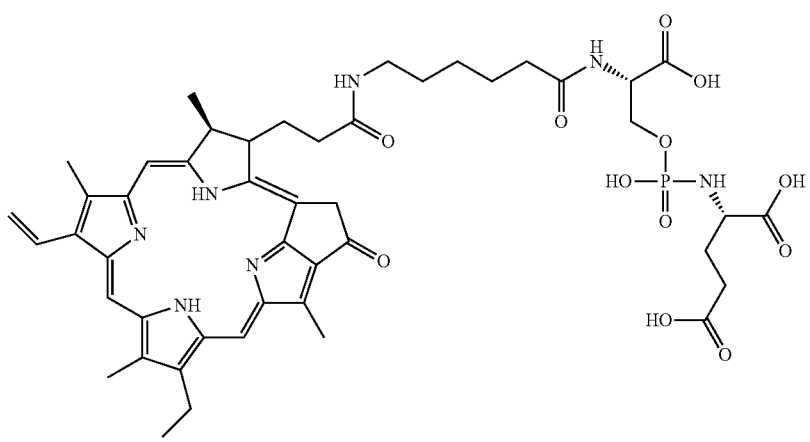 [SMILES: C=CC1=C(C)c2cc3[nH]c(c4c5nc(cc6[nH]c(cc1n2)c(C)c6CC)C(C)=C5C(=O)C4)C(CCC(=O)NCCCCCC(=O)N[C@@H](COP(=O)(O)N[C@@H](CCC(=O)O)C(=O)O)C(=O)O)[C@@H]3C]
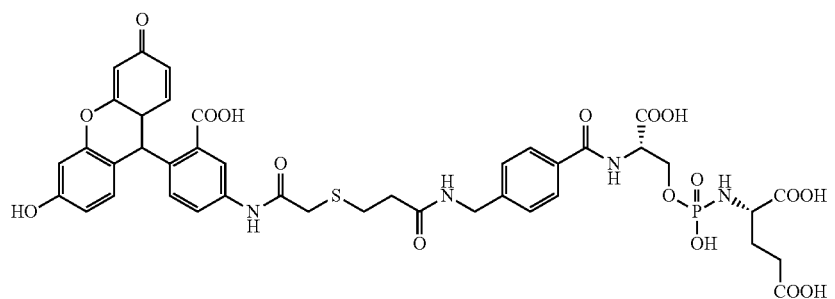 [SMILES: O=C1C=CC2C(=C1)Oc1cc(O)ccc1C2c1ccc(NC(=O)CSCCC(=O)NCc2ccc(C(=O)N[C@@H](COP(=O)(O)N[C@@H](CCC(=O)O)C(=O)O)C(=O)O)cc2)cc1C(=O)O]
N-{[(2S)-2-carboxy-2-({4-[({3-[(2-{[3-carboxy-4-(6-hydroxy-3-oxo-9,9a-dihydro-3H-xanthen-9-yl)phenyl]amino}-2-oxoethyl)thio]propanoyl}amino)methyl]benzoyl}amino)ethoxy](hydroxy)phosphoryl}-L-glutamic acid;
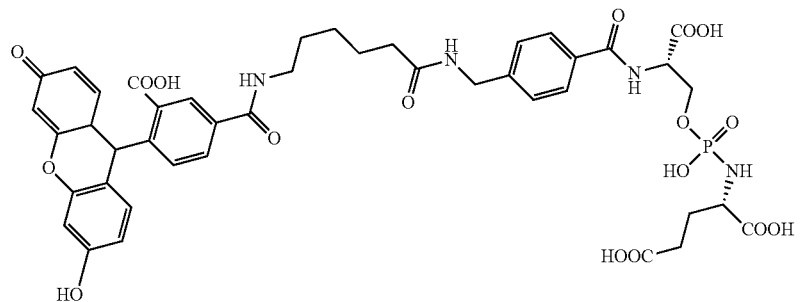 [SMILES: O=C1C=CC2C(=C1)Oc1cc(O)ccc1C2c1ccc(C(=O)NCCCCCC(=O)NCc2ccc(C(=O)N[C@@H](COP(=O)(O)N[C@@H](CCC(=O)O)C(=O)O)C(=O)O)cc2)cc1C(=O)O]
N-[{(2S)-2-carboxy-2-[(4-{[(6-{[3-carboxy-4-(6-hydroxy-3-oxo-9,9a-dihydro-3H-xanthen-9-yl)benzoyl]amino}hexanoyl)amino]methyl}benzoyl)amino]ethoxy}(hydroxy)phosphoryl]-L-glutamic acid;

TABLE 1-continued

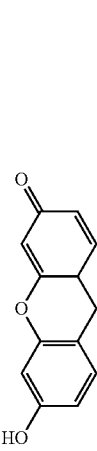

N-{3-[(2-{[3-carboxy-4-(6-hydroxy-3-oxo-9,9a-dihydro-3H-xanthen-9-yl)phenyl]amino}-2-oxoethyl)thio]propanoyl}-L-γ-glutamyl-O-[{[(1S)-1,3-dicarboxypropyl]amino}(hydroxy)phosphoryl]-L-serine;

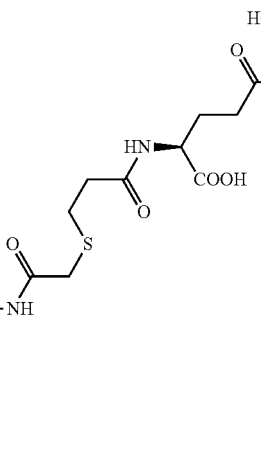

N-(6-{[3-carboxy-4-(6-hydroxy-3-oxo-9,9a-dihydro-3H-xanthen-9-yl)benzoyl]amino}hexanoyl)-L-γ-glutamyl-O-[{[(1S)-1,3-dicarboxypropyl]amino}(hydroxy)phosphoryl]-L-serine;

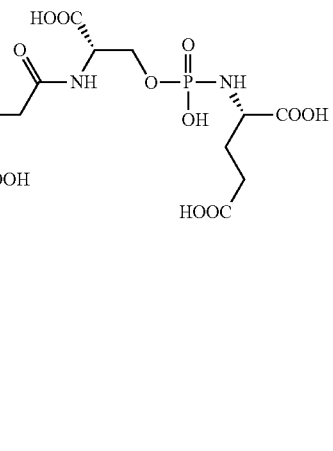

N-[{(2S)-2-carboxy-2-[({[3-carboxy-4-(6-hydroxy-3-oxo-9,9a-dihydro-3H-xanthen-9-yl)phenyl]amino}carbonothioyl)amino]ethoxy}(hydroxy)phosphoryl]-L-glutamic acid;

TABLE 1-continued
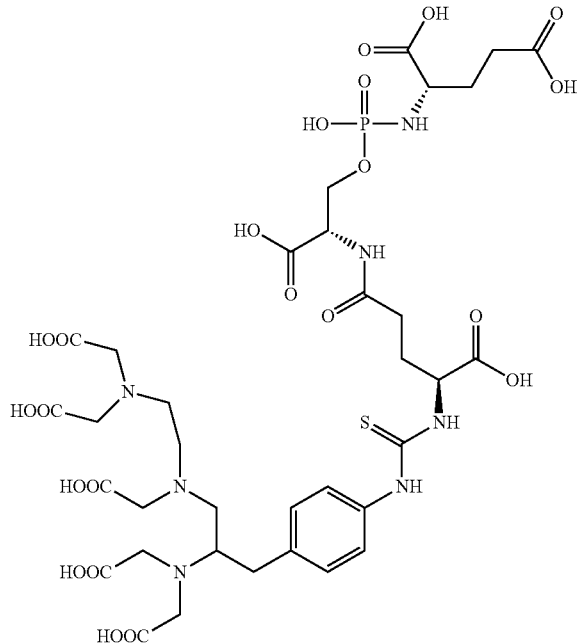 [SMILES: O=C(O)CC[C@H](NP(=O)(O)OC[C@H](NC(=O)CC[C@H](NC(=S)Nc1ccc(CC(CN(CCN(CC(=O)O)CC(=O)O)CC(=O)O)N(CC(=O)O)CC(=O)O)cc1)C(=O)O)C(=O)O)C(=O)O]
N-{[(4-{2-[bis(carboxymethyl)amino]-3-[{2-[bis(carboxymethyl)amino]ethyl}(carboxymethyl)amino]propyl}phenyl)amino]carbonothioyl}-L-γ-glutamyl-O-[{[(1S)-1,3-dicarboxypropyl]amino}(hydroxy)phosphoryl]-L-serine;
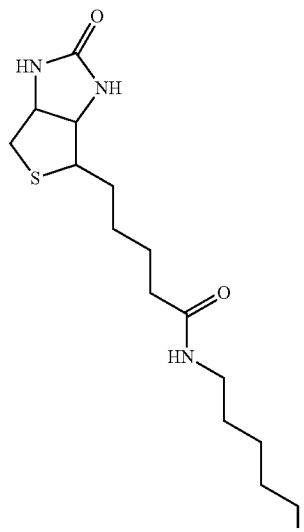
N-{6-[(6-{[5-(2-oxohexahydro-1H-thieno[3,4-d]imidazol-4-yl)pentanoyl]amino}hexanoyl)amino]hexanoyl}-L-γ-glutamyl-O-[{[(1S)-1,3-dicarboxypropyl]amino}(hydroxy)phosphoryl]-L-serine;

TABLE 1-continued
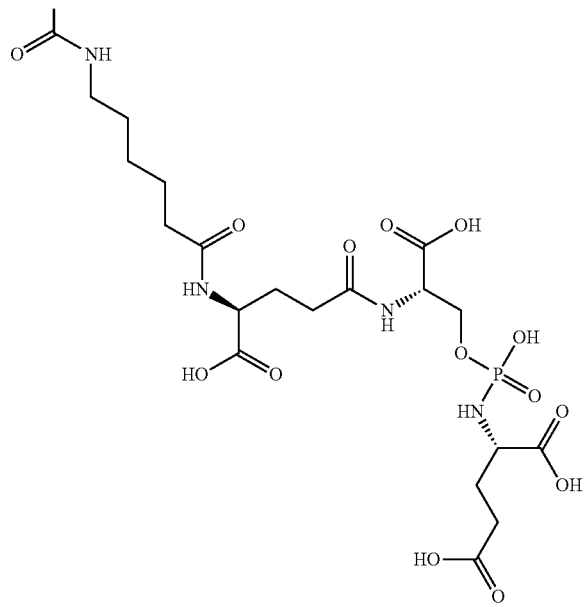
N-{[(2S)-2-carboxy-2-({4-[({6-[(6-{[5-(2-oxohexhydro-1H-thieno[3,4-d]imidazol-4-yl)pentanoyl]amino}hexanoyl)amino]hexanoyl}amino)methyl]benzoyl}amino)ethoxy](hydroxy)phosphoryl}-L-glutamic acid
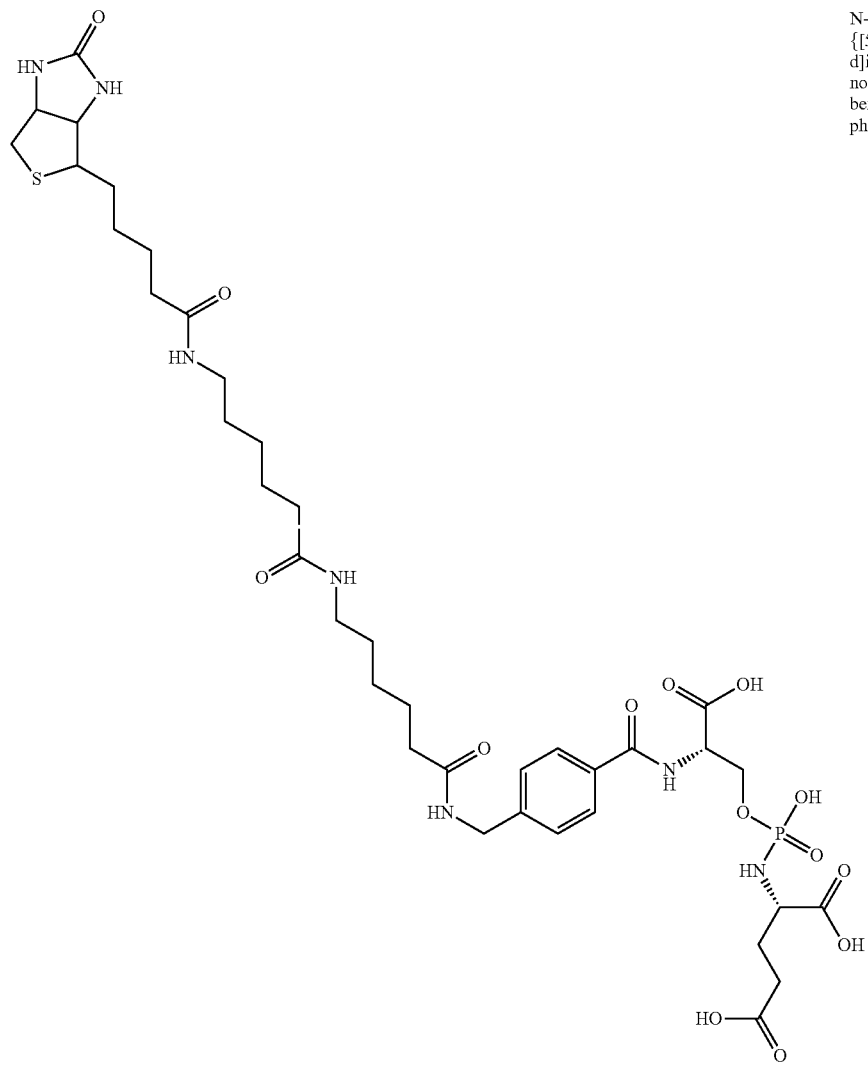 [SMILES: O=C(O)CC[C@H](NP(=O)(O)OC[C@H](NC(=O)c1ccc(CNC(=O)CCCCCNC(=O)CCCCCNC(=O)CCCCC2SCC3NC(=O)NC32)cc1)C(=O)O)C(=O)O]

In an embodiment, the invention comprises the compound of formula (V),

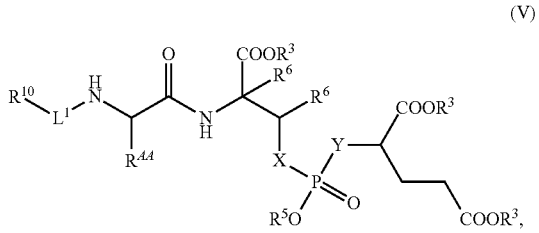

and pharmaceutically acceptable salts thereof, wherein $R^{AA}$, $L^1, X, Y, R^3, R^5, R^6$, and $R^{10}$ are $R^{AA}$ is hydrogen, $C_1$-$C_7$alkyl, aryl, heteroaryl, aryl$C_1$-$C_7$alkyl, or heteroaryl$C_1$-$C_7$alkyl, wherein the alkyl, arylalkyl, and heteroarylalkyl groups are optionally substituted with 1, 2, 3, 4, or 5 $R^{41}$ groups, wherein each $R^{41}$ is independently —$OR^{42}$, —$SR^{42}$, —$N(R^{42})_2$, —$C(O)OR^{42}$, —$C(O)N(R^{42})_2$, —$N(R^{42})C(=NR^{42})N(R^{42})_2$, or $C_1$-$C_7$alkyl, wherein each $R^{42}$ is independently hydrogen or $C_1$-$C_7$alkyl.

$L^1$ is one of groups (5u)-(5z) as defined above for formula (I).

X and Y are one of groups (7a)-(7g) as defined above for formula (I).

each $R^3$ is independently one of groups (9a)-(9e) as defined above for formula (II).

$R^5$ is one of groups (8h)-(8l) as defined above for formula (I).

each $R^6$ is independently one of groups (8m)-(8q) as defined above for formula (I). $R^{10}$ is -aryl-$R^9$, -heteroaryl-$R^9$, —$C_1$-$C_7$alkyl-aryl-$R^9$, —$C_1$-$C_7$alkyl-heteroaryl-$R^9$, —$C_1$-C7alkyl $R^8$, -aryl-$C_1$-$C_7$alkyl-$R^8$, or -heteroaryl-$C_1$-$C_7$alkyl-$R^8$, wherein the aryl, heteroaryl, alkyl-aryl, aryl-alkyl, alkyl-heteroaryl, and heteroaryl-alkyl groups are optionally substituted with one, two, or three groups which are each independently halomethyl, dihalomethyl, trihalomethyl, —$C(O)R^{11}$, —$CO(O)R^{12}$, —$C(O)N(R^{12})_2$, wherein each $R^{11}$ is independently hydrogen, —$C_1$-$C_7$ alkyl, —$C_1$-$C_7$ alkylaryl, or —$C_1$-$C_7$ alkylheteroaryl; and each $R^{12}$ is independently $R^{11}$ or a protecting group;

In an embodiment of any of the preceding embodiments of formulae (I)-(VI), (IIa)-(IIe), (IIIa)-(IIIe), (IVa)-(IVe), (Va)-(Vc), and (VIa)-(VII), $R^9$ can be one of groups (12a)-(12o):

(12a) a detectable label, or a cytotoxic group.
(12b) a detectable label.
(12c) $^{18}F$.
(12d) biotin.
(12e) a cytotoxic group.
(12f) —$N_3$, —C≡CH, —$ONH_2$, —$C(O)N(H)NH_2$, or —$N(H)NH_2$.
(12g) —$N_3$ or —C≡CH.
(12h) —C≡CH.
(12i) —$N_3$.
(12j) a pendant group comprising either a detectable label, or a cytotoxic group.
(12k) a pendant group comprising a detectable label.
(12l) a pendant group comprising a cytotoxic group.
(12m) a pendant group bonded to a solid support.

Suitable detectable labels include, but are not limited to, fluorescent or dichroic dyes; bonded radionuclides; radioisotopes coordinated to a chelating moiety, such as chelated $^{99m}Tc$, $^{64}Cu$, $^{68}Ga$, $^{111}In$, or $^{152}Gd$; chelated MRI contrast agents, such as Gd, Mn, Ba, superparamagnetic iron oxide (SIPO)(e.g., 300-3500 nm, or 60-150 nm diameter particles), ultrasmall superparamagnetic iron oxide (USPIO)(e.g., 10-30 nm diameter particles); and chelated radiotherapeutics, such as $^{177}Lu$ or $^{90}Y$.

Radionuclides useful within the present invention include gamma-emitters, positron-emitters, Auger electron-emitters, X-ray emitters and fluorescence-emitters, with beta- or alpha-emitters preferred for therapeutic use. Examples of useful radionuclides include: $^{18}F$, $^{32}P$, $^{33}P$, $^{43}K$, $^{47}Sc$, $^{52}Fe$, $^{57}Co$, $^{64}Cu$, $^{67}Ga$, $^{67}Cu$, $^{68}Ga$, $^{71}Ge$, $^{75}Br$, $^{76}Br$, $^{77}Br$, $^{77}As$, $^{77}Br$, $^{81}Rb$, $^{81m}Kr$, $^{87m}Sr$, $^{90}Y$, $^{97}Ru$, $^{99m}Tc$, $^{100}Pd$, $^{101}Rh$, $^{103}Pb$, $^{105}Rh$, $^{109}Pd$, $^{111}Ag$, $^{111}In$, $^{113}In$, $^{119}Sb$, $^{121}Sn$, $^{123}I$, $^{125}I$, $^{127}Cs$, $^{128}Ba$, $^{129}Cs$, $^{131}I$, $^{131}Cs$, $^{143}Pr$, $^{153}Sm$, $^{161}Tb$, $^{166}Ho$, $^{169}Eu$, $^{177}Lu$, $^{186}Re$, $^{188}Re$, $^{189}Re$, $^{191}Os$, $^{193}Pt$, $^{194}Ir$, $^{197}Hg$, $^{199}Au$, $^{203}Pb$, $^{211}At$, $^{212}Pb$, $^{212}Bi$ and $^{213}Bi$.

In certain embodiments, the detectable label can be a bonded radionuclide. In one embodiment, the radionuclide is $^{18}F$, $^{123}I$, $^{124}I$, $^{125}I$, or $^{131}I$.

When $R^9$ is a radioisotope, it can be coordinated to a chelating moiety, such as chelated $^{99m}Tc$, $^{64}Cu$, $^{68}Ga$, or $^{111}In$. In certain embodiments, $R^9$ is $^{99m}Tc$ coordinated to a chelating moiety. Moieties which can serve as chelating ligands, include, for example MAG 3 (mercaptoacetyltriglycine) or bispicol ylamine (SAAC); derivatives of 1,4,7,10-tetraazacyclododecanetetraacetic acid (DOTA), ethylenediaminetetraacetic acid (EDTA), diethylenetriaminepentaacetic acid (DTPA) and 1-p-Isothio cyanato-benzyl-methyl-diethylenetriaminepentaacetic acid (ITC-MX). These chelators typically have groups on the side chain by which the chelator can be used for attachment to a parent molecule. Such groups include, e.g., benzylisothiocyanate, by which the MAG 3, SAAC, DOTA, DTPA, NOTA, CHX-A' or EDTA can be coupled to, e.g., an amine group of the parent molecule.

In another embodiment, the $^{18}F$ in the $^{18}F$-containing structures displayed hereinabove can be replaced with another radionuclide disclosed herein.

Suitable cytotoxic groups include, but are not limited to chelated or bonded radiotherapeutics, photosensitizers, small molecule agents such as paclitaxel, camptothecin, and doxorubicin, as well as lysosomal disrupting agents, such as, $^{125}I$, $^{131}I$, $^{177}Lu$, $^{168}Rh$, or $^{90}Y$.

An example of a $^{18}F$-labeled peptide analog of CTT-54 which could be made is a pharmaceutically acceptable salt of,

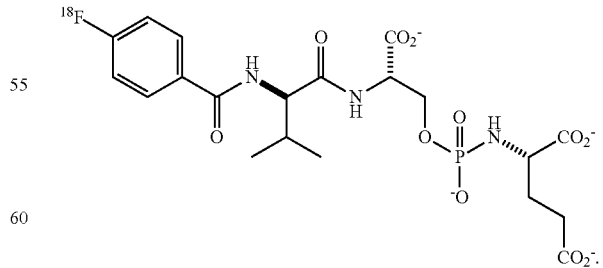

Exemplary cold compounds which could be 18F labeled were examined using the assay described in U.S. Pat. No. 7,696,185 to Berkman which is herein incorporated by reference.

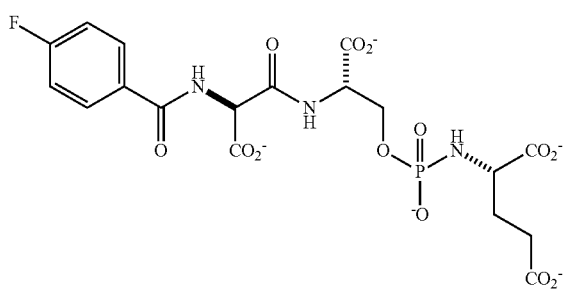

SFB-CTT-54
IC$_{50}$ = 1.4 nM

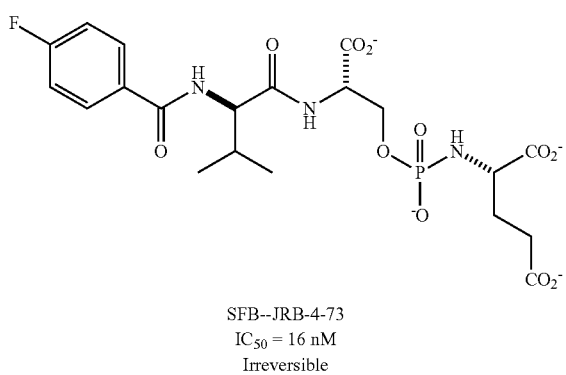

SFB--JRB-4-73
IC$_{50}$ = 16 nM
Irreversible

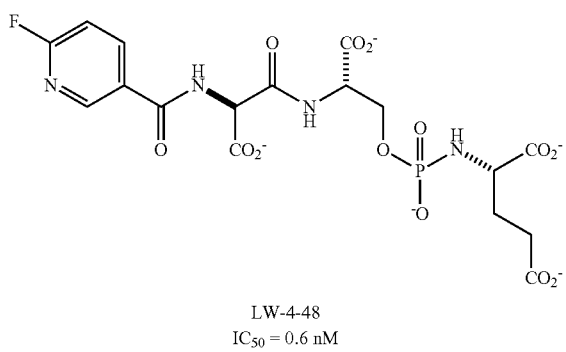

LW-4-48
IC$_{50}$ = 0.6 nM

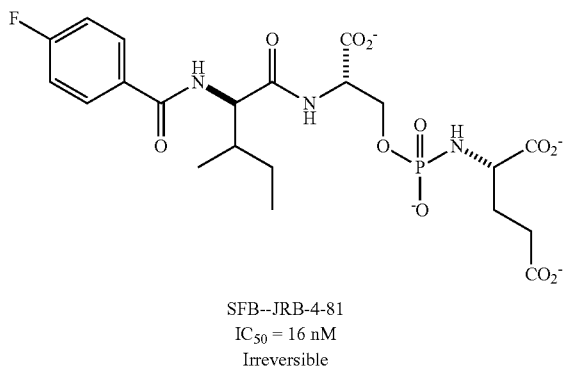

SFB--JRB-4-81
IC$_{50}$ = 16 nM
Irreversible

These results are consistent with those observed for the SFB-CTT-54 conjugate initially described in "Assessment of an $^{18}$F-labeled phosphoramidate peptidomimetic as a new prostate-specific membrane antigen-targeted imaging agent for prostate cancer". Lapi, S. E., et al., J. Nucl. Med. 2009, 50(12), 2042-8, which is hereby incorporated by reference in its entirety. The heteroatomic ring (nicotinamide) did not diminish the PSMA binding observed for the SFB-CTT-54. Unexpectedly, the IC$_{50}$ for the fluoronicotinamide (LW-4-48) was found to be 0.6 nM, an approximately three-fold improvement over the preceding fluorobenzamide (SFB-CTT-54).

DEFINITIONS

A "polypeptide of 1-20 amino acids" as used herein means a linear polypeptide wherein each of the amino acids are naturally occurring or non-naturally occurring (e.g., D-amino acids, beta amino acids, beta and gamma-linked aspartate and glutamate). In certain embodiments, each of the amino acids is naturally occurring (L-amino acids). For example, a polypeptide can have the following structure, —[N(R$^N$)—C(H)(R$^A$)—C(O)]$_r$—, wherein —C(O)R$^{10}$ is connected to the N-terminus;

r is selected from 1 to 20;

each R$^A$ is independently hydrogen, C$_1$-C$_7$alkyl, aryl, heteroaryl, arylC$_1$-C$_7$alkyl, or heteroarylC$_1$-C$_7$alkyl, wherein the alkyl, arylalkyl, and heteroarylalkyl groups are optionally substituted with 1, 2, 3, 4, or 5 R$^{410}$ groups, wherein each R$^{410}$ is independently —OR$^{420}$, —SR$^{420}$, —N(R$^{420}$)$_2$, —C(O)OR$^{420}$, —C(O)N(R$^{420}$)$_2$, —N(R$^{420}$)C(=NR$^{420}$)N(R$^{420}$)$_2$, or C$_1$-C$_7$alkyl, wherein each R$^{420}$ is independently hydrogen or C$_1$-C$_7$alkyl; and each R$^N$ is hydrogen, or any R$^A$ and R$^N$ within the same subunit can be taken together with the atoms to which they are attached to form a 5 membered heterocyclyl.

"Protecting groups" include, but are not limited to substituted benzyl, t-butyl ester, alkyl esters (e.g., methyl, ethyl), and fluorenylmethoxycarbonyl groups as described in Greene's Protective Groups in Organic Synthesis, 4th Edition for protecting groups of carboxylic and phosphorus acids. Substituted benzyl groups include, but are not limited to, triphenylmethyl (trityl), diphenylmethyl, o-nitrobenzyl, 2,4,6-trimethylbenzyl, p-bromobenzyl, p-nitrobenzyl, p-methoxybenzyl, 2,6-dimethoxybenzyl, 4-(methylsulfinyl)benzyl, 4-sulfobenzyl, 4-azidomethoxybenzyl, and piperonyl, and other teachings relating to carboxylate protecting groups of Greene's Protective Groups in Organic Synthesis (included, without limitation, the identity of such groups and methods of their use) is hereby incorporated by reference in their entirety.

A "pendant group" as used herein means a group of the formula,

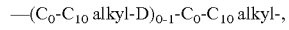

—(C$_0$-C$_{10}$ alkyl-D)$_{0-1}$-C$_0$-C$_{10}$ alkyl-, wherein D is a bond, aryl, heteroaryl, C$_3$-C$_8$ cycloalkyl, or heterocyclyl; and no more than one methylene in each alkyl group is optionally and independently replaced by —O—, —S—, —N(R$^{00}$)—, —C(H)=C(H)—, —C≡C—, —C(O)—, —S(O)—, —S(O)$_2$—, —P(O)(OH)—, —OP(O)(OH)—, —P(O)(OH)O—, —N(R$^{00}$)P(O)(OH)—, —P(O)(OH)N(R$^{00}$)—, —OP(O)(OH)O—, —OP(O)(OH)N(R$^{00}$)—, —N(R$^{00}$)P(O)(OH)O—, —N(R$^{00}$)P(O)(OH)N(R$^{00}$)—, —C(O)O—, —C(O)N(R$^{00}$)—, —OC(O)—, —N(R$^{00}$)C(O)—, —S(O)O—, —OS(O)—, —S(O)N(R$^{00}$)—, —N(R$^{00}$)S(O)—, —S(O)$_2$O—, —OS(O)$_2$—, —S(O)$_2$N(R$^{00}$)—, —N(R$^{00}$)S(O)$_2$—, OC(O)O—, —OC(O)N(R$^{00}$)—, —N(R$^{00}$)C(O)O—, —N(R$^{00}$)C(O)N(R$^{00}$)—, —OS(O)O—, —OS(O)N(R$^{00}$)—, —N(R$^{00}$)S(O)O—, —N(R$^{00}$)S(O)N(R$^{00}$)—, —OS(O)$_2$O—, —OS(O)$_2$N(R$^{00}$)—, —N(R$^{00}$)S(O)$_2$O—, or —N(R$^{00}$)S(O)$_2$N(R$^{00}$)—, wherein each R$^{00}$ is independently hydrogen or C$_1$-C$_7$ alkyl.

Particular embodiments of a "pendant group" as used herein include groups of the formula, —(C$_0$-C$_{10}$ alkyl-D)$_{0-1}$-C$_0$-C$_{10}$ alkyl-, wherein
(1) D is aryl, heteroaryl, $C_3$-$C_8$ cycloalkyl, or heterocyclyl; and no more than one methylene in each alkyl group is optionally and independently replaced by —O—, —S—, —N($R^{oo}$)—, —C(H)=C(H)—, —C≡C—, —C(O)—, —S(O)—, —S(O)$_2$—, —C(O)O—, —C(O)N($R^{oo}$)—, —OC(O)—, —N($R^{oo}$)C(O)—, —S(O)$_2$O—, —OS(O)$_2$—, —S(O)$_2$N($R^{oo}$)—, —N($R^{oo}$)S(O)$_2$—, —OC(O))—, —OC(O)N($R^{oo}$)—, —N($R^{oo}$)C(O)O—, —N($R^{oo}$)C(O)N($R^{oo}$)—, —OS(O)$_2$O—, —OS(O)$_2$N($R^{oo}$)—, —N($R^{oo}$)S(O)$_2$O—, or —N($R^{oo}$)S(O)$_2$N($R^{oo}$)—, wherein each $R^{oo}$ is independently hydrogen or $C_1$-$C_7$ alkyl; or
(2) D is aryl or heteroaryl; and no more than one methylene in each alkyl group is optionally and independently replaced by —O—, —S—, —N($R^{oo}$)—, —C(H)=C(H)—, —C(O)—, —S(O)—, —S(O)$_2$—, —C(O)O—, —C(O)N($R^{oo}$)—, —OC(O)—, —N($R^{oo}$)C(O)—, —OC(O)O—, —OC(O)N($R^{oo}$)—, —N($R^{oo}$)C(O)O—, or —N($R^{oo}$)C(O)N($R^{oo}$)—, wherein each $R^{oo}$ is independently hydrogen or $C_1$-$C_7$ alkyl; or
(3) D is aryl or heteroaryl; and no more than one methylene in each alkyl group is optionally and independently replaced by —O—, —S—, —N($R^{oo}$)—, —C(O)—, —S(O)$_2$—, —C(O)O—, —C(O)N($R^{oo}$)—, —OC(O)—, or —N($R^{oo}$)C(O)—, wherein each $R^{oo}$ is independently hydrogen or $C_1$-$C_7$ alkyl.

Particular embodiments of a "pendant group" also includes a group of the formula, —$C_0$-$C_{10}$ alkyl-, wherein no more than one methylene in the alkyl group is optionally replaced by —O—, —S—, —N($R^{oo}$)—, —C(H)=C(H)—, —C≡C—, —C(O)—, —S(O)—, —S(O)$_2$—, —P(O)(OH)—, —OP(O)(OH)—, —P(O)(OH)O—, —N($R^{oo}$)P(O)(OH)—, —P(O)(OH)N($R^{oo}$)—, —OP(O)(OH)O—, —OP(O)(OH)N($R^{oo}$)—, —N($R^{oo}$)P(O)(OH)O—, —N($R^{oo}$)P(O)(OH)N($R^{oo}$)—, —C(O)O—, —C(O)N($R^{oo}$)—, —OC(O)—, —N($R^{oo}$)C(O)—, —S(O)O—, —OS(O)—, —S(O)N($R^{oo}$)—, —N($R^{oo}$)S(O)—, —S(O)$_2$O—, —OS(O)$_2$—, —S(O)$_2$N($R^{oo}$)—, —N($R^{oo}$)S(O)$_2$—, OC(O)O—, —OC(O)N($R^{oo}$)—, —N($R^{oo}$)C(O)O—, —N($R^{oo}$)C(O)N($R^{oo}$)—, —OS(O)O—, —OS(O)N($R^{oo}$)—, —N($R^{oo}$)S(O)O—, —N($R^{oo}$)S(O)N($R^{oo}$)—, —OS(O)$_2$O—, —OS(O)$_2$N($R^{oo}$)—, —N($R^{oo}$)S(O)$_2$O—, or —N($R^{oo}$)S(O)$_2$N($R^{oo}$)—, wherein each $R^{oo}$ is independently hydrogen or $C_1$-$C_7$ alkyl.

Particular embodiments of a "pendant group" also includes a group of the formula, —$C_1$-$C_{10}$ alkyl-, wherein
(1) no more than one methylene in the alkyl group is optionally replaced by —O—, —S—, —N($R^{oo}$)—, —C(O)—, S(O)$_2$—, —C(O)O—, —C(O)N($R^{oo}$)—, —OC(O)—, —N($R^{oo}$)C(O)—, —S(O)$_2$N($R^{oo}$)—, —N($R^{oo}$)S(O)$_2$—, —OC(O)O—, —OC(O)N($R^{oo}$)—, —N($R^{oo}$)C(O)O—, or —N($R^{oo}$)C(O)N($R^{oo}$)—, wherein each $R^{oo}$ is independently hydrogen or $C_1$-$C_7$ alkyl;
or (2) no more than one methylene in the alkyl group is optionally replaced by —C(O)O—, —C(O)N($R^{oo}$)—, —OC(O)—, —N($R^{oo}$)C(O)—, —OC(O)O—, —OC(O)N($R^{oo}$)—, —N($R^{oo}$)C(O)O—, or —N($R^{oo}$)C(O)N($R^{oo}$)—, wherein each $R^{oo}$ is independently hydrogen or $C_1$-$C_7$ alkyl; or (3) no more than one methylene in the alkyl group is optionally replaced by —C(O)O—, —C(O)N($R^{oo}$)—, —OC(O)—, or —N($R^{oo}$)C(O)—, wherein each $R^{oo}$ is independently hydrogen or $C_1$-$C_7$ alkyl.

Particular embodiments of a "pendant group" also includes a group of the formula, -J-$C_0$-$C_{10}$ alkyl-, wherein
(1) J is —O—, —S—, —C(H)=C(H)—, —C(O)—, —S(O)—, —S(O)$_2$—, —P(O)(OH)—, —OP(O)(OH)—, —P(O)(OH)O—, —N($R^{oo}$)P(O)(OH)—, —P(O)(OH)N($R^{oo}$)—, —OP(O)(OH)O—, —OP(O)(OH)N($R^{oo}$)—, —N($R^{oo}$)P(O)(OH)O—, —N($R^{oo}$)P(O)(OH)N($R^{oo}$)—, —C(O)O—, —C(O)N($R^{oo}$)—, —OC(O)—, —N($R^{oo}$)C(O)—, —S(O)O—, —OS(O)—, —S(O)N($R^{oo}$)—, —N($R^{oo}$)S(O)—, —S(O)$_2$O—, —OS(O)$_2$—, —S(O)$_2$N($R^{oo}$)—, —N($R^{oo}$)S(O)$_2$—, —OC(O)O—, —OC(O)N($R^{oo}$)—, —N($R^{oo}$)C(O)O—, —N($R^{oo}$)C(O)N($R^{oo}$)—, —OS(O)O—, —OS(O)N($R^{oo}$)—, —N($R^{oo}$)S(O)O—, —N($R^{oo}$)S(O)N($R^{oo}$)—, —OS(O)$_2$—, —OS(O)$_2$N($R^{oo}$)—, —N($R^{oo}$)S(O)$_2$O—, or —N($R^{oo}$)S(O)$_2$N($R^{oo}$)—, wherein each $R^{oo}$ is independently hydrogen or $C_1$-$C_7$ alkyl, and wherein J is bonded to the moiety substituted by the pendant group;
or (2) J is —O—, —S—, —C(O)—, S(O)$_2$—, —C(O)O—, —C(O)N($R^{oo}$)—, —OC(O)—, —N($R^{oo}$)C(O)—, —S(O)$_2$N($R^{oo}$)—, —N($R^{oo}$)S(O)$_2$—, —OC(O)O—, —OC(O)N($R^{oo}$)—, —N($R^{oo}$)C(O)O—, or —N($R^{oo}$)C(O)N($R^{oo}$)—, wherein each $R^{oo}$ is independently hydrogen or $C_1$-$C_7$ alkyl, and wherein J is bonded to the moiety substituted by the pendant group;
or (3) J is —C(O)O—, —C(O)N($R^{oo}$)—, —OC(O)—, —N($R^{oo}$)C(O)—, —OC(O)O—, —OC(O)N($R^{oo}$)—, —N($R^{oo}$)C(O)O—, or —N($R^{oo}$)C(O)N($R^{oo}$)—, wherein each $R^{oo}$ is independently hydrogen or $C_1$-$C_7$ alkyl, and wherein J is bonded to the moiety substituted by the pendant group;
or (4) J is —C(O)O—, —C(O)N($R^{oo}$)—, —OC(O)—, or —N($R^{oo}$)C(O)—, wherein each $R^{oo}$ is independently hydrogen or $C_1$-$C_7$ alkyl, and wherein J is bonded to the moiety substituted by the pendant group;
or (5) J is —C(O)N($R^{oo}$)— or —N($R^{oo}$)C(O)—, wherein $R^{oo}$ is hydrogen or $C_1$-$C_7$ alkyl, and wherein J is bonded to the moiety substituted by the pendant group.

Particular embodiments of a "pendant group" also includes a group of the formula, —C(O)N($R^{oo}$)—$C_0$-$C_{10}$ alkyl-, wherein $R^{oo}$ is hydrogen or $C_1$-$C_7$ alkyl, and wherein the amide carbonyl is bonded to the moiety substituted by the pendant group.

Particular embodiments of a "pendant group" also includes a group of the formula, —N($R^{oo}$)C(O)—$C_0$-$C_{10}$ alkyl-, wherein $R^{oo}$ is hydrogen or $C_1$-$C_7$ alkyl, and wherein the amide nitrogen is bonded to the moiety substituted by the pendant group.

A "pendant group comprising a detectable label, or a cytotoxic group" as used herein means a group of the formula -L-$R^o$, wherein L is any of the preceding pendant groups as defined herein and $R^o$ is a detectable label, or a cytotoxic group, each as defined above.

A "pendant group bonded to a solid support" as used herein means a group of the formula, -L-$R^o$, wherein L is any of the preceding pendant groups, as defined herein, and $R^o$ is the surface of a solid support. Examples of solid supports include, but are not limited to, a resin, a polymer, or a silica.

The term "alkyl" as used herein, means a straight or branched chain hydrocarbon containing from 1 to 10 carbon atoms, unless otherwise specified. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2- dimethylpentyl, 2,3-dimethylpentyl, n-heptyl, n-octyl, n-nonyl, and n-decyl. When an "alkyl" group is a linking group between two other moieties, then it may also be a straight or branched chain; examples include, but are not limited to —CH$_2$—, —CH$_2$CH$_2$—, —CH$_2$CH$_2$CHC(CH$_3$)—, —CH$_2$CH(CH$_2$CH$_3$)CH$_2$—.

The term "aryl," as used herein, means a phenyl (i.e., monocyclic aryl), or a bicyclic ring system containing at least one phenyl ring or an aromatic bicyclic ring containing only carbon atoms in the aromatic bicyclic ring system. The bicyclic aryl can be azulenyl, naphthyl, or a phenyl fused to a monocyclic cycloalkyl, a monocyclic cycloalkenyl, or a monocyclic heterocyclyl. The bicyclic aryl is attached to the parent molecular moiety through any carbon atom contained within the phenyl portion of the bicyclic system, or any carbon atom with the napthyl or azulenyl ring. The fused monocyclic cycloalkyl or monocyclic heterocyclyl portions of the bicyclic aryl are optionally substituted with one or two oxo and/or thia groups. Representative examples of the bicyclic aryls include, but are not limited to, azulenyl, naphthyl, dihydroinden-1-yl, dihydroinden-2-yl, dihydroinden-3-yl, dihydroinden-4-yl, 2,3-dihydroindol-4-yl, 2,3-dihydroindol-5-yl, 2,3-dihydroindol-6-yl, 2,3-dihydroindol-7-yl, inden-1-yl, inden-2-yl, inden-3-yl, inden-4-yl, dihydronaphthalen-2-yl, dihydronaphthalen-3-yl, dihydronaphthalen-4-yl, dihydronaphthalen-1-yl, 5,6,7,8-tetrahydronaphthalen-1-yl, 5,6,7,8-tetrahydronaphthalen-2-yl, 2,3-dihydrobenzo furan-4-yl, 2,3-dihydrobenzofuran-5-yl, 2,3-dihydrobenzofuran-6-yl, 2,3-dihydrobenzofuran-7-yl, benzo[d][1,3]dioxol-4-yl, benzo[d][1,3]dioxol-5-yl, 2H-chromen-2-on-5-yl, 2H-chromen-2-on-6-yl, 2H-chromen-2-on-7-yl, 2H-chromen-2-on-8-yl, isoindoline-1,3-dion-4-yl, isoindoline-1,3-dion-5-yl, inden-1-on-4-yl, inden-1-on-5-yl, inden-1-on-6-yl, inden-1-on-7-yl, 2,3-dihydrobenzo[b][1,4]dioxan-5-yl, 2,3-dihydrobenzo[b][1,4]dioxan-6-yl, 2H-benzo[b][1,4]oxazin3 (4H)-on-5-yl, 2H-benzo[b][1,4]oxazin3 (4H)-on-6-yl, 2H-benzo[b][1,4]oxazin3 (4H)-on-7-yl, 2H-benzo[b][1,4]oxazin3 (4H)-on-8-yl, benzo[d]oxazin-2(3H)-on-5-yl, benzo[d]oxazin-2(3H)-on-6-yl, benzo[d]oxazin-2(3H)-on-7-yl, benzo[d]oxazin-2(3H)-on-8-yl, quinazolin-4(3H)-on-5-yl, quinazolin-4(3H)-on-6-yl, quinazolin-4(3H)-on-7-yl, quinazolin-4(3H)-on-8-yl, quinoxalin-2(1H)-on-5-yl, quinoxalin-2(1H)-on-6-yl, quinoxalin-2(1H)-on-7-yl, quinoxalin-2(1H)-on-8-yl, benzo[d]thiazol-2(3H)-on-4-yl, benzo[d]thiazol-2(3H)-on-5-yl, benzo[d]thiazol-2(3H)-on-6-yl, and, benzo[d]thiazol-2(3H)-on-7-yl. In certain embodiments, the bicyclic aryl is (i) naphthyl or (ii) a phenyl ring fused to either a 5 or 6 membered monocyclic cycloalkyl, a 5 or 6 membered monocyclic cycloalkenyl, or a 5 or 6 membered monocyclic heterocyclyl, wherein the fused cycloalkyl, cycloalkenyl, and heterocyclyl groups are optionally substituted with one or two groups which are independently oxo or thia.

The term "arylalkyl" and "-alkylaryl" as used herein, means an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

The term "cycloalkyl" as used herein, means a monocyclic or a bicyclic cycloalkyl ring system. Monocyclic ring systems are cyclic hydrocarbon groups containing from 3 to 8 carbon atoms, where such groups can be saturated or unsaturated, but not aromatic. In certain embodiments, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. Bridged monocyclic rings contain a monocyclic cycloalkyl ring where two non-adjacent carbon atoms of the monocyclic ring are linked by an alkylene bridge of between one and three additional carbon atoms (i.e., a bridging group of the form —(CH$_2$)$_w$—, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. The bridged or fused bicyclic cycloalkyl is attached to the parent molecular moiety through any carbon atom contained within the monocyclic cycloalkyl ring. Cycloalkyl groups are optionally substituted with one or two groups which are independently oxo or thia. In certain embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted by one or two groups which are independently oxo or thia.

"Cycloalkenyl" as used herein refers to a monocyclic or a bicyclic cycloalkenyl ring system. Monocyclic ring systems are cyclic hydrocarbon groups containing from 3 to 8 carbon atoms, where such groups are unsaturated (i.e., containing at least one annular carbon-carbon double bond), but not aromatic. Examples of monocyclic ring systems include cyclopentenyl and cyclohexenyl. Bicyclic cycloalkenyl rings are bridged monocyclic rings or a fused bicyclic rings. Bridged monocyclic rings contain a monocyclic cycloalkenyl ring where two non-adjacent carbon atoms of the monocyclic ring are linked by an alkylene bridge of between one and three additional carbon atoms (i.e., a bridging group of the form —(CH$_2$)$_w$—, where w is 1, 2, or 3). Representative examples of bicycliC cycloalkenyls include, but are not limited to, norbornenyl and bicyclo[2.2.2]oct-2-enyl. Fused bicyclic cycloalkenyl ring systems contain a monocyclic cycloalkenyl ring fused to either a phenyl, a monocyclic cycloalkyl, a monocyclic cycloalkenyl, a monocyclic heterocyclyl, or a monocyclic heteroaryl. The bridged or fused bicyclic cycloalkenyl is attached to the parent molecular moiety through any carbon atom contained within the monocyclic cycloalkenyl ring. Cycloalkenyl groups are optionally substituted with one or two groups which are independently oxo or thia.

The term "halo" or "halogen" as used herein, means —Cl, —Br, —I or —F.

The term "haloalkyl" as used herein, means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoro ethyl, and 2-chloro-3-fluoropentyl.

The term "haloalkylcarbonyloxy" as used herein means a group of the formula —OC(O)R, where R is a haloalkyl group as defined herein.

The term "heteroaryl," as used herein, means a monocyclic heteroaryl or a bicyclic ring system containing at least one heteroaromatic ring. The monocyclic heteroaryl can be a 5 or 6 membered ring. The 5 membered ring consists of two double bonds and one, two, three or four nitrogen atoms and optionally one oxygen or sulfur atom. The 6 membered ring consists of three double bonds and one, two, three or four nitrogen atoms. The 5 or 6 membered heteroaryl is connected to the parent molecular moiety through any carbon atom or any nitrogen atom contained within the heteroaryl. Representative examples of monocyclic heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl fused to a phenyl, a monocyclic cycloalkyl, a monocyclic cycloalkenyl, a monocyclic heterocyclyl, or a monocyclic heteroaryl. The fused cycloalkyl or heterocyclyl portion of the bicyclic heteroaryl group is optionally substituted with one or two groups which are independently oxo or thia. When the bicyclic heteroaryl contains a fused cycloalkyl, cycloalkenyl, or heterocyclyl ring, then the bicyclic heteroaryl group is connected to the parent molecular moiety through any carbon or nitrogen atom contained within the monocyclic heteroaryl portion of the bicyclic ring system. When the bicyclic heteroaryl is a monocyclic heteroaryl fused to a phenyl ring, then the bicyclic heteroaryl group is connected to the parent molecular moiety through any carbon atom or nitrogen atom within the bicyclic ring system. Representative examples of bicyclic heteroaryl include, but are not limited to, benzimidazolyl, benzofuranyl, benzothienyl, benzoxadiazolyl, benzoxathiadiazolyl, benzothiazolyl, cinnolinyl, 5,6-dihydroquinolin-2-yl, 5,6-dihydroisoquinolin-1-yl, furopyridinyl, indazolyl, indolyl, isoquinolinyl, naphthyridinyl, quinolinyl, purinyl, 5,6,7,8-tetrahydroquinolin-2-yl, 5,6,7,8-tetrahydroquinolin-3-yl, 5,6,7,8-tetrahydroquinolin-4-yl, 5,6,7,8-tetrahydroisoquinolin-1-yl, thienopyridinyl, 4,5,6,7-tetrahydrobenzo[c][1,2,5]oxadiazolyl, and 6,7-dihydrobenzo[c][1,2,5]oxadiazol-4(5H)-onyl. In certain embodiments, the fused bicyclic heteroaryl is a 5 or 6 membered monocyclic heteroaryl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused cycloalkyl, cycloalkenyl, and heterocyclyl groups are optionally substituted with one or two groups which are independently oxo or thia.

The term "heteroarylalkyl" and "-alkylheteroaryl" as used herein, means a heteroaryl, as defined herein, appended to the parent molecular moiety through an alkyl group, as defined herein. Representative examples of heteroarylalkyl include, but are not limited to, fur-3-ylmethyl, 1H-imidazol-2-ylmethyl, 1H-imidazol-4-ylmethyl, 1-(pyridin-4-yl)ethyl, pyridin-3-ylmethyl, pyridin-4-ylmethyl, pyrimidin-5-ylmethyl, 2-(pyrimidin-2-yl)propyl, thien-2-ylmethyl, and thien-3-ylmethyl.

The term "heterocyclyl" as used herein, means a monocyclic heterocycle or a bicyclic heterocycle. The monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of 0, N and S. The 6 or 7 membered ring contains zero, one or two double bonds and one, two or three heteroatoms selected from the group consisting of O, N and S. The monocyclic heterocycle is connected to the parent molecular moiety through any carbon atom or any nitrogen atom contained within the monocyclic heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3 imidazolinyl, isothiazolinyl, isothiazolidinyl isoxazolinyl, isoxazolidinyl, morpholinyl, oxadiazolinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiazolinyl, thiazolidinyl, thiomorpholinyl, 1,1-dioxido thiomorpholinyl (thiomorpholine sulfone), thiopyranyl, and trithianyl. The bicyclic heterocycle is a monocyclic heterocycle fused to either a phenyl, a monocyclic cycloalkyl, a monocyclic cycloalkenyl, a monocyclic heterocycle, or a monocyclic heteroaryl. The bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. Heterocyclyl groups are optionally substituted with one or two groups which are independently oxo or thia. In certain embodiments, the bicyclic heterocyclyl is a 5 or 6 membered monocyclic heterocyclyl ring fused to phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thia.

The term "oxo" as used herein means a =O group.

The term "saturated" as used herein means the referenced chemical structure does not contain any multiple carbon-carbon bonds. For example, a saturated cycloalkyl group as defined herein includes cyclohexyl, cyclopropyl, and the like.

The term "thia" as used herein means a =S group.

The term "unsaturated" as used herein means the referenced chemical structure contains at least one multiple carbon-carbon bond, but is not aromatic. For example, a unsaturated cycloalkyl group as defined herein includes cyclohexenyl, cyclopentenyl, cyclohexadienyl, and the like.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" PSMA with a compound includes the administration of a compound described herein to an individual or patient, such as a human, as well as, for example, introducing a compound into a sample containing a cellular or purified preparation containing PMSA.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician, which includes one or more of the following, as the case may be:

(1) preventing the disease; for example, preventing a disease, condition or disorder in an individual who may be predisposed to the disease, condition or disorder but does not yet experience or display the pathology or symptomatology of the disease;
(2) inhibiting the disease; for example, inhibiting a disease, condition or disorder in an individual who is experiencing or displaying the pathology or symptomatology of the disease, condition or disorder; and
(3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

Whether the therapeutically effective amount is for prevention, inhibitions, or amelioration will be clear from the context.

As used here, the terms "treatment" and "treating" means ameliorating the referenced disease state, for example, ameliorating a disease, condition or disorder in an individual who is experiencing or displaying the pathology or symptomatology of the disease, condition or disorder (i.e., reversing or improving the pathology and/or symptomatology) such as decreasing the severity of disease.

As used herein, the phrase "pharmaceutically acceptable salt" refers to both pharmaceutically acceptable acid and base addition salts and solvates. Such pharmaceutically acceptable salts include salts of acids such as hydrochloric, phosphoric, hydrobromic, sulfuric, sulfinic, toluenesulfonic, methanesulfonic, nitric, benzoic, citric, tartaric, maleic, hydroiodic, alkanoic such as acetic, $HOOC-(CH_2)_n-COOH$ where n is 0-4, and the like. Non-toxic pharmaceutical base addition salts include salts of bases such as sodium, potassium, calcium, ammonium, and the like. Those skilled in the art will recognize a wide variety of non-toxic pharmaceutically acceptable addition salts.

EXAMPLES

Example 1

Synthesis of Cold F19 PSMA Inhibitor

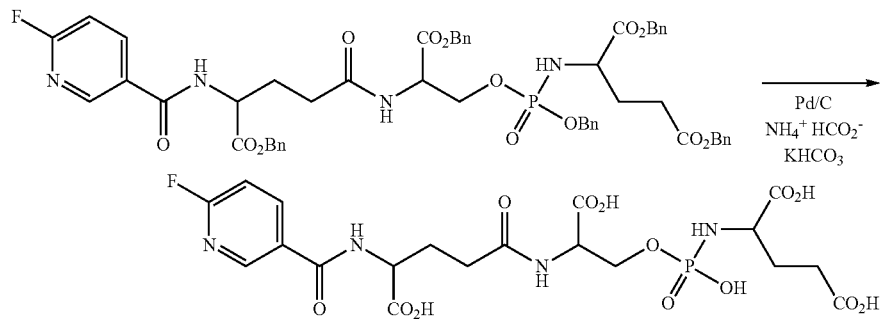

The precursor (8.9 mg, 0.00875 mmol) was dissolved in THF (2 drops) and ethanol (400 µL). A suspension of 10% Pd/C (10.9 mg/800 µL in ethanol (200 µL) and 0.0256 mmol of $KHCO_3$ was added (25 µL of a 54.3 mg/250 µL solution). Ammonium formate (31 mg/200 µL water, 0.49 mmol) was added to initiate the reaction. The reaction was stirred at room temperature (without a cap) for 20 min, which was complete by TLC. The reaction mixture was filtered through a 0.2 µm PTFE Whatman disc and flushed through with a mixture of ethanol:water (9:1 vol:vol ratio). The reaction mixture was evaporated to dryness and the product confirmed by $^1H$ and $^{31}P$ NMR.

Example 2

Pendant Group-Bearing Precursors of PSMA Inhibitors for Indirect Labeling with $^{18}F$ PSMA inhibitors can be outfitted with a motif that could be used in click chemistry or biorthogonal click chemistry (such as the Staudinger ligation, azide-alkyne Huisgen cycloaddition, Diels-Alder, or hydrazone formation) to couple to a detectable group (fluorescent dye, covalently attached radionuclide such as $^{18}F$ or $^{123}I$, a chelated radioisotope such as $^{99m}Tc$, $^{64}a$, $^{68}Ga$ or $^{111}In$, a chelated MRI contrast agent, or therapeutic agent including chelated and covalently bonded radiotherapeutics such as $^{177}Lu$, $^{90}Y$, $^{125}I$, $^{131}I$, or cytotoxic drugs like doxorubicin, camptothecin, or paclitaxel. Examples of some click chemistry handles are shown below on the CTT-54 scaffold.

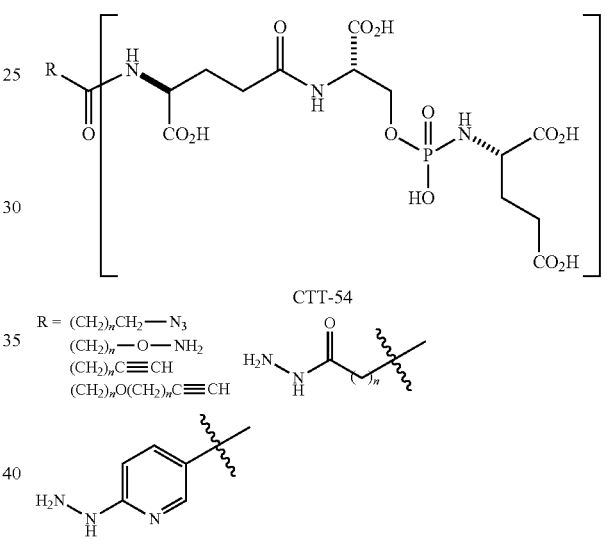

Indirect 18F-radiolabeling of PSMA inhibitors such as CTT-54 can be achieved, for example, by reacting PSMA inhibitors with amine-reactive radiolabeled prosthetic groups such as N-Succinimidyl-4-18F-Fluorobenzoate or 6-[18F]fluoronicotinic acid tetrafluorophenyl ester. See, Lapi, S. E., et al., Assessment of an 18F-labeled phosphoramidate peptidomimetic as a new prostate-specific membrane antigen-targeted imaging agent for prostate cancer. J Nucl Med, 2009. 50(12): p. 2042-8, and Olberg, D. E., et al., One step radiosynthesis of 6-[(18)F]fluoronicotinic acid 2,3,5,6-tetrafluorophenyl ester ([(18)F]F-Py-TFP): a new prosthetic group for efficient labeling of biomolecules with fluorine-18. J Med Chem. 53(4): p. 1732-40, both of which are herein incorporated by reference.

Two alternative routes of indirect labeling which are applicable to the compounds of the present invention, including without limitation to protected or deprotected pyridine derivatives, are presented below.

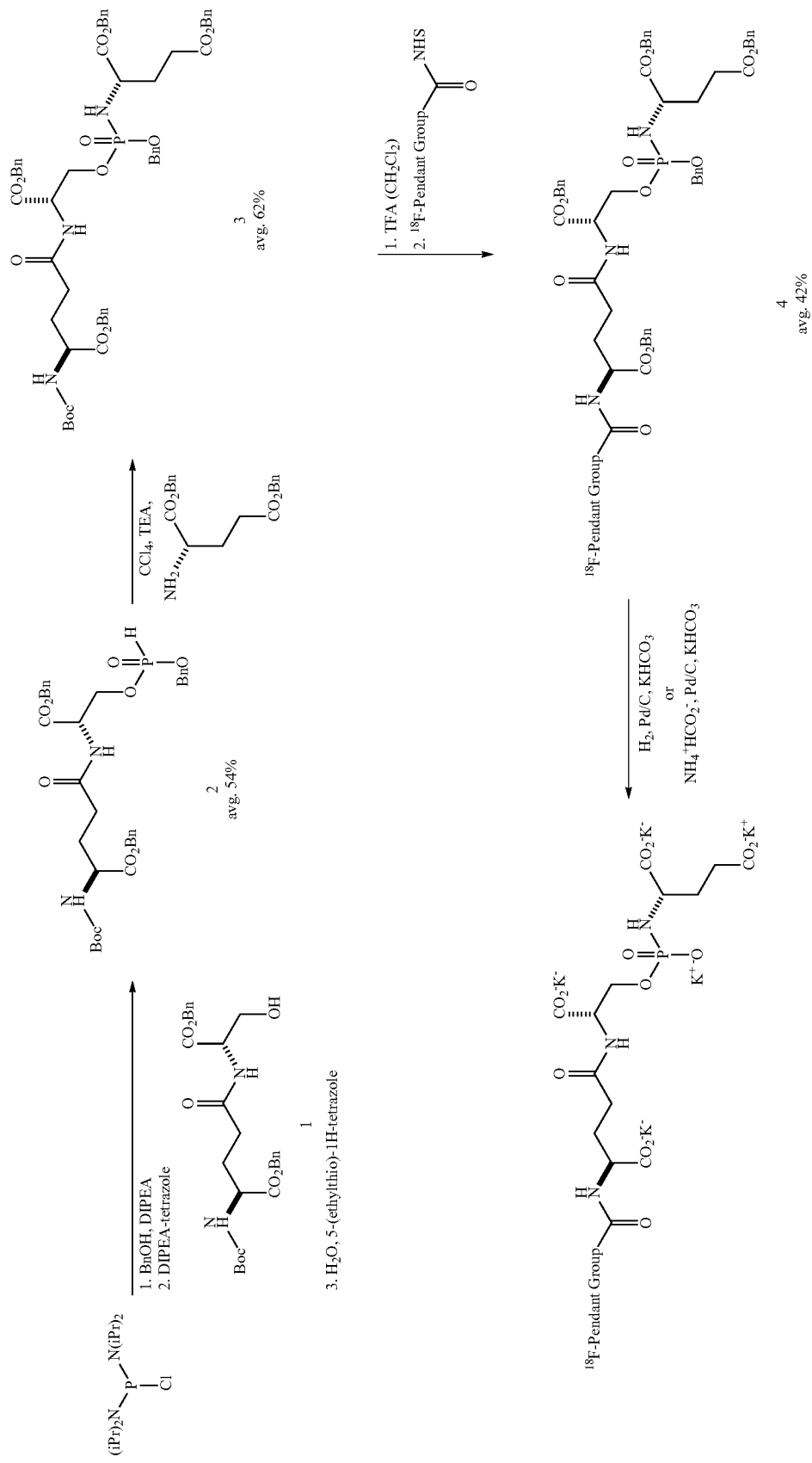

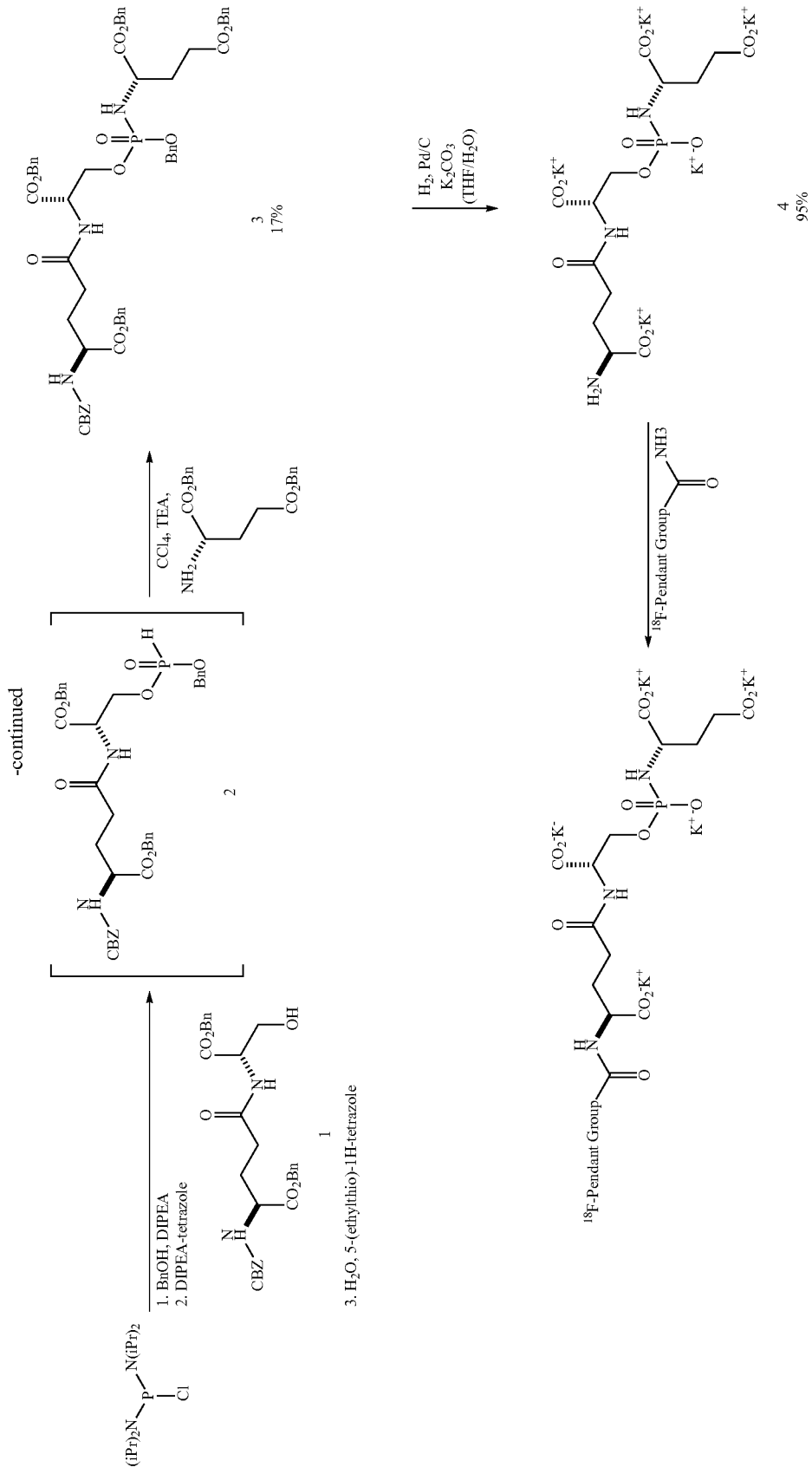

Example 3

Preparation of Authentic Standards

For the single substituted nicotinamide model compounds, an authentic standard was prepared as the 6-fluoronicotinamide analog. To prepare for the labeling of the tosyloxyethylcarbamoyl benzamide from FIG. 1, we completed the preparation of the cold authentic standard as shown below.

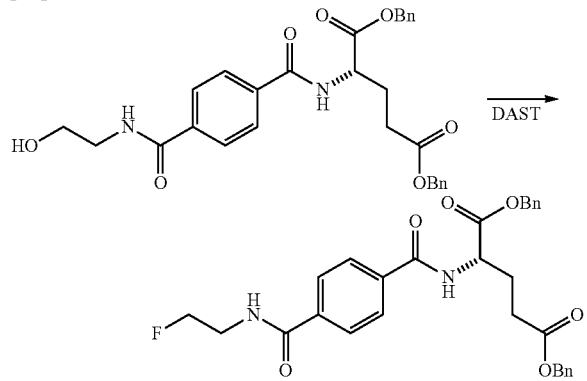

Example 4

$^{99m}$Tc-Labeling Experiments

Chelate conjugates of CTT-54 have recently been examined for the labeling of PSMA+ cells using $^{99m}$Tc as the guest radionuclide in the chelate structure. The rationale for these studies is to prepare for the development of alternative payloads for PET imaging ($^{68}$Ga or $^{64}$Cu) and radiotherapy. $^{99m}$Tc serves as a model radionuclide for biodistribution studies.

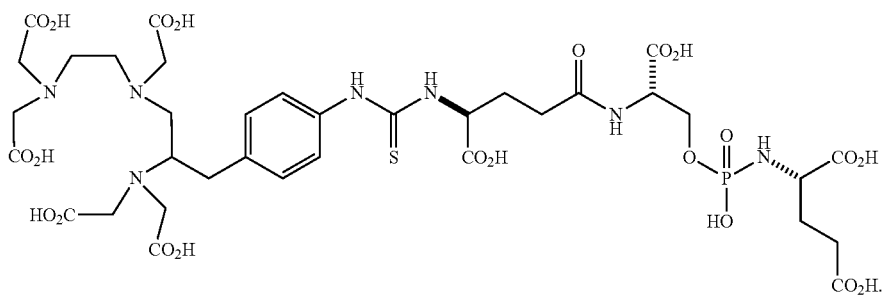

DTPA-SCN-CTT-54

Figure 2:
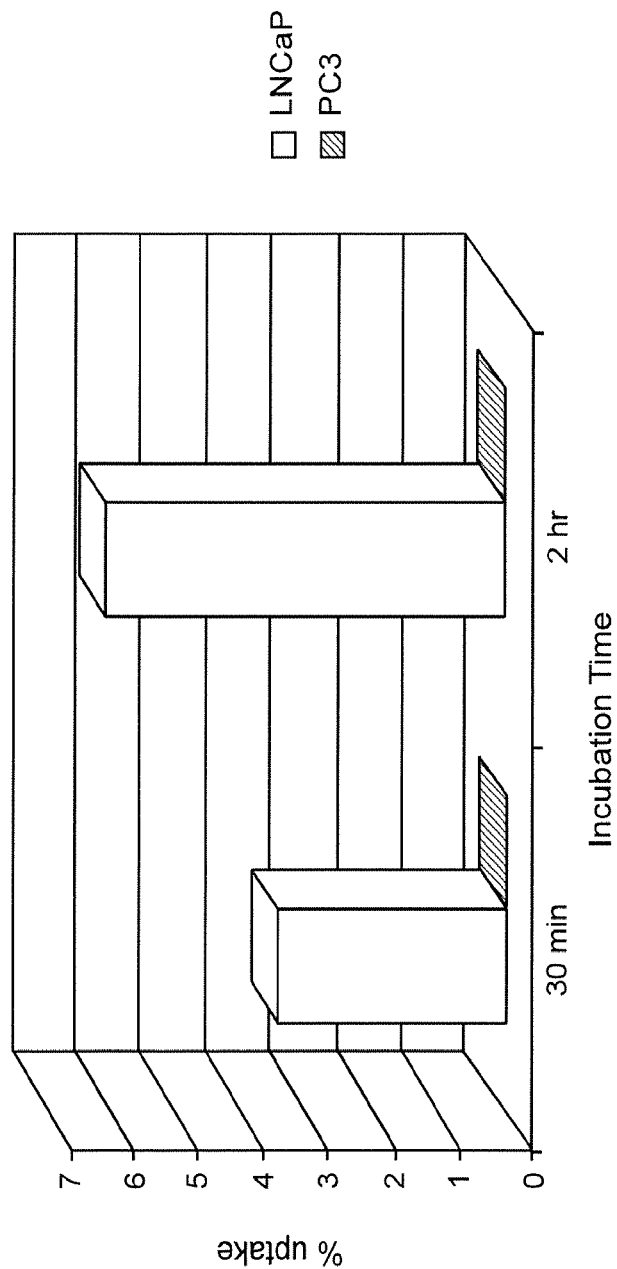
FIG. 2 shows uptake DTPA-SCN-CTT-54 labeled with $^{99m}Tc(CO)_3$ by LNCaP (PSMA+) and PC3 (PSMA−) cells.
Figure 3:
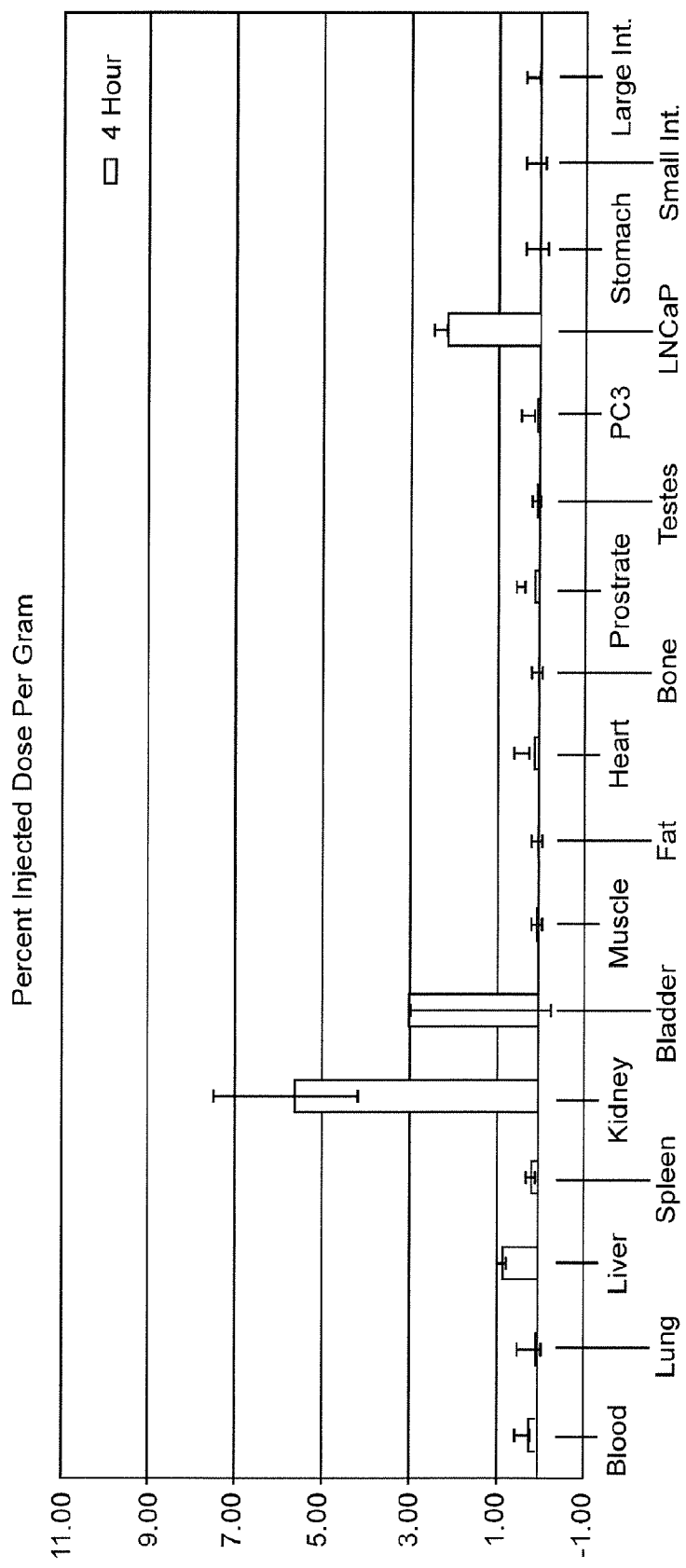
FIG. 3 shows biodistribution of the $^{99m}Tc$-labeled probe in a LNCaP PSMA+ tumor xenograft model 4 hours following tail-vein probe injection.

Both LNCaP (PSMA+) and PC3 (PSMA−) cells were treated with DTPA-SCN-CTT-54 labeled with pertechnetate ($^{99m}$TcO$_4^-$) reduced with SnCl$_2$. At increasing time points at 37° C., cells were washed free of the probe and uptake was determined as a percentage of the total amount of probe applied. Uptake was exclusive for LNCaP cells as shown in FIG. 2. Similarly, cells were treated with DTPA-SCN-CTT-54 labeled with $^{99m}$Tc(CO)$_3$ and the data shown in FIG. 3. Preliminary studies to determine the extent of internalization of the probe were completed and the results suggest that greater than 80% internalization (See, Table 4).

TABLE 4

| Time | % uptake | % internalization |
|---|---|---|
| 30 min | 2.30 | 71.9 |
| 2 hr | 2.94 | 71.0 |
| 4 hr | 2.34 | 79.5 |

Our data suggests that binding to the cell surface happens rapidly (within 30 min), which is followed by rapid internalization (greater than 70% within 30 min).

Competitive Binding Experiments.

To confirm that the uptake of the probe was due to PSMA binding, cells were preincubated with the unlabeled inhibitor core CTT-54 for 30 min prior to incubation of the probe for 2 hours. In a dose-dependent manner, as shown in Table 5, CTT-54 blocked the binding of the radiolabeled probe.

TABLE 5

| Concentration (nM) | % Uptake |
|---|---|
| 0 | 4.46 |
| 0.5 | 2.80 |
| 5 | 1.26 |
| 50 | 0.38 |
| 500 | 0.26 |

Biodistribution Studies.

Both PSMA+ (LNCaP) and PSMA− (PC3) tumor xenografts were implanted in opposite rear flanks of each mouse. Thus, each mouse served as both a positive and negative control. In biodistribution studies with the $^{99m}$Tc-labeled probe, substantial uptake was observed in the LNCaP PSMA+ tumor xenografts.

We claim:

1. A compound of the formula

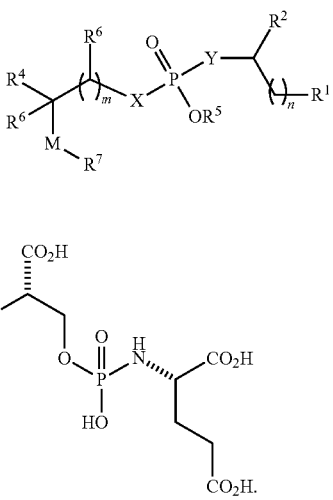

or a pharmaceutically acceptable salt thereof, wherein
X and Y are independently —O— or —N(R)—, wherein each R is independently hydrogen, —C$_1$-C$_7$ alkyl, —C$_1$-C$_7$ alkylaryl, —C$_1$-C$_7$ alkylheteroaryl, or a protecting group selected from the group consisting of substituted benzyl, t-butyl ester, alkyl esters, and fluorenylmethoxycarbonyl groups;
m is 1, 2, 3, 4, 5, or 6;
n is 1, 2, 3, 4, 5, or 6;
R$^1$ and R$^2$ are each independently —C(O)OR$^3$, —C(O)N(R$^3$)$_2$, —P(O)(OR$^3$)$_2$, —OP(O)(OR$^3$)$_2$, —S(O)$_2$R$^3$, —S(O)$_2$OR$^3$, —S(O)$_2$N(R$^3$)$_2$, or tetrazolyl; each
R$^3$ is independently hydrogen, —C$_1$-C$_7$ alkyl, —C$_1$-C$_7$ alkylaryl, —C$_1$-C$_7$ alkylheteroaryl, or a protecting group selected from the group consisting of substituted benzyl, t-butyl ester, alkyl esters, and fluorenylmethoxycarbonyl groups;
R$^4$=CO$_2$H
R$^5$ is hydrogen, —C$_1$-C$_7$ alkyl, —C$_1$-C$_7$ alkylaryl, —C$_1$-C$_7$ alkylheteroaryl, or a protecting group selected from the group consisting of substituted benzyl, t-butyl ester, alkyl esters, and fluorenylmethoxycarbonyl groups;

each $R^6$ is independently hydrogen, or $C_1$-$C_4$ alkyl;

M is —N($R^{31}$)—, or —CH$_2$—, wherein $R^{31}$ is hydrogen, —$C_1$-$C_7$ alkyl, —$C_1$-$C_7$ alkylaryl, —$C_1$-$C_7$ alkylheteroaryl, or a protecting group selected from the group consisting of substituted benzyl, t-butyl ester, alkyl esters, and fluorenylmethoxycarbonyl groups;

$R^7$ is -L-$R^{10}$, wherein

L is —C(O)—, -(Pep)-C(O)—, —C(O)N(H)—, —C(O)O—, —C(S)N(H)—, or —C(S)O—, wherein Pep is a polypeptide of 1-20 amino acids; and $R^{10}$ is -aryl-$R^9$, -heteroaryl-$R^9$, —$C_1$-$C_7$ alkyl-aryl-$R^9$, —$C_1$-$C_7$ alkyl-hetero aryl-$R^9$, —$C_1$-$C_7$ alkyl-$R^8$, -aryl-$C_1$-$C_7$ alkyl-$R^8$, or -heteroaryl-$C_1$-$C_7$ alkyl-$R^8$, wherein the aryl, heteroaryl, -alkyl-aryl, -aryl-alkyl, -alkyl-heteroaryl, and -heteroaryl-alkyl groups are optionally and independently substituted with one, two, or three groups which are each independently halomethyl, dihalomethyl, trihalomethyl, —C(O)$R^{11}$, —CO(O)$R^{12}$, —C(O)N($R^{12}$)$_2$, wherein each $R^{11}$ is independently hydrogen, —$C_1$-$C_7$ alkyl, —$C_1$-$C_7$ alkylaryl, or —$C_1$-$C_7$ alkylheteroaryl; and each $R^{12}$ is independently $R^{11}$ or a protecting group selected from the group consisting of substituted benzyl, t-butyl ester, alkyl esters, and fluorenylmethoxycarbonyl groups; and $R^8$ is —C(H)(COO$R^3$)N($R^{15}$)-$L^1$-($C_1$-$C_7$)alkyl-$R^9$, —C(H)(COO$R^3$)N($R^{15}$)-$L^1$-aryl-$R^9$, —C(H)(COO$R^3$)N($R^{15}$)-$L^1$-heteroaryl-$R^9$, —C(H)(COO$R^3$)N($R^{15}$)-$L^1$-aryl($C_1$-$C_7$)alkyl-$R^9$, —C(H)(COO$R^3$)N($R^{15}$)-$L^1$-heteroaryl($C_1$-$C_7$)alkyl-$R^9$, —C(H)(COO$R^3$)N($R^{15}$)-$L^1$-G-CH$_2$CH$_2$—$R_9$, —C(H)(COO$R^3$)N($R^{15}$)-$L^1$-($C_1$-$C_7$)alkyl-O—(C $C_1$-$C_7$)alkyl-$R_9$, or —$R^9$, wherein $R^{15}$ is hydrogen, —$C_1$-$C_7$ alkyl, —$C_1$-$C_7$ alkylaryl, —$C_1$-$C_7$ alkylheteroaryl, or a protecting group selected from the group consisting of substituted benzyl, t-butyl ester, alkyl esters, and fluorenylmethoxycarbonyl groups;

$L^1$ is —C(O)—, —C(O)N(H)—, —C(O)O—, —C(S)N(H)—, or —C(S)O—; and the aryl, heteroaryl, arylalkyl, and heteroarylalkyl groups are optionally substituted with one, two, or three groups which are each independently halomethyl dihalomethyl, trihalomethyl, —C(O)$R^{81}$, —CO(O)$R^{82}$, —C(O)N($R^{82}$)$_2$—, wherein each $R^{81}$ is independently hydrogen, —$C_1$-$C_7$ alkyl, —$C_1$-$C_7$ alkylaryl, or —$C_1$-$C_7$ alkylheteroaryl; and each $R^{82}$ is independently $R^{81}$ or a protecting group selected from the group consisting of substituted benzyl, t-butyl ester, alkyl esters, and fluorenylmethoxycarbonyl groups;

G is —(CH$_2$CH$_2$O)$_q$—, wherein q is an integer from 1 to 200;

$R_9$ is (i) —N$_3$, —C≡CH—, —ONH$_2$, —C(O)N(H)NH$_2$, or —N(H)NH$_2$;

(ii) a detectable label, a cytotoxic group, or biotin;

(iii) a pendant group comprising either a detectable label, a cytotoxic group, or biotin; or (iv) a pendant group bonded to a solid support, wherein the cytotoxic group is selected from the group consisting of chelated or bonded radioisotopes, photosensitizers, paclitaxel, camptothecin, doxorubicin, and lysosomal disrupting agents, and wherein the pendant group is a group of the formula —($C_0$-$C_{10}$ alkyl-D)$_{0-1}$-$C_0$-$C_{10}$alkyl-, wherein D is a bond, aryl, heteroaryl, $C_3$-$C_8$cycloalkyl, or heterocyclyl; and no more than one methylene in each alkyl group is optionally and independently replaced by —O—, —S—, —N($R^{00}$)—, —C(H)=C(H)—, —C(O)—, —S(O)—, —S(O)$_2$—, —P(O)(OH)—, —OP(O)(OH)—, —P(O)(OH)O—, —N($R^{00}$)P(O)(OH)—, —P(O)(OH)N($R^{00}$)—, —OP(O)(OH)O—, —OP(O)(OH)N($R^{00}$)—, —N($R^{00}$)P(O)(OH)O—, —N($R^{00}$)P(O)(OH)N($R^{00}$)—, —C(O)O—, —C(O)N($R^{00}$)—, —OC(O)—, —N($R^{00}$)C(O)—, —S(O)O—, —OS(O)—, —S(O)N($R^{00}$)—, —N($R^{00}$)S(O)—, S(O)$_2$O—, —OS(O)$_2$—, —S(O)$_2$N($R^{00}$)—, —N($R^{00}$)S(O)$_2$—, —OC(O)O—, —OC(O)N($R^{00}$)—, —N($R^{00}$)C(O)O—, —N($R^{00}$)C(O)N($R^{00}$)—, —OS(O)O—, —OS(O)N($R^{00}$)—, —N($R^{00}$)S(O)O—, —N($R^{00}$)S(O)N($R^{00}$)—, —OS(O)$_2$O—, —(OS)(O)$_2$N($R^{00}$)—, —N($R^{00}$)S(O)$_2$O—, or —N($R^{00}$)S(O)$_2$N($R^{00}$)—, wherein each $R^{00}$ is independently hydrogen or $C_1$-$C_7$ alkyl.

2. The compound of claim 1, wherein $R^8$ is —C(H)(COO$R^3$)N(H)C(O)($C_1$-$C_7$)alkyl-$R^9$, —C(H)(COO$R^3$)N(H)C(O)hetero aryl-$R^9$, —C(H)(COO$R^3$)N(H)C(O)-G-CH$_2$CH$_2$—$R^9$, —C(H)(COO$R^3$)N(H)C(O)($C_1$-$C_7$)alkyl-O—($C_1$-$C_7$) alkyl-$R^9$, or —$R^9$.

3. The compound of claim 1, according to the formula, $$R^{20}-L^1-\underset{R^{15}}{N}-\underset{COOR^3}{\overset{O}{\underset{|}{C}}}_p-\underset{R^{31}}{N}-\underset{R^6}{\overset{R^4\;R^6}{\underset{|}{C}}}_m-\overset{Y}{\underset{OR^5}{\overset{||}{P}}}-(\phantom{X})_n R^1$$

and pharmaceutically acceptable salts thereof, wherein p is 0 or 1; $R^{20}$ is —$C_1$-$C_7$ alkyl-$R^9$, -aryl-$R^9$, aryl($C_1$-$C_7$)alkyl-$R^9$, or -heteroaryl-$R^9$.

4. The compound of claim 1, wherein $R^1$ and $R^2$ are each —C(O)OH.

5. The compound of claim 1, wherein $R^4$ is —C(O)OH.

6. The compound of claim 1, wherein each $R^3$ is hydrogen.

7. The compound of claim 1, wherein $R^9$ is a detectable label.

8. A composition comprising a compound of any one of claims 1-5, 6 and 7 together with a pharmaceutically acceptable carrier, excipient, and/or diluent.

9. The compound of claim 3, wherein: $L^1$ is —C(O)— or —C(S)N(H)—; $R^{20}$ is -aryl-$R^9$ or aryl-$C_1$alkyl-$R^9$ and $R^9$ is a detectable label.

10. The compound of claim 9, wherein $R^1$ and $R^2$ are —C(O)O$R^3$ and $R^3$ is H;

$R^5$=H;

Y=NR and R=H;

n=2;

X=O;

m=3;

$R^6$=H;

$R^4$=CO$_2$H;

$R^{31}$=H;

p=1;

$R^3$ and $R^{15}$=H;

$L^1$ is —C(S)N(H)—;

$R^{20}$ is aryl-$C_1$alkyl-$R^9$; and $R^9$ is detectable label $^{177}$Lu coordinated to chelating group 1,4,7,10-tetraazacyclododecanetetraacetic acid (DOTA).

* * * * *